United States Patent
Han et al.

(10) Patent No.: US 11,910,711 B2
(45) Date of Patent: Feb. 20, 2024

(54) CYCLIC COMPOUND AND ORGANIC LIGHT EMITTING DEVICE COMPRISING SAME

(71) Applicant: LG CHEM, LTD., Seoul (KR)

(72) Inventors: Su Jin Han, Daejeon (KR); Dong Hoon Lee, Daejeon (KR); Boon Jae Jang, Daejeon (KR); Sang Duk Suh, Daejeon (KR); Min Woo Jung, Daejeon (KR); Jungha Lee, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 372 days.

(21) Appl. No.: 17/285,179

(22) PCT Filed: Mar. 13, 2020

(86) PCT No.: PCT/KR2020/003542
§ 371 (c)(1),
(2) Date: Apr. 14, 2021

(87) PCT Pub. No.: WO2020/185038
PCT Pub. Date: Sep. 17, 2020

(65) Prior Publication Data
US 2021/0391544 A1  Dec. 16, 2021

(30) Foreign Application Priority Data

Mar. 14, 2019 (KR) .................. 10-2019-0029507
Mar. 12, 2020 (KR) .................. 10-2020-0030982

(51) Int. Cl.
*H10K 85/60* (2023.01)
*C07D 403/04* (2006.01)
(Continued)

(52) U.S. Cl.
CPC ....... *H10K 85/6572* (2023.02); *C07D 403/04* (2013.01); *C07D 403/14* (2013.01);
(Continued)

(58) Field of Classification Search
CPC .. C07D 209/82; C07D 251/24; C07D 403/04; C07D 403/10; C07D 403/14;
(Continued)

(56) References Cited

U.S. PATENT DOCUMENTS

2010/0084967 A1   4/2010   Takeda
2014/0346483 A1   11/2014  Yu et al.
(Continued)

FOREIGN PATENT DOCUMENTS

EP   3767698 A1     1/2021
JP   2015-530363 A  10/2015
(Continued)

OTHER PUBLICATIONS

Computer-generated English-language translation of KR-20180027457-A.*
(Continued)

*Primary Examiner* — Vu A Nguyen
(74) *Attorney, Agent, or Firm* — Bryan Cave Leighton Paisner LLP

(57) ABSTRACT

A cyclic compound represented by Chemical Formula 1 and an organic light emitting device using the same, the compound used as a material of an organic material layer of the organic light emitting device and providing improved properties of efficiency, driving voltage, and lifetime characteristics of the organic light emitting device.

(Continued)

[Chemical Formula 1]

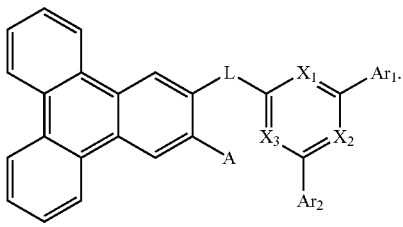

10 Claims, 1 Drawing Sheet

(51) Int. Cl.
  *C07D 403/14* (2006.01)
  *C07D 405/14* (2006.01)
  *C07D 409/14* (2006.01)
  *H10K 50/11* (2023.01)
  *H10K 50/15* (2023.01)
  *H10K 50/16* (2023.01)
  *H10K 50/17* (2023.01)

(52) U.S. Cl.
  CPC ......... *C07D 405/14* (2013.01); *C07D 409/14* (2013.01); *H10K 85/654* (2023.02); *H10K 85/6574* (2023.02); *H10K 85/6576* (2023.02); *H10K 50/11* (2023.02); *H10K 50/15* (2023.02); *H10K 50/16* (2023.02); *H10K 50/17* (2023.02); *H10K 50/171* (2023.02)

(58) Field of Classification Search
  CPC .. C07D 405/04; C07D 405/14; C07D 409/04; C07D 409/14
  See application file for complete search history.

(56) References Cited

U.S. PATENT DOCUMENTS

| | | |
|---|---|---|
| 2015/0200373 A1 | 7/2015 | Cho et al. |
| 2015/0228908 A1 | 8/2015 | Lee et al. |
| 2016/0013427 A1 | 1/2016 | Kim et al. |
| 2016/0072078 A1 | 3/2016 | Lee et al. |
| 2017/0077412 A1 | 3/2017 | Lim et al. |
| 2019/0237674 A1 | 8/2019 | Cha et al. |
| 2021/0188816 A1 | 6/2021 | Park et al. |
| 2021/0217966 A1 | 7/2021 | Parham et al. |

FOREIGN PATENT DOCUMENTS

| | | | |
|---|---|---|---|
| JP | 2018-538238 A | 12/2018 | |
| JP | 2019-023163 A | 2/2019 | |
| JP | 2021-528408 A | 10/2021 | |
| KR | 10-2010-0014603 A | 2/2010 | |
| KR | 10-1235369 B1 | 2/2013 | |
| KR | 10-2013-0073537 A | 7/2013 | |
| KR | 10-2016-0049083 A | 5/2016 | |
| KR | 10-1694487 B1 | 1/2017 | |
| KR | 10-2017-0031860 A | 3/2017 | |
| KR | 10-2017-0070359 A | 6/2017 | |
| KR | 10-2018-0027457 A | 3/2018 | |
| KR | 20180027457 A * | 3/2018 | ............ C09K 11/06 |
| KR | 10-2018-0045695 A | 5/2018 | |
| KR | 10-1906065 B1 | 10/2018 | |
| WO | 03/012890 A2 | 2/2003 | |
| WO | 2013/112557 A1 | 8/2013 | |
| WO | 2015/034125 A1 | 3/2015 | |
| WO | 2015/139808 A1 | 9/2015 | |
| WO | 2018-021854 A1 | 2/2018 | |
| WO | 2018-074881 A1 | 4/2018 | |
| WO | 2018/087346 A1 | 5/2018 | |
| WO | 2019-176605 A1 | 9/2019 | |

OTHER PUBLICATIONS

International Search Report from PCT/KR2020/003542, dated Jun. 24, 2020.
Written Opinion of the ISA from PCT/KR2020/003542, dated Jun. 24, 2020.

* cited by examiner

[FIG. 1]
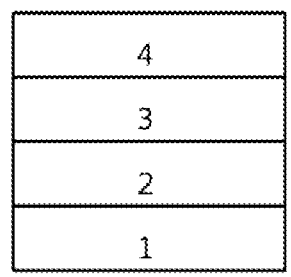
[FIG. 2]
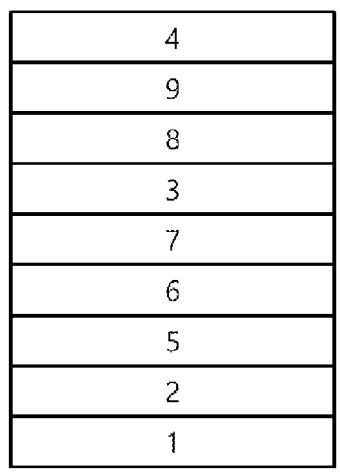

CYCLIC COMPOUND AND ORGANIC LIGHT EMITTING DEVICE COMPRISING SAME

CROSS-REFERENCE TO RELATED APPLICATIONS

This application is a National Stage Application of International Application No. PCT/KR2020/003542 filed on Mar. 13, 2020, which claims priority to and benefit of the filing dates of Korean Patent Application No. 10-2019-0029507 filed on Mar. 14, 2019, and Korean Patent Application No. 10-2020-0030982 filed on Mar. 12, 2020, the entire contents of which are incorporated herein by reference.

FIELD OF DISCLOSURE

The present disclosure relates to a novel compound and to an organic light emitting device including the same.

BACKGROUND

In general, an organic light emitting phenomenon refers to a phenomenon where electrical energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, holes are injected from an anode into the organic material layer and electrons are injected from the cathode into the organic material layer, and when the injected holes and electrons meet each other, an exciton is formed, and light is emitted when the exciton falls to a ground state.

There is a continuing need for the development of new materials for the organic materials used in these organic light emitting devices.

RELATED ARTS

Korean Patent Laid-open Publication No. 10-2013-073537

DETAILED DESCRIPTION

Technical Problem

The present disclosure relates to a novel compound and to an organic light emitting device including the same.

It is an object of the present disclosure to provide a novel compound and an organic light emitting device including the same.

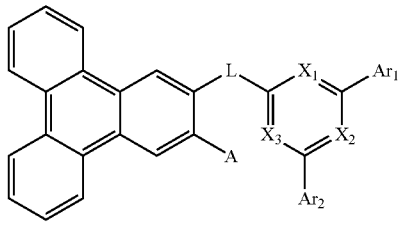

[Chemical Formula 1]

In Chemical Formula 1,

L is a direct bond, or a substituted or unsubstituted $C_{6-60}$ arylene,

A is a substituted or unsubstituted carbazolyl, $X_1$, $X_2$, and $X_3$ are each independently N or CH, and at least one of $X_1$, $X_2$, and $X_3$ is N, and $Ar_1$ and $Ar_2$ are each independently a substituted or unsubstituted $C_{6-60}$ aryl, or a substituted or unsubstituted $C_{5-60}$ heteroaryl containing one to three heteroatoms selected from the group consisting of N, O, and S.

In another aspect of the disclosure, there is provided an organic light emitting device including: a first electrode; a second electrode provided to face the first electrode; and one or more organic material layers provided between the first electrode and the second electrode, wherein one or more layers of the organic material layers include the compound represented by Chemical Formula 1.

Advantageous Effects

The compound represented by Chemical Formula 1 described above can be used as a material of an organic material layer of an organic light emitting device, and may improve efficiency, achieve a low driving voltage, and/or improve lifetime characteristics in the organic light emitting device. In particular, the compound represented by Chemical Formula 1 can be used as a material for hole injection, hole transport, hole injection and transport, light emission, electron transport, or electron injection.

BRIEF DESCRIPTION OF DRAWINGS

FIG. 1 depicts an example of an organic light emitting device including a substrate 1, an anode 2, a light emitting layer 3, and a cathode 4.

FIG. 2 depicts an example of an organic light emitting device including a substrate 1, an anode 2, a hole injection layer 5, a hole transport layer 6, an electron inhibition layer 7, a light emitting layer 3, an electron transport layer 8, an electron injection layer 9, and a cathode 4.

DETAILED DESCRIPTION

Hereinafter, the present disclosure will be described in more detail to help understanding of the present disclosure.

In the present specification,

means a bond connected to another substituent group.

As used herein, the term "substituted or unsubstituted" means that substitution is performed by one or more substituent groups selected from the group consisting of: deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are linked or there is no substituent group. For example, the term "substituent group where two or more substituent groups are linked" may mean a biphenyl group. That is, the biphenyl group may be an aryl group, or may be interpreted as a substituent group where two phenyl groups are connected.

In the present specification the number of carbon atoms in a carbonyl group is not particularly limited, but is preferably 1 to 40 carbon atoms. Specifically, the carbonyl group may be compounds having the following structures, but is not limited thereto.

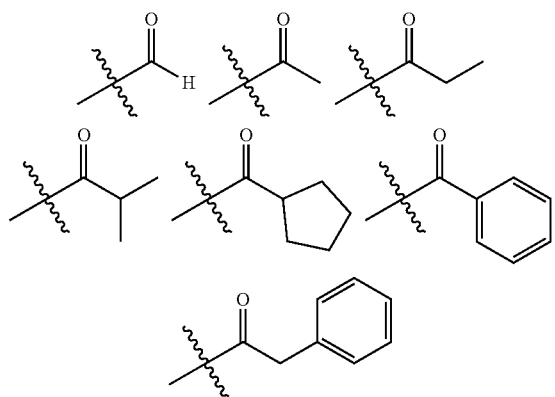

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

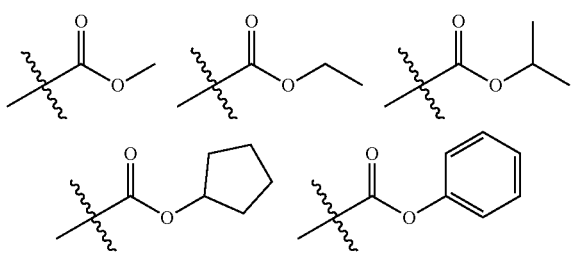

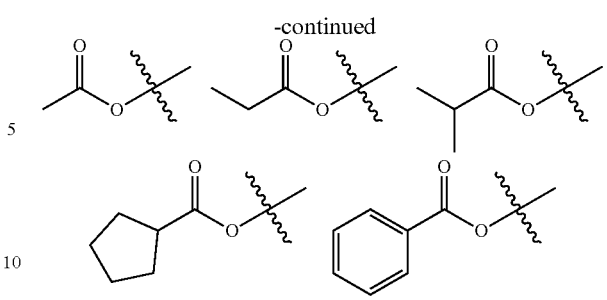

In the present specification, the number of carbon atoms in an imide group is not particularly limited, but is preferably 1 to 25. Specifically, the imide group may be compounds having the following structures, but is not limited thereto.

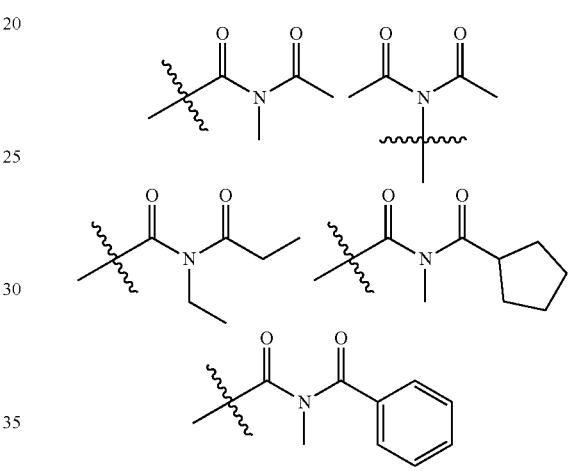

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, an alkyl group may be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group, or the like, but is not limited thereto.

In the present specification, a fluorenyl group may be substituted, and two substituent groups may be bonded to each other to form a spiro structure. In the case where the fluorenyl group is substituted,

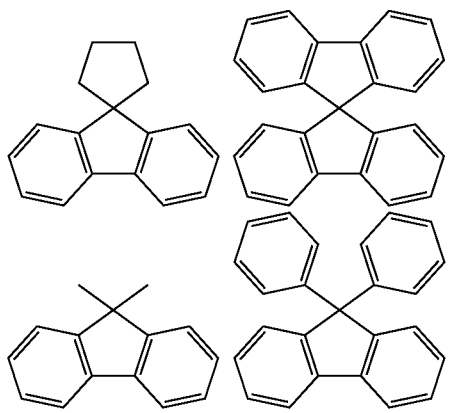

and the like can be formed. However, the structure is not limited thereto.

In the present specification, the heterocyclic group is a heterocyclic group containing at least one of O, N, Si, and S as a heteroatom, and the number of carbon atoms thereof is not particularly limited, but is preferably 2 to 60. Examples of the heteroaryl include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamines can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heterocyclic group can be applied, except that the heterocycle is not a monovalent group but is formed by combining two substituent groups.

The present disclosure provides a compound represented by Chemical Formula 1 as follows:

[Chemical Formula 1]

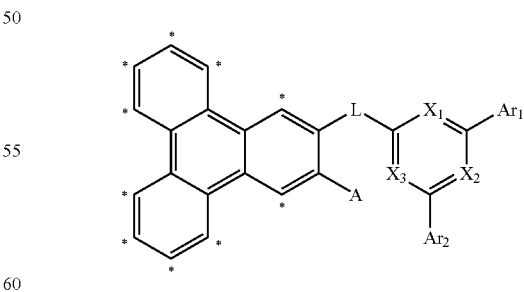

wherein, in Chemical Formula 1 above,

L is a direct bond, or a substituted or unsubstituted $C_{6-60}$ arylene,

A is a substituted or unsubstituted carbazolyl, $X_1$, $X_2$, and $X_3$ are each independently N or CH, and at least one of $X_1$, $X_2$, and $X_3$ is N, Ar$_1$ and Ar$_2$ are each independently a substituted or unsubstituted C$_{6-60}$ aryl, or a substituted or unsubstituted C$_{5-60}$ heteroaryl containing one to three heteroatoms selected from the group consisting of N, O, and S.

Meanwhile, in Chemical Formula 1, L, A, Ar$_1$, and Ar$_2$ are unsubstituted or substituted by deuterium.

Further, in Chemical Formula 1, a carbon which is represented by * is substituted only with hydrogen, and it means the carbon does not include other substituent group.

Preferably, the compound represented by Chemical Formula 1 is represented by the following Chemical Formulas 2 or 3:

[Chemical Formula 2]

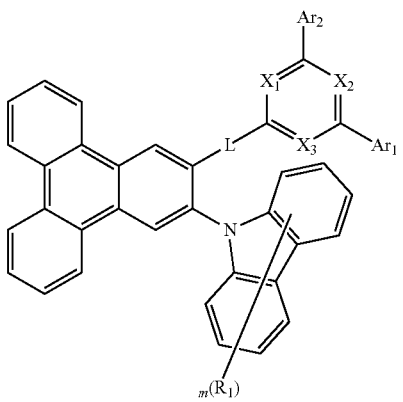

[Chemical Formula 3]

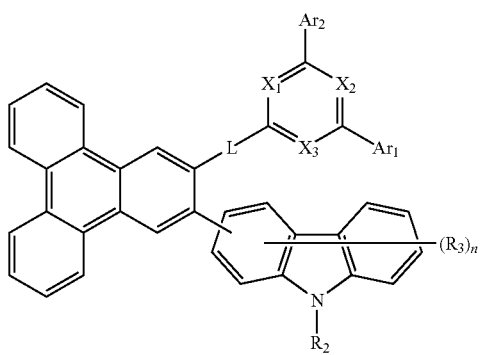

wherein, in Chemical Formula 2 and 3,

L, X$_1$, X$_2$, X$_3$, An, and Ar$_2$ are the same as defined in Chemical Formulas 1 and 2, R$_1$ are each independently hydrogen, deuterium, a substituted or unsubstituted C$_{1-60}$ alkyl, a substituted or unsubstituted C$_{6-60}$ aryl, or a substituted or unsubstituted C$_{5-60}$ heteroaryl containing at least one heteroatom selected from the group consisting of N, O, and S, R$_2$ is a substituted or unsubstituted C$_{1-60}$ alkyl, or a substituted or unsubstituted C$_{6-60}$ aryl, R$_3$ are each independently hydrogen, deuterium, a substituted or unsubstituted C$_{1-60}$ alkyl, a substituted or unsubstituted C$_{6-60}$ aryl, or a substituted or unsubstituted C$_{5-60}$ heteroaryl containing at least one heteroatom selected from the group consisting of N, O, and S, m is an integer of 0 to 8, and n is an integer of 0 to 7.

Meanwhile, in Chemical Formula 2 and 3, if R$_1$ and R$_3$ are not hydrogen or deuterium, the substituent groups can be each independently unsubstituted or substituted by at least one deuterium, and R$_2$ may be unsubstituted or substituted by at least one deuterium.

Preferably, all of X$_1$, X$_2$, and X$_3$ are N.

Preferably, L is a direct bond, phenylene unsubstituted or substituted by at least one deuterium, or biphenylylene unsubstituted or substituted by at least one deuterium.

Preferably, Ar$_1$ and Ar$_2$ are each independently phenyl, biphenylyl, terphenylyl, dimethylfluorenyl, naphthyl, phenanthrenyl, triphenylenyl, dibenzofuranyl, dibenzothiophenyl, carbazol-9-yl, 9-phenyl-9H-carbazolyl, benzoxazolyl, benzothiazolyl, 2-phenylbenzoxazolyl, or 2-phenyl benzothiazolyl, which are each independently unsubstituted or substituted by deuterium.

Preferably, R$_1$ are each independently hydrogen, deuterium, phenyl unsubstituted or substituted by at least one deuterium, dibenzofuranyl unsubstituted or substituted by at least one deuterium, dibenzothiophenyl unsubstituted or substituted by at least one deuterium, or carbazolyl unsubstituted or substituted by at least one deuterium.

If R$_1$ is deuterium, preferably m is 8.

If R$_1$ is not deuterium, preferably m is an integer of 0 to 2.

Preferably, R$_2$ are each independently phenyl unsubstituted or substituted by at least one deuterium.

Preferably, R$_3$ are each independently hydrogen, deuterium, phenyl unsubstituted or substituted by deuterium, dibenzofuranyl unsubstituted or substituted by deuterium, dibenzothiophenyl unsubstituted or substituted by deuterium, or carbazolyl unsubstituted or substituted by deuterium.

If R$_3$ is deuterium, preferably n is 8.

If R$_3$ is not deuterium, preferably n is an integer of 0 to 2.

Preferably, the compound represented by Chemical Formula 1 is any one selected from the group consisting of the following:

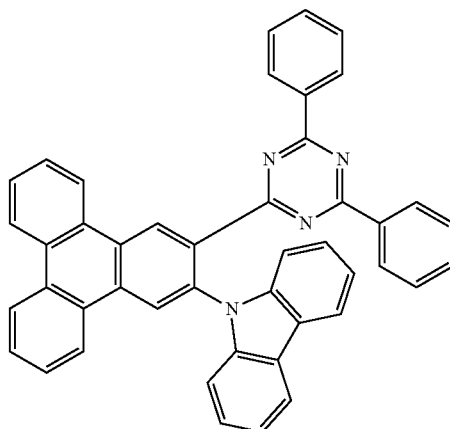

-continued
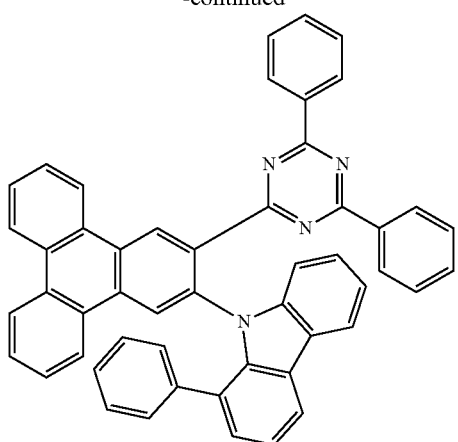
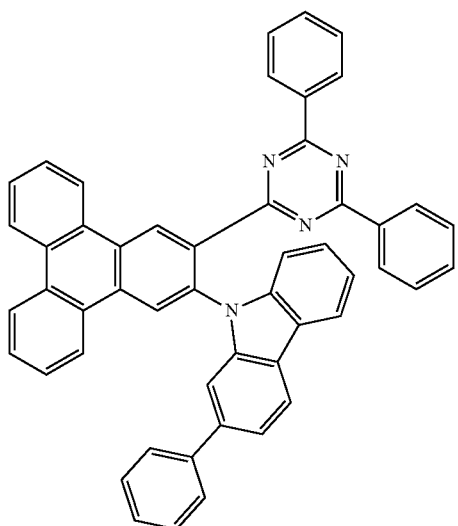
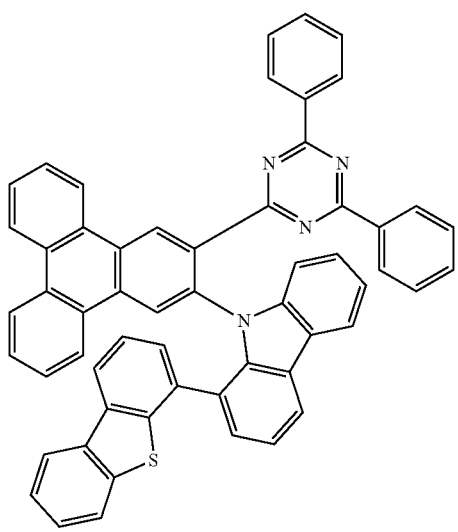
-continued
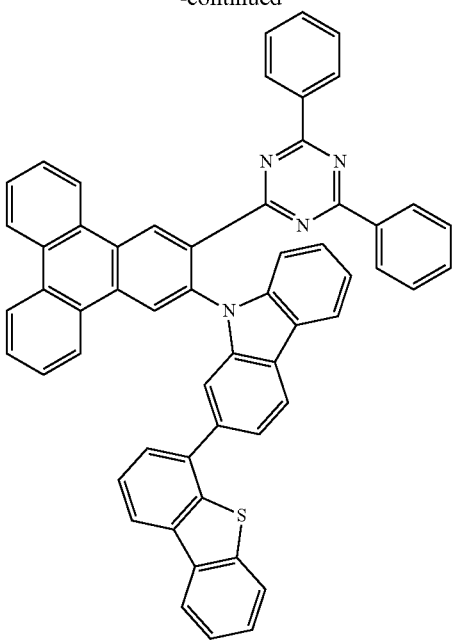
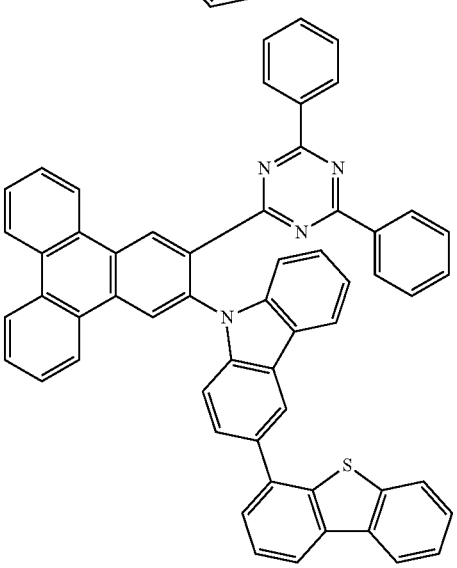
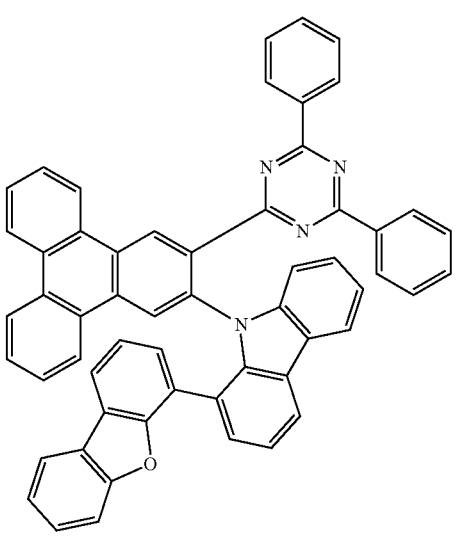

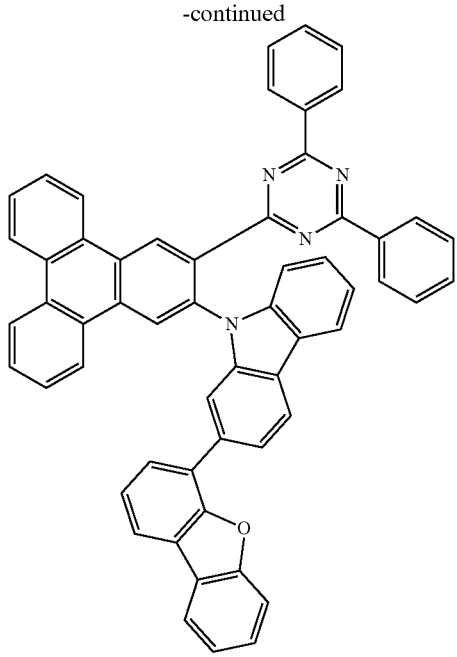
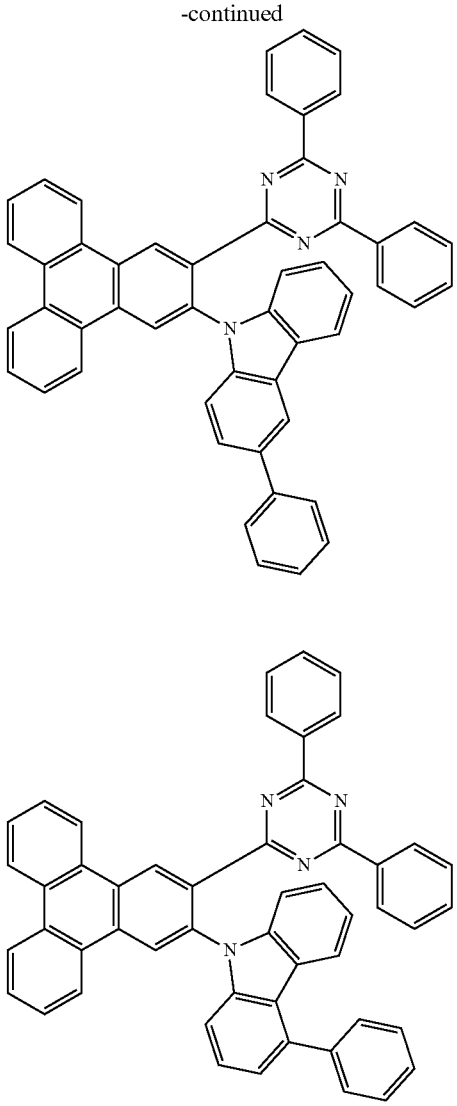
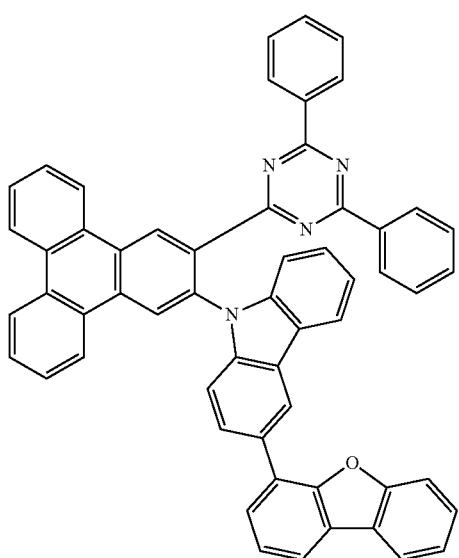
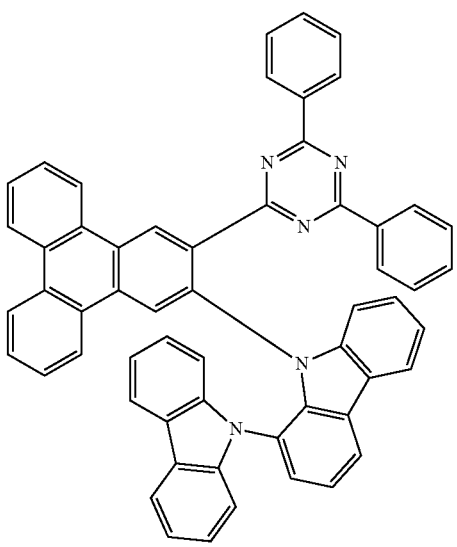

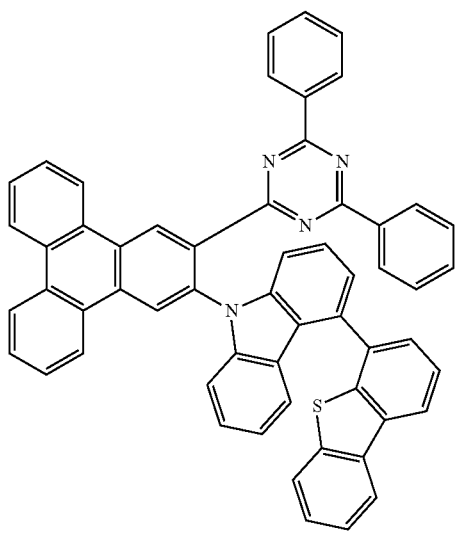
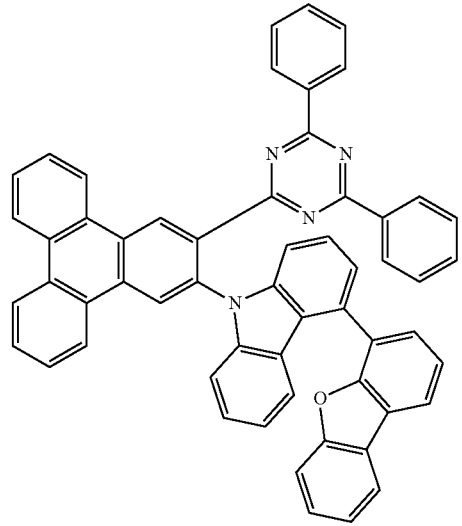
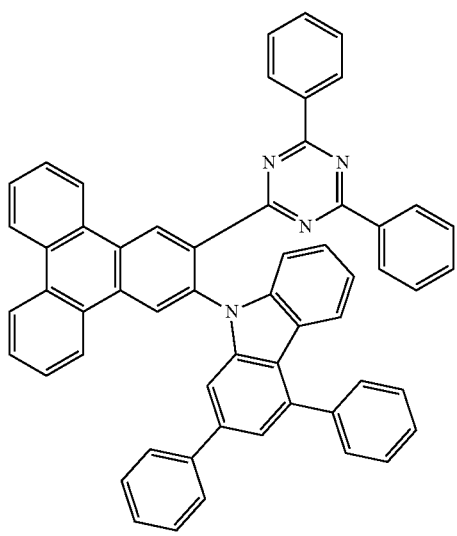
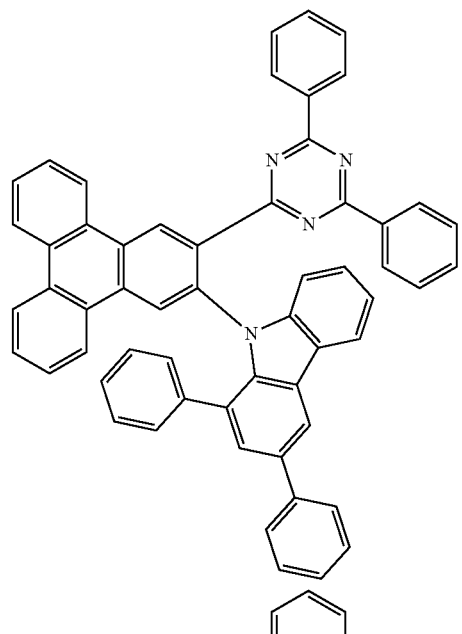
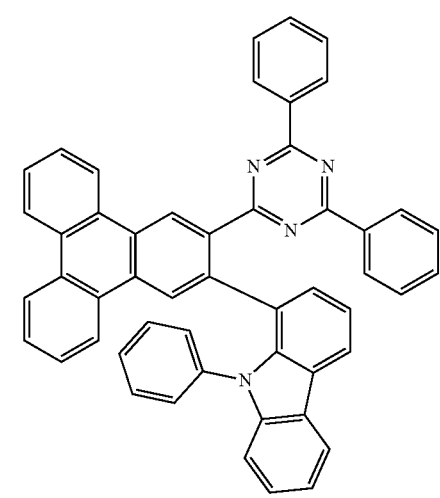
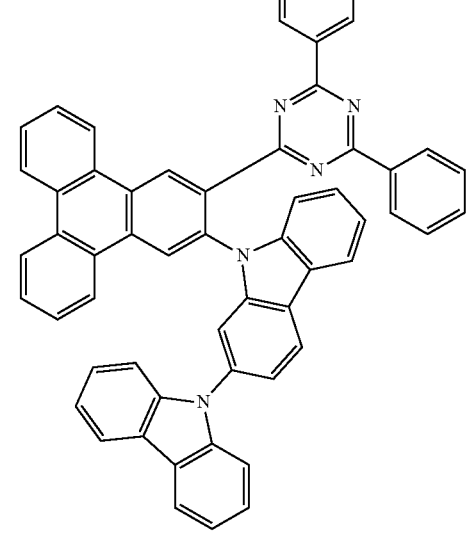

-continued
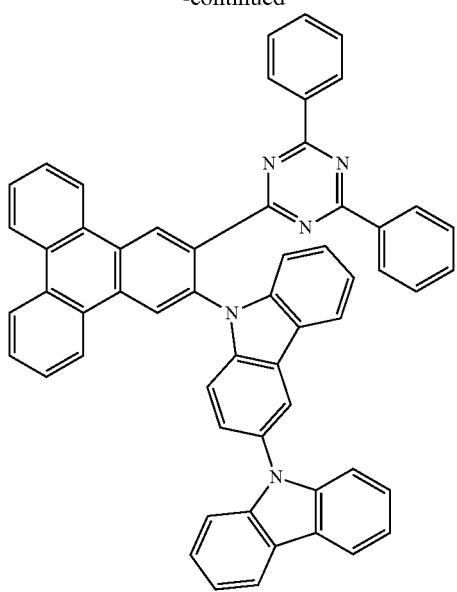
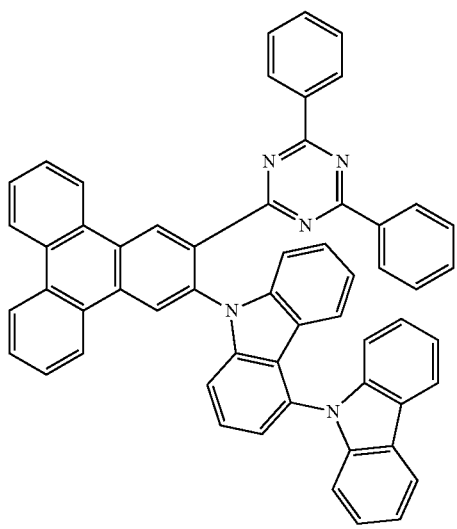
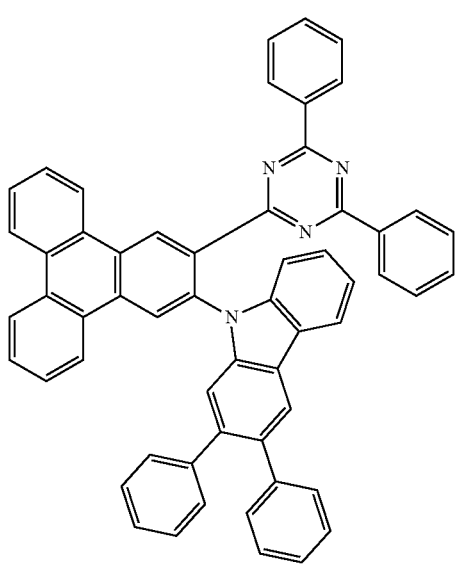
-continued
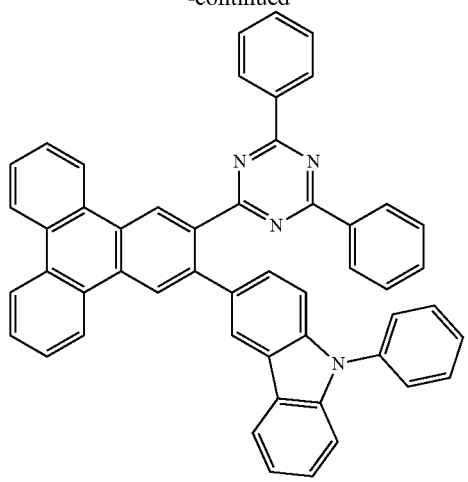
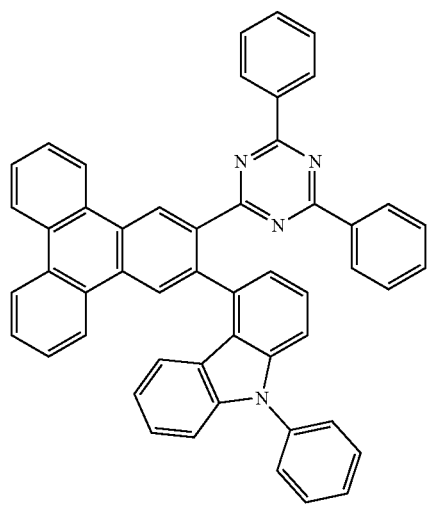
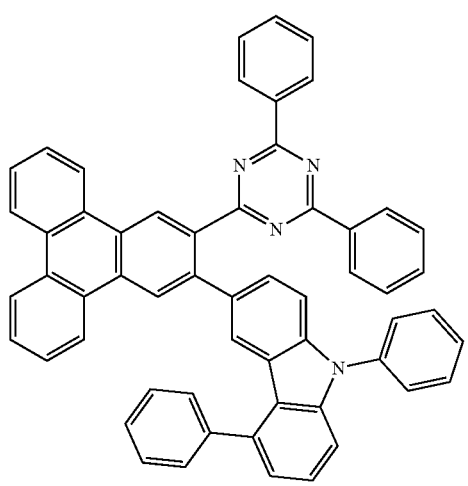

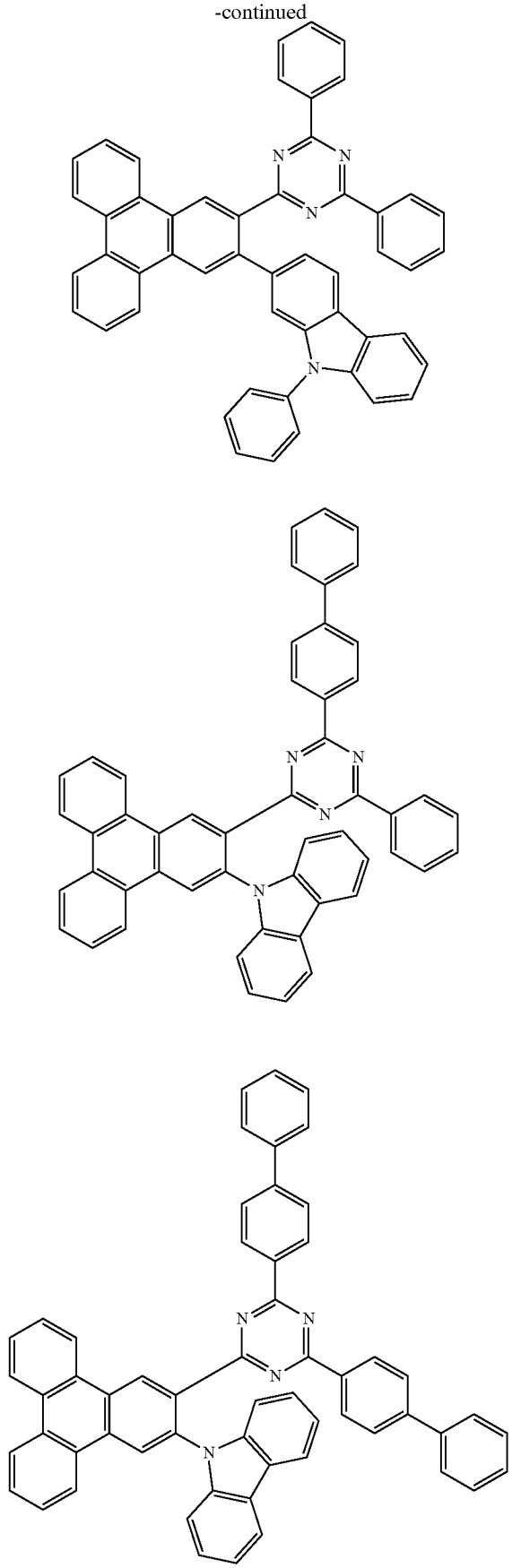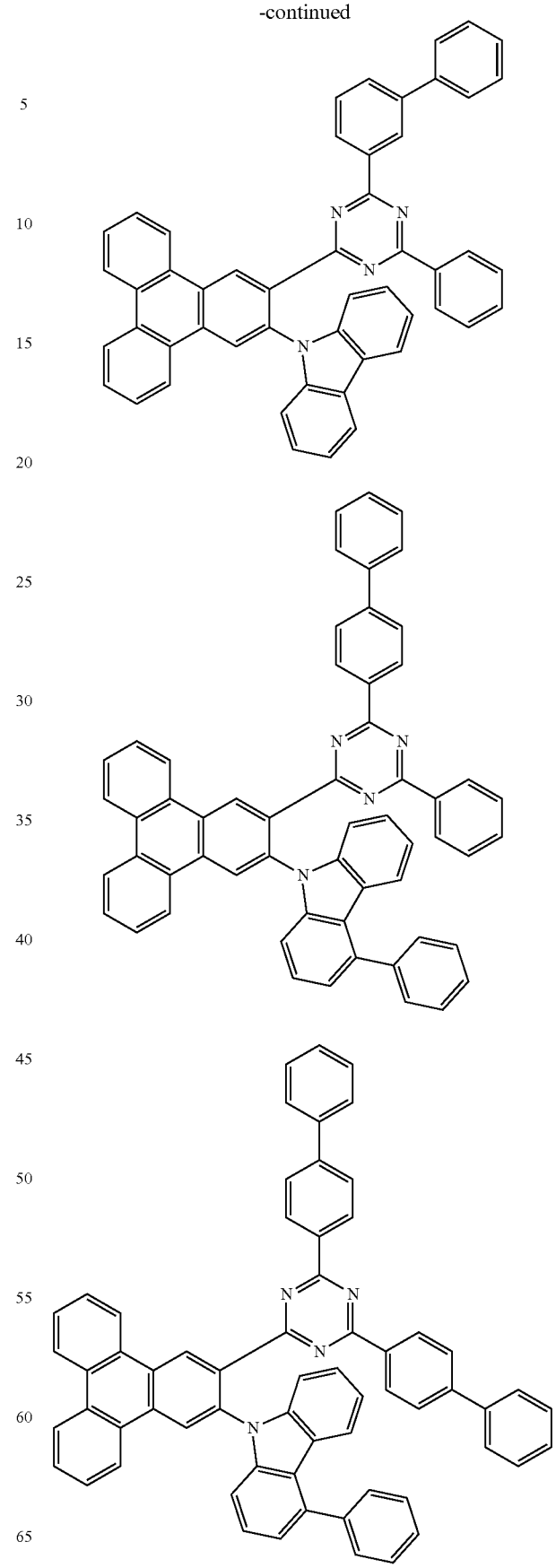

19
-continued
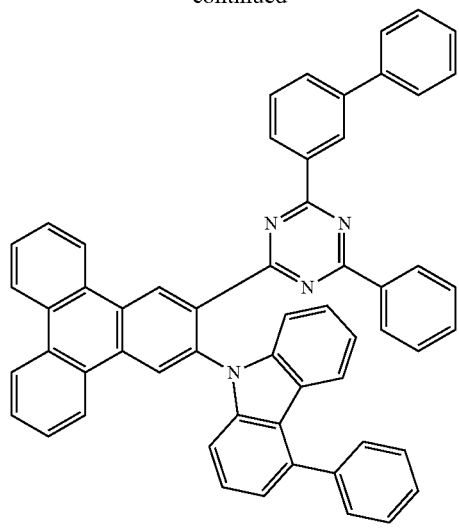
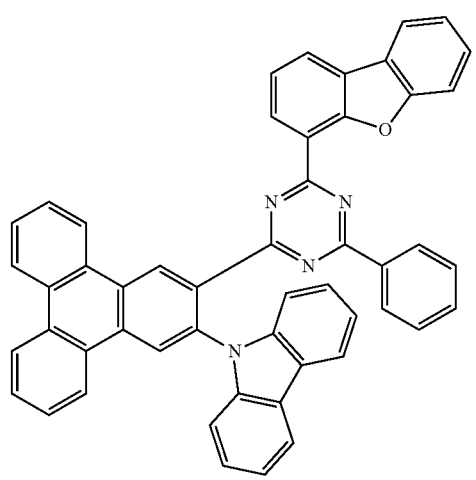
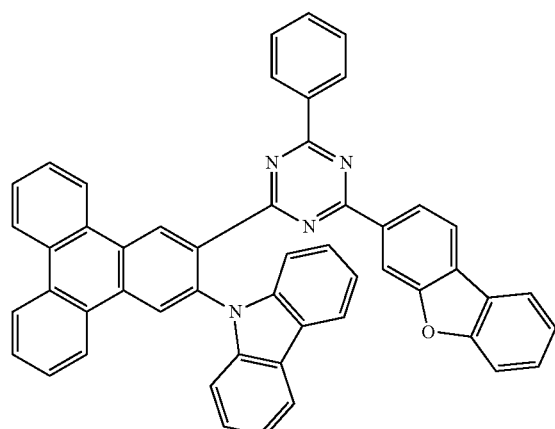
20
-continued
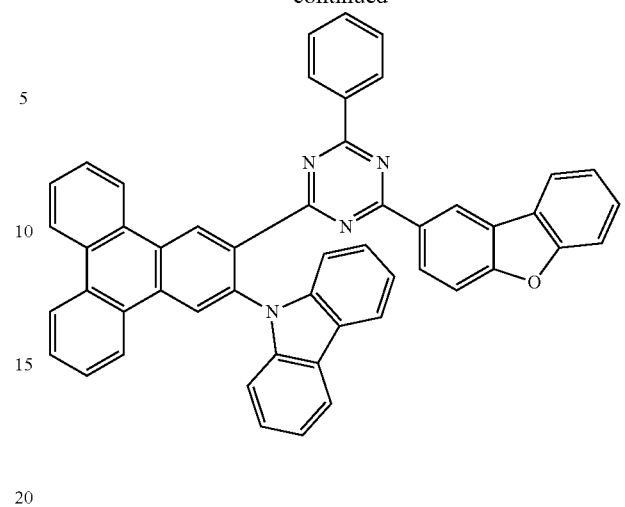
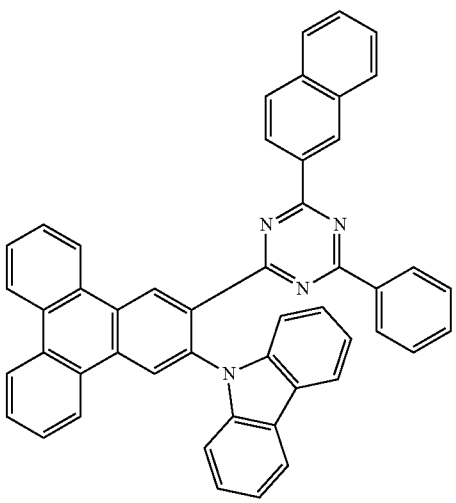
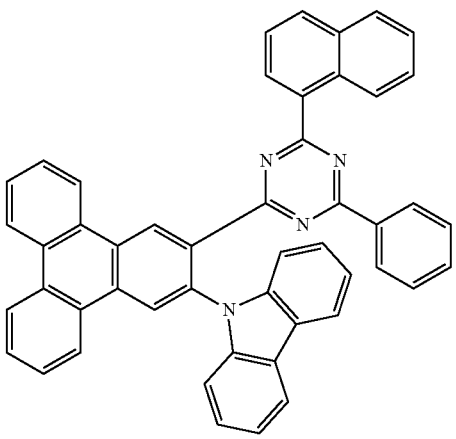

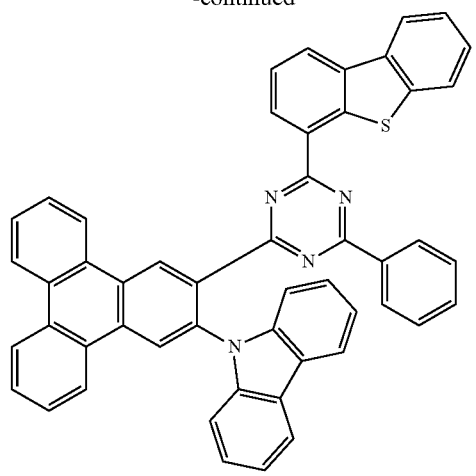
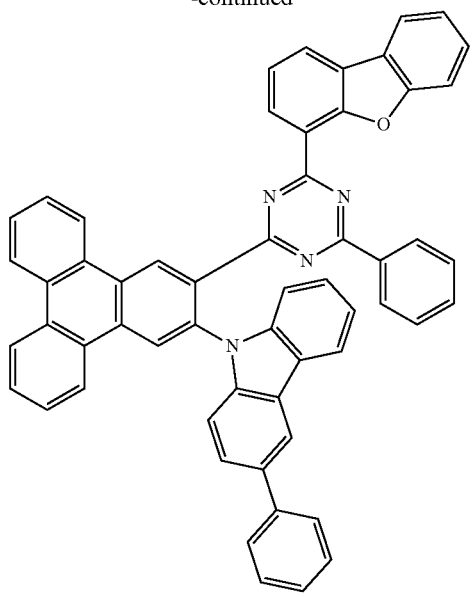
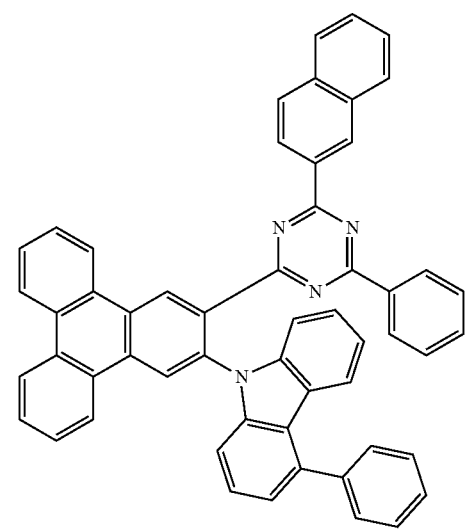
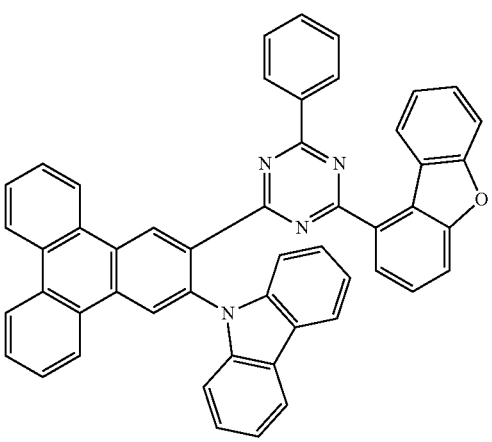
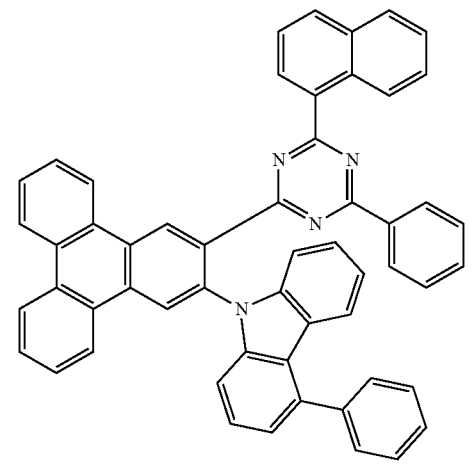
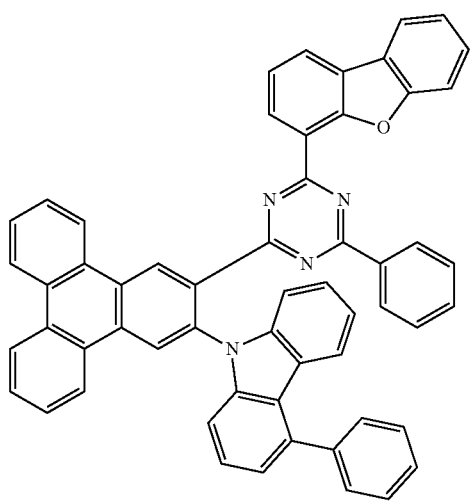

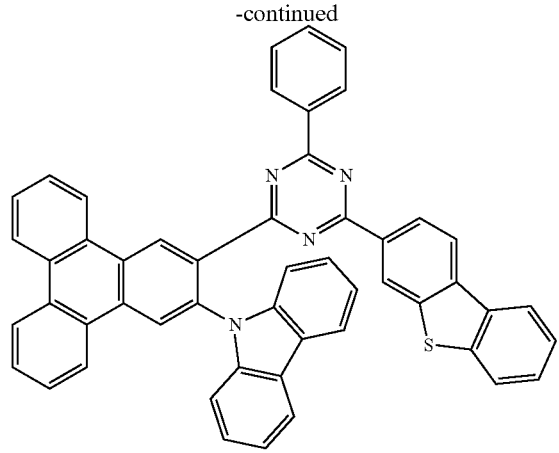
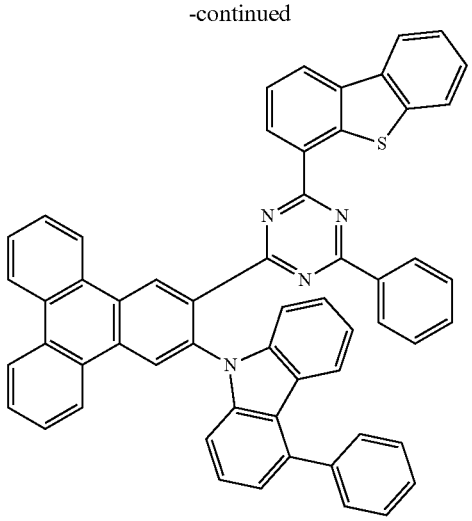
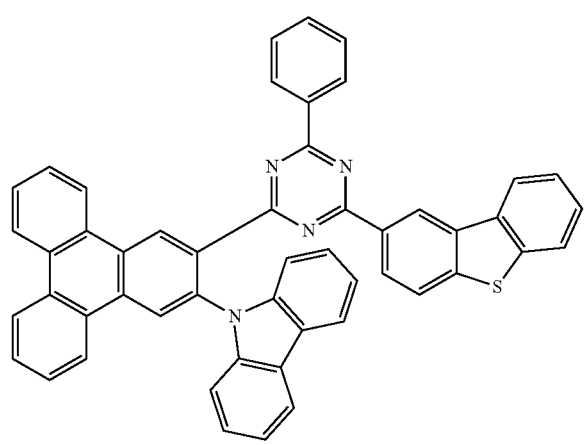
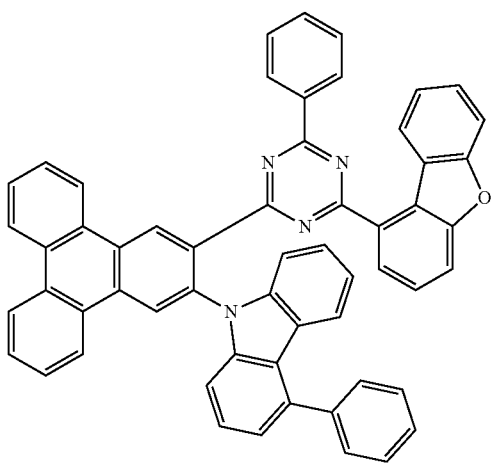
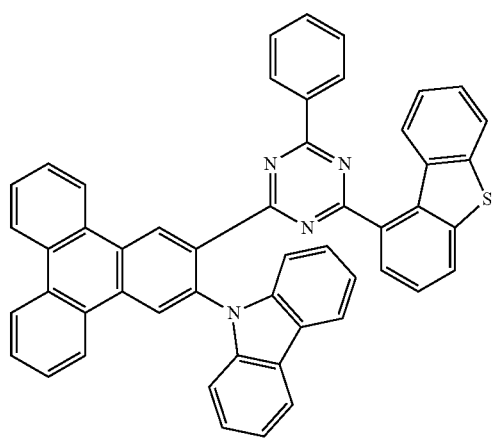
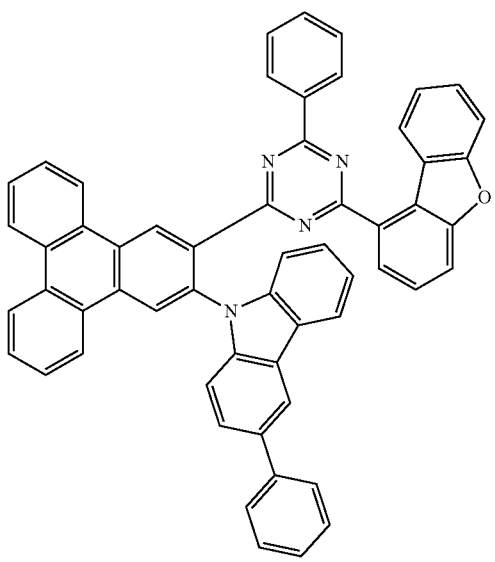

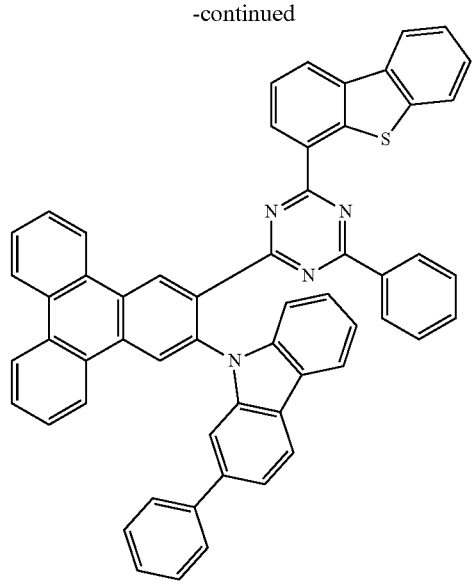
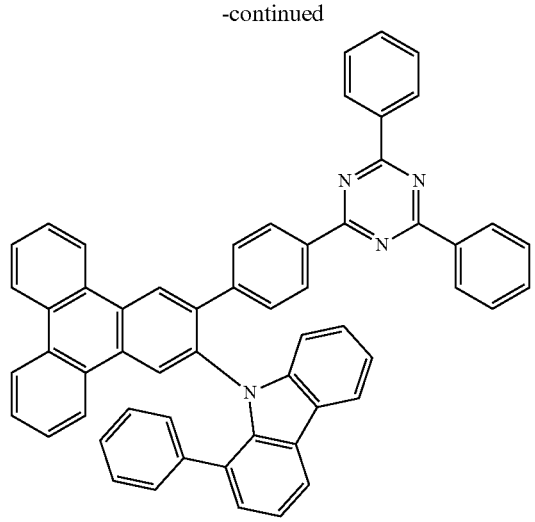
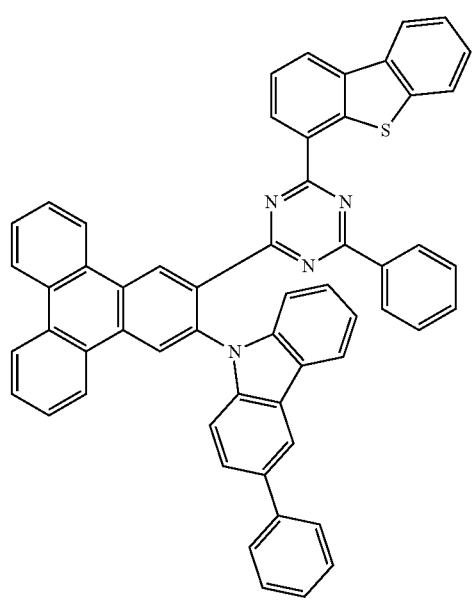
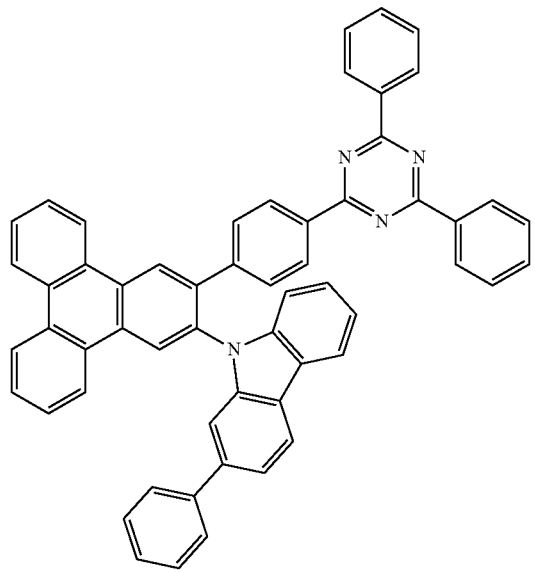
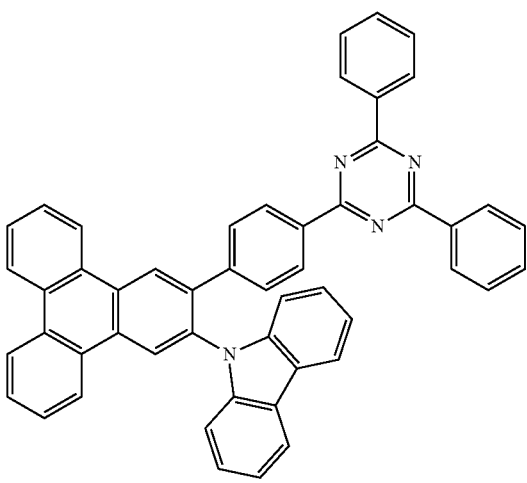
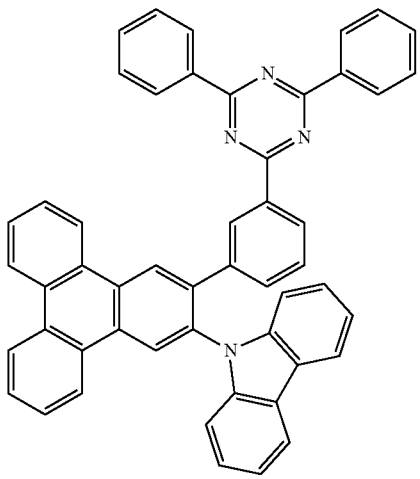

27
-continued
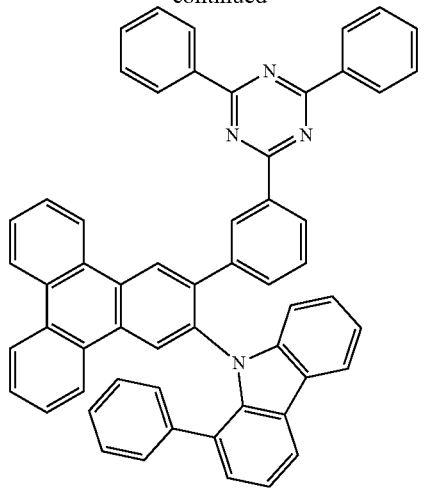
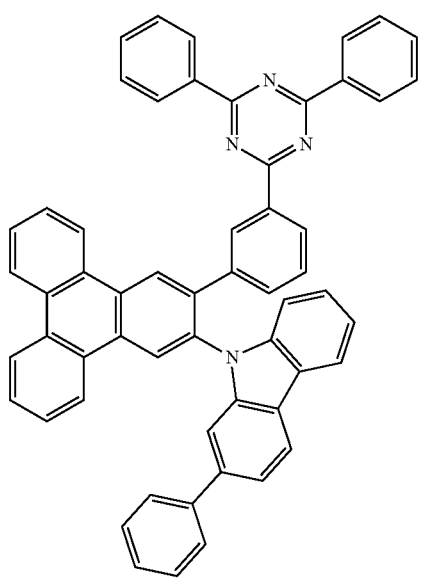
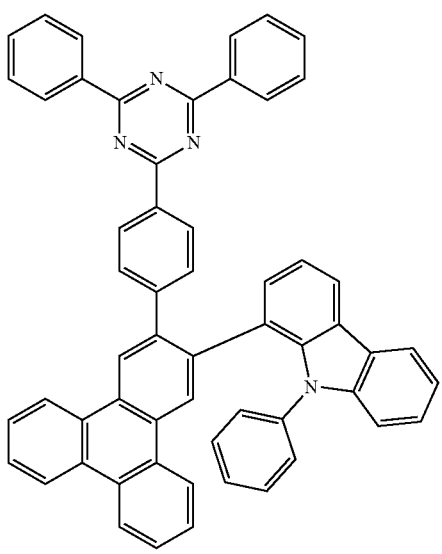
28
-continued
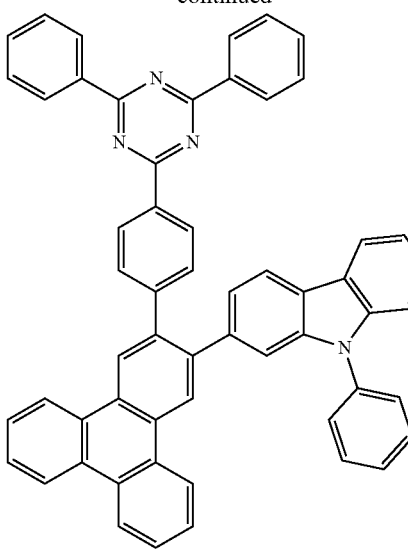
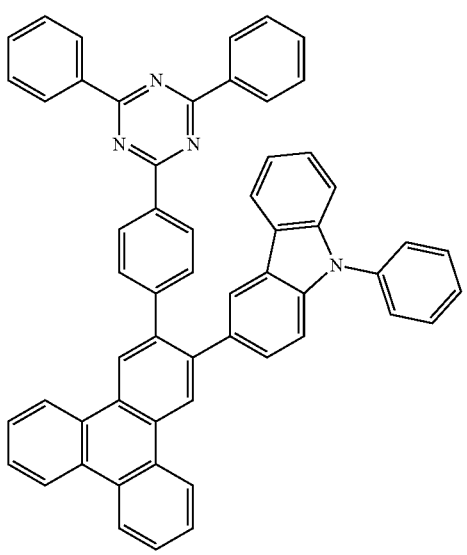
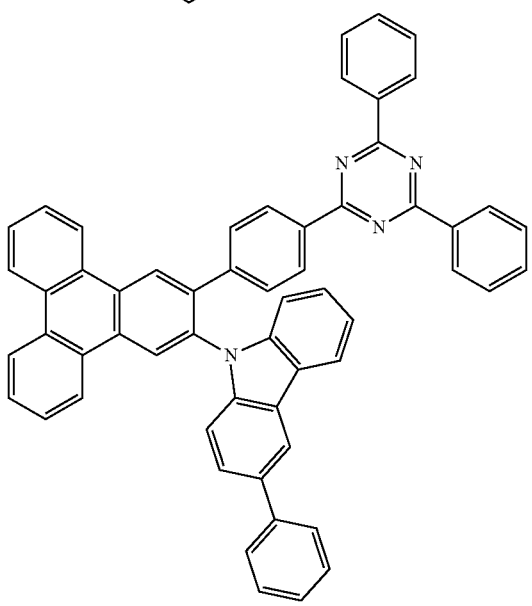

-continued
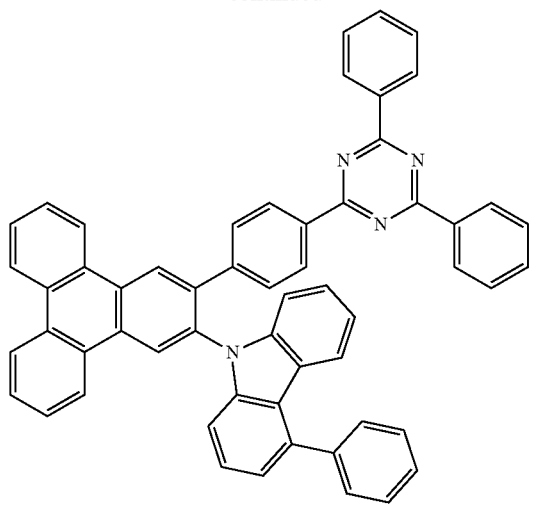
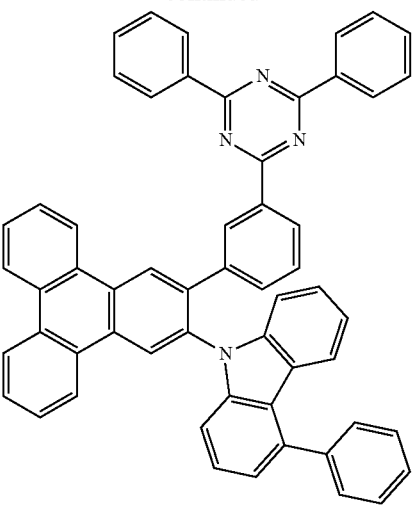
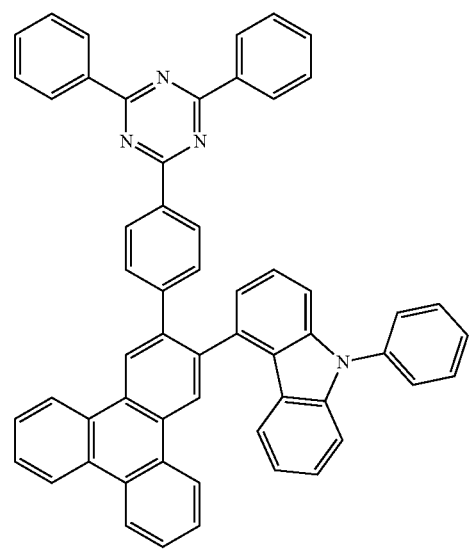
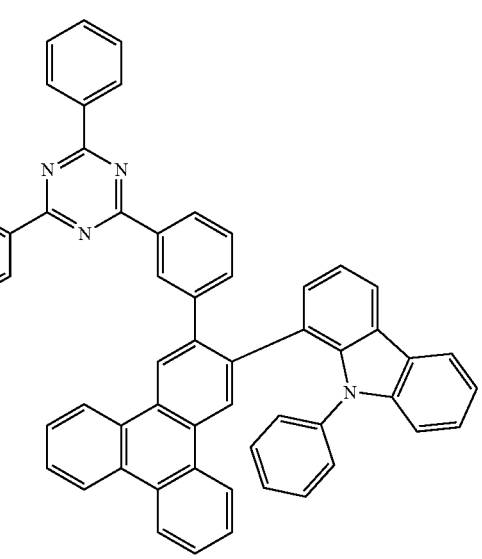
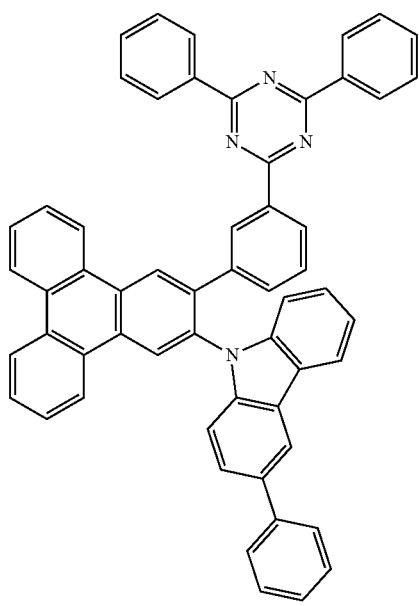
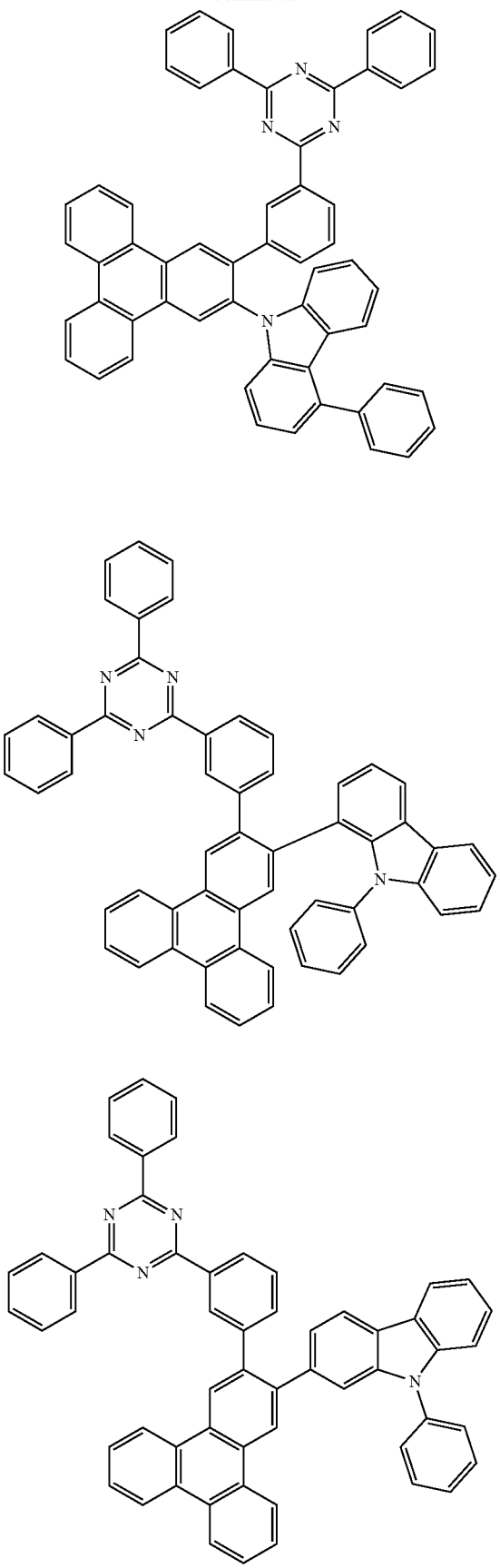

31
-continued
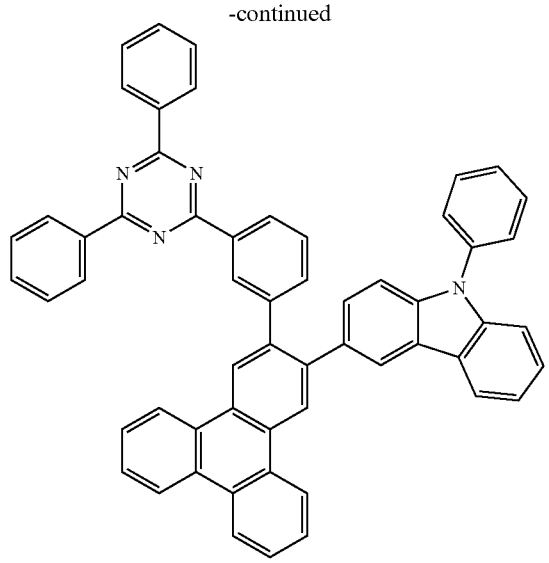
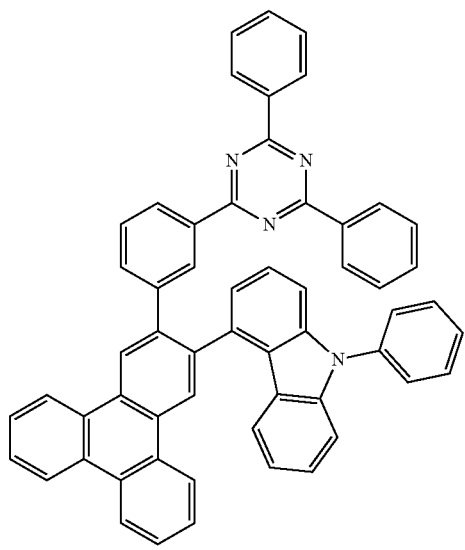
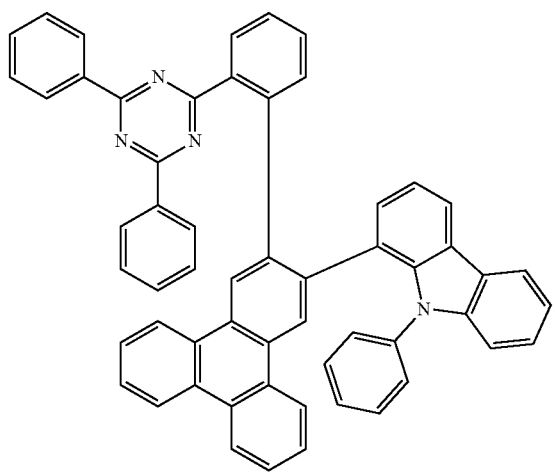
32
-continued
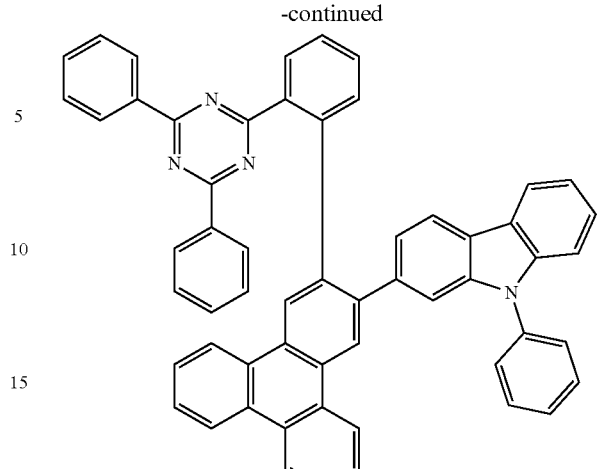
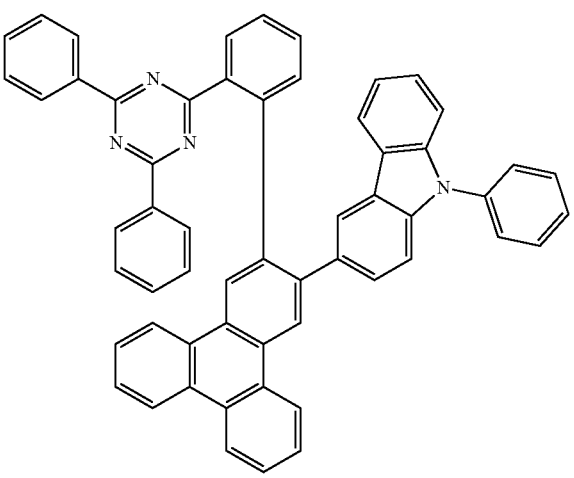
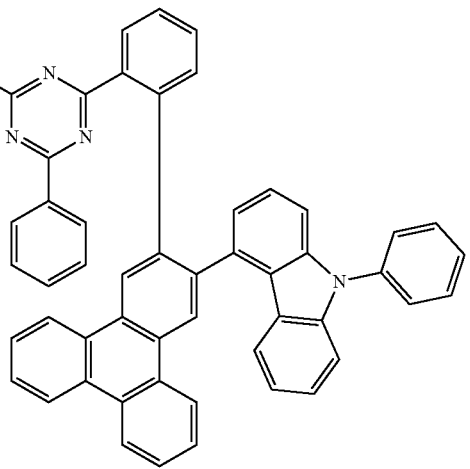

33
-continued
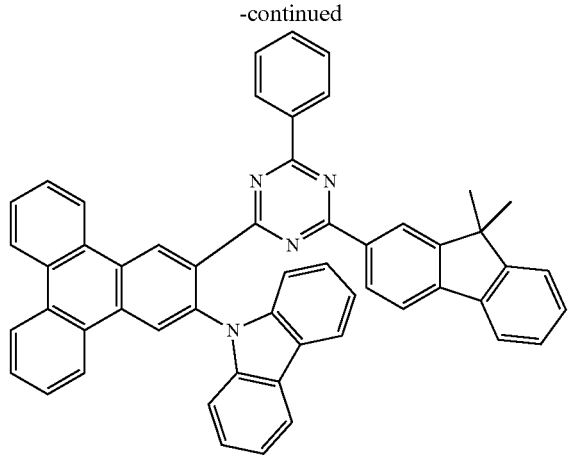
34
-continued
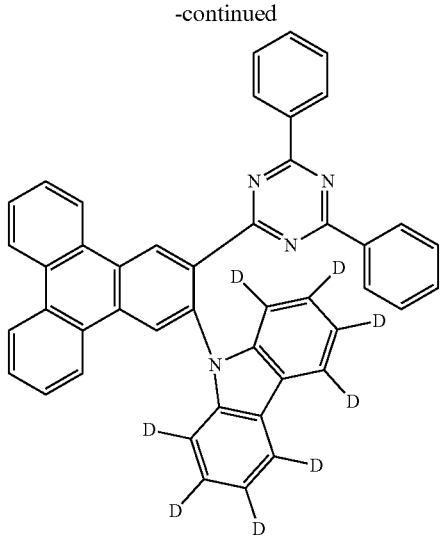
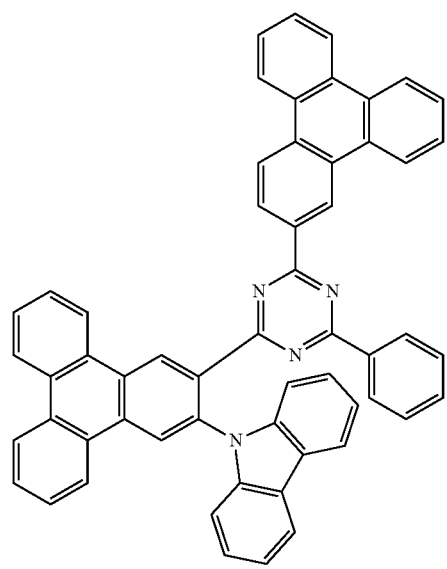
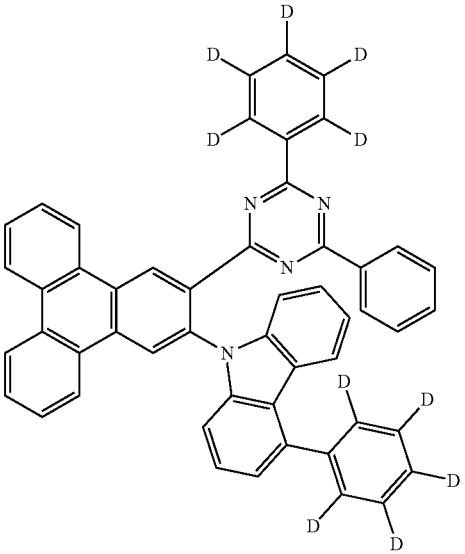
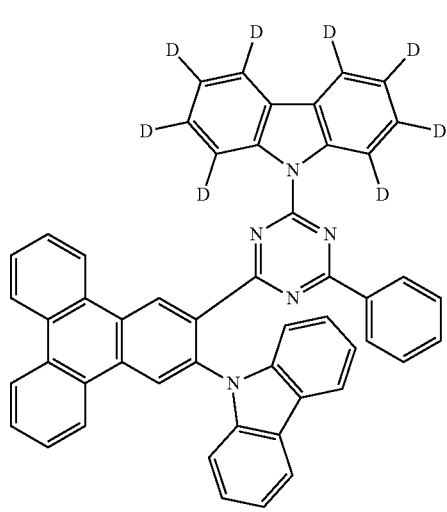
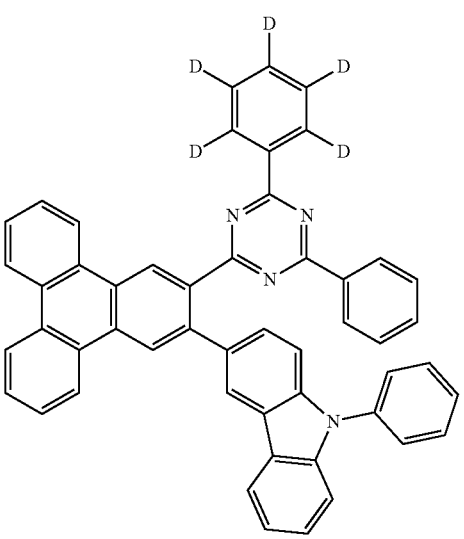

35
-continued
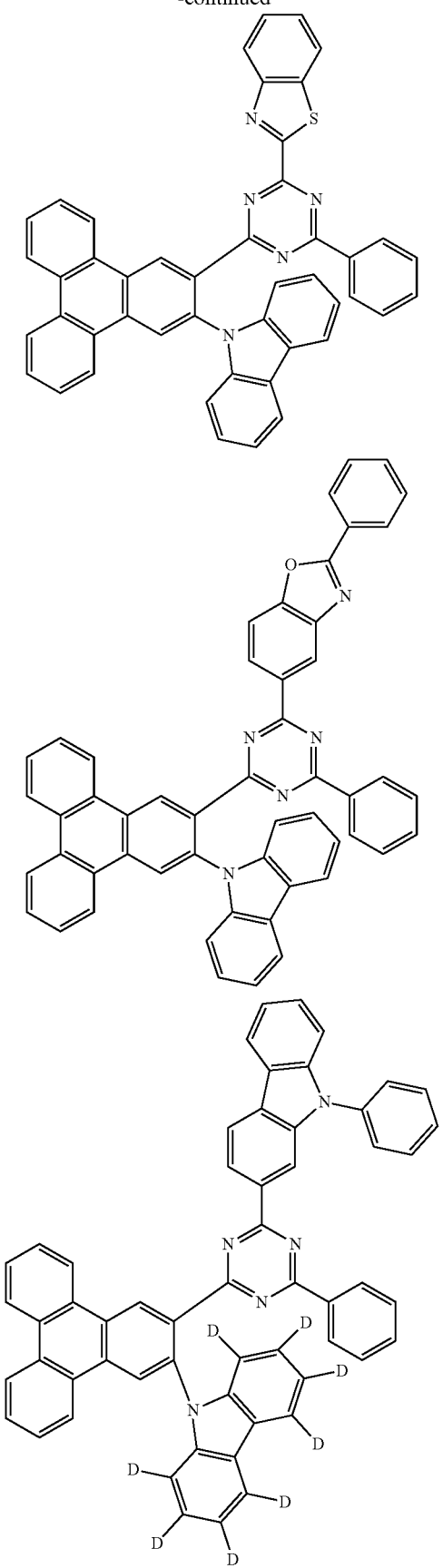
36
-continued
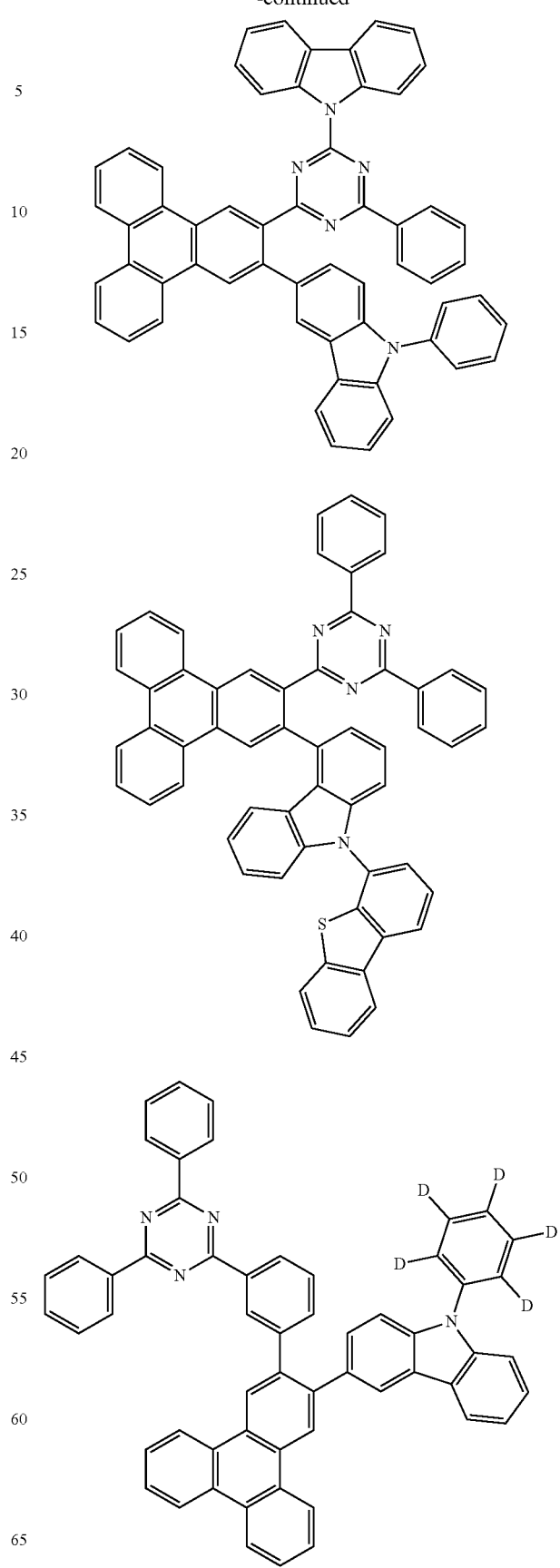

-continued
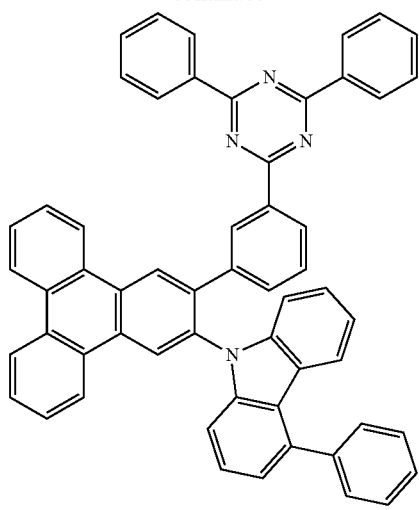
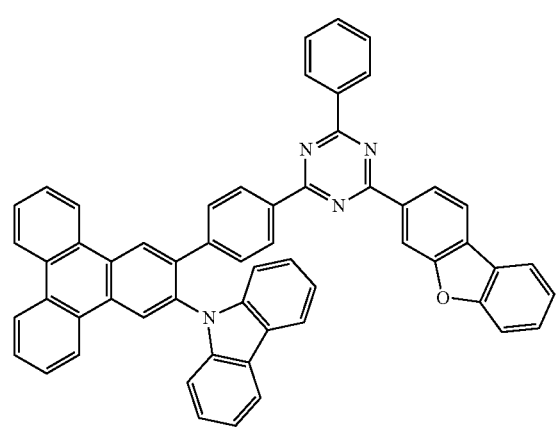
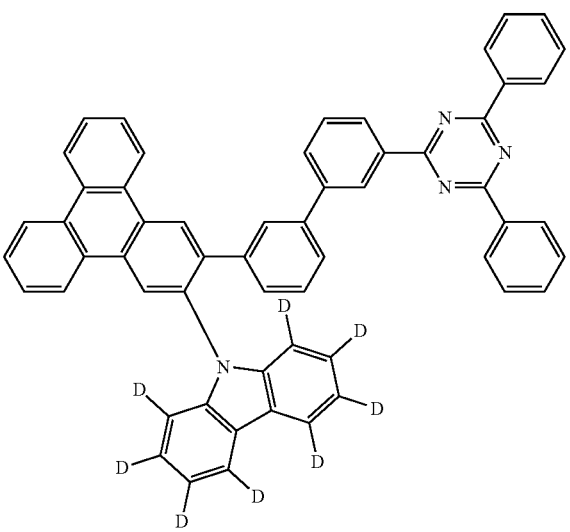
-continued
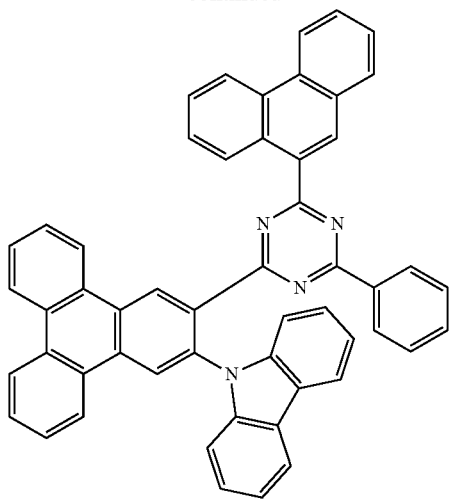
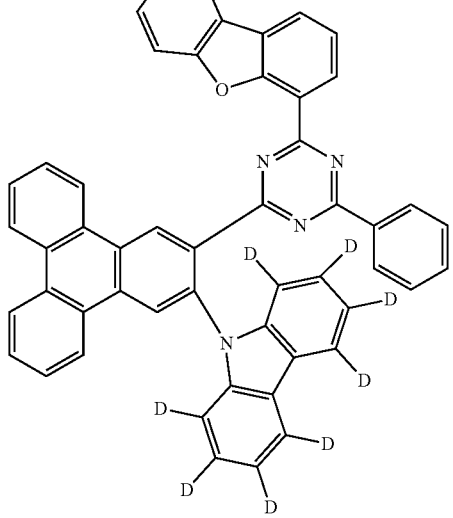
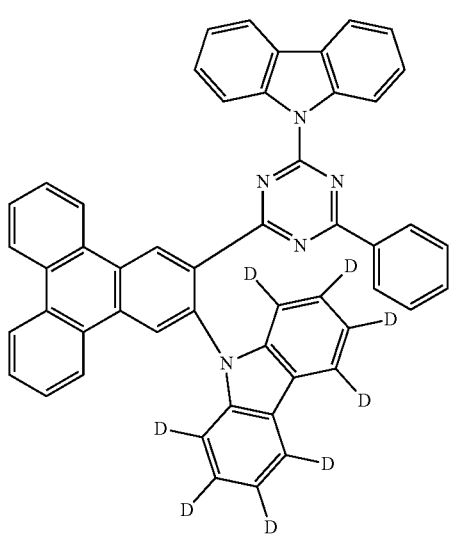

-continued
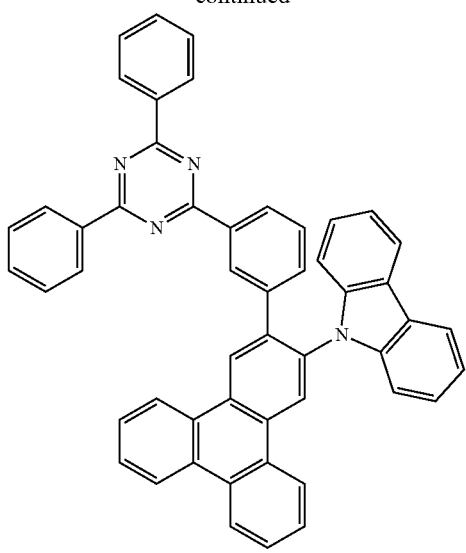
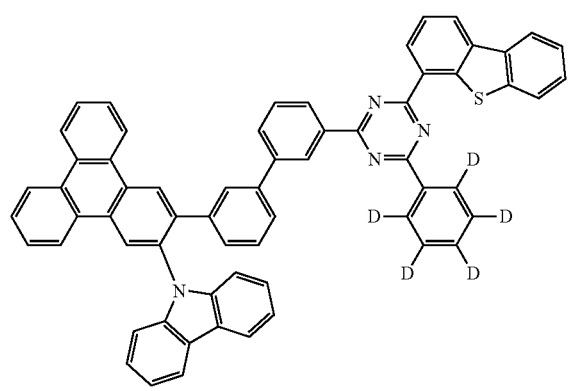
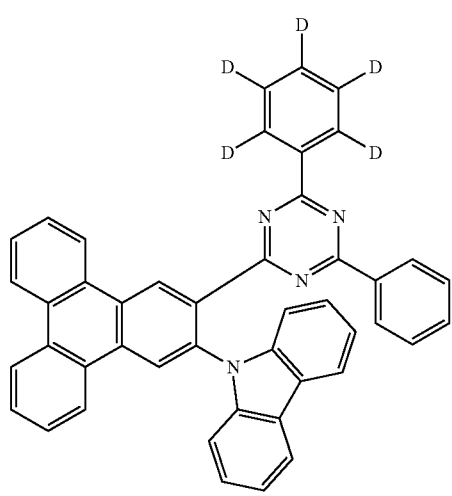
-continued
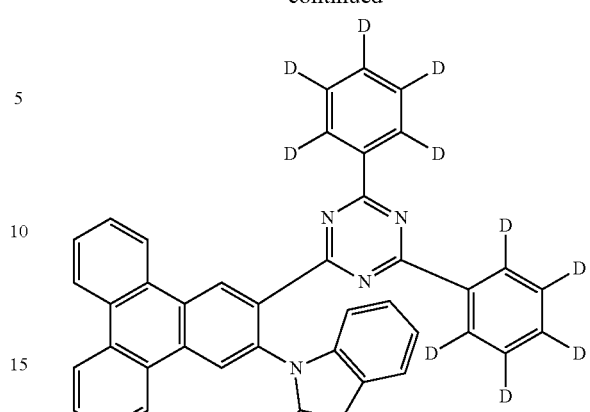
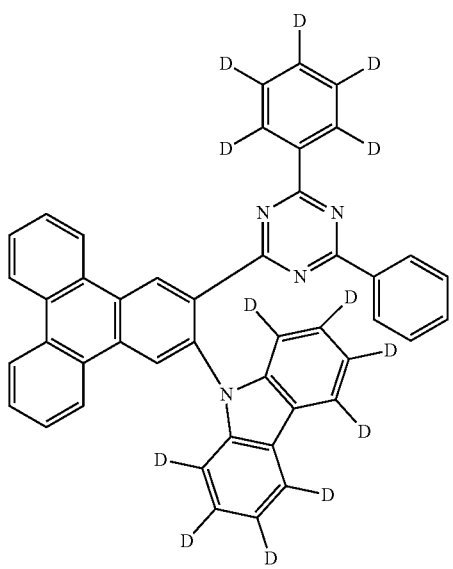

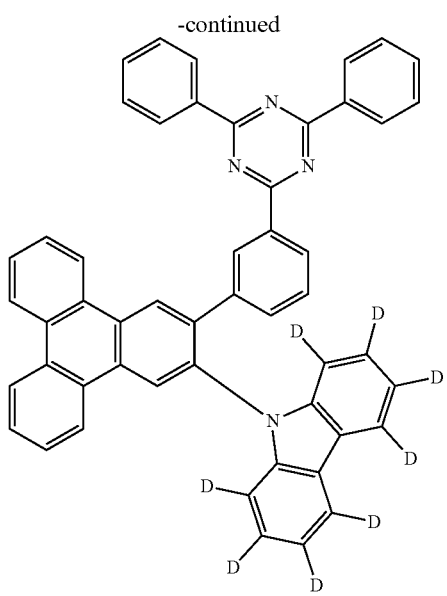

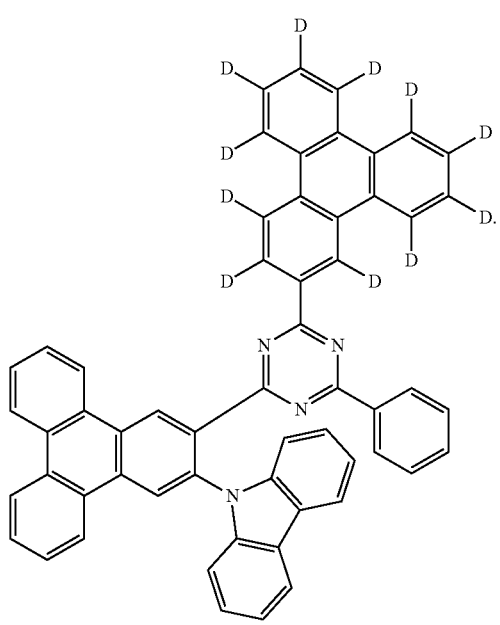

Since the compound represented by Formula 1 has a triphenylene structure, it is possible to exhibit excellent heat resistance. Because the carbazole-based group having hole transfer characteristics and the triazine-based group (pyridine, pyrimidine, and triazine) having electron transport characteristics are adjacent to each other in an ortho position, intra charge transfer can be easily performed. Therefore, the stability of the molecule is high, and it is advantageous for both hole and electron transport. In addition, various aryl groups and heterocycles are additionally substituted in $Ar_1$ and $Ar_2$ of Chemical Formula 1, so that electron transport properties can be variously controlled, which is advantageous for balancing charges according to changes in the common layer.

Therefore, the organic light emitting device using the same can have high efficiency, a low driving voltage, a long lifetime, and the like.

The compound represented by Chemical Formula 1 is prepared according to the preparation method as shown in Reaction Scheme A-1 and Reaction Scheme A-2.

[Reaction Scheme A-1]

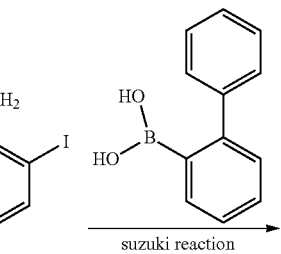

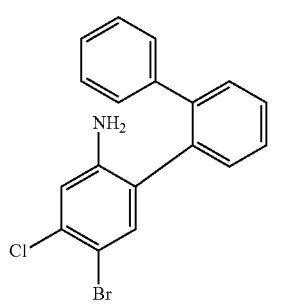

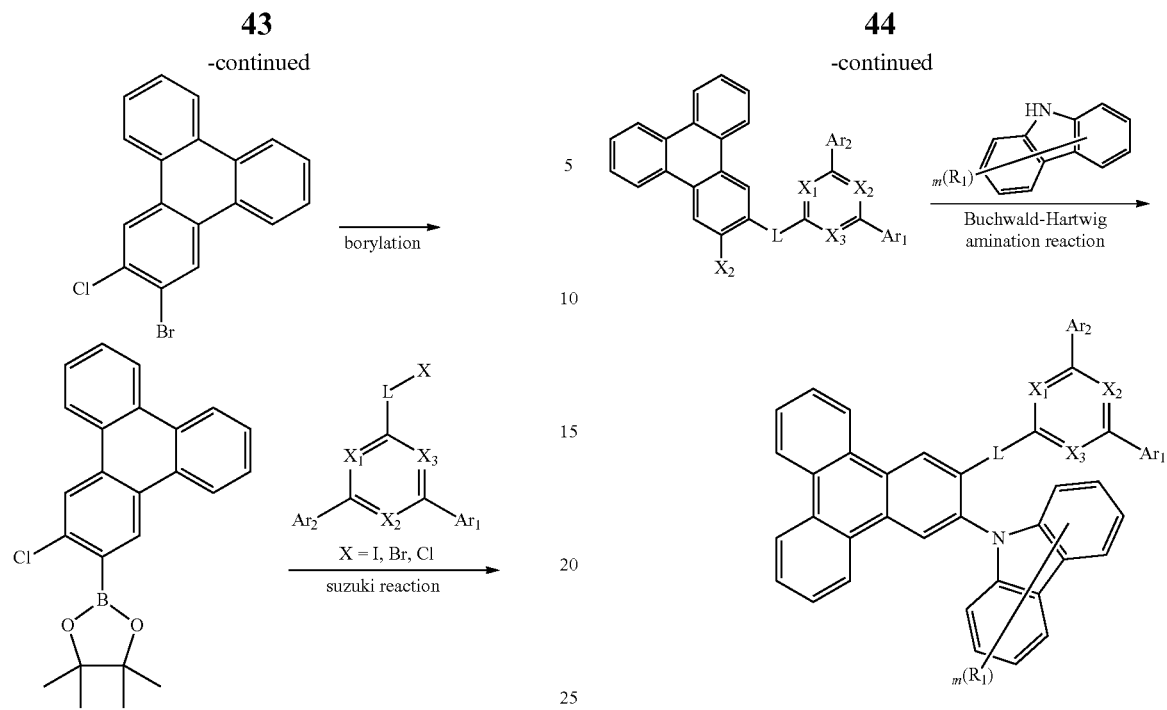
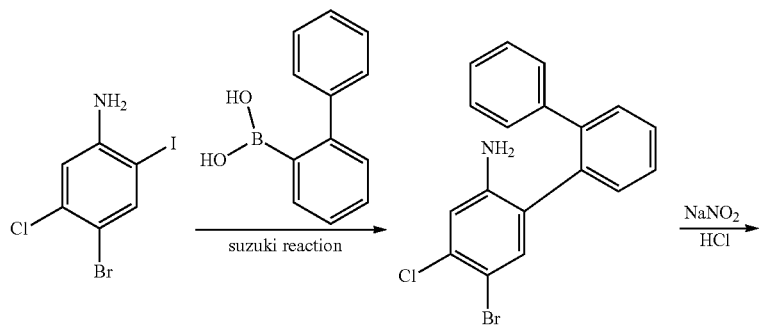
[Reaction Scheme A-2]
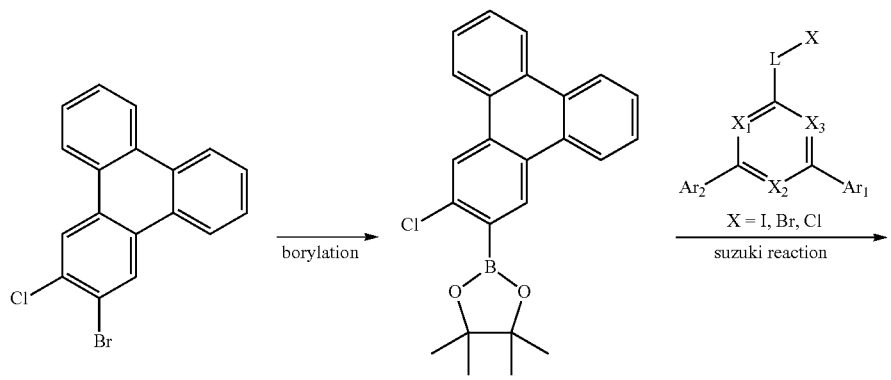

-continued

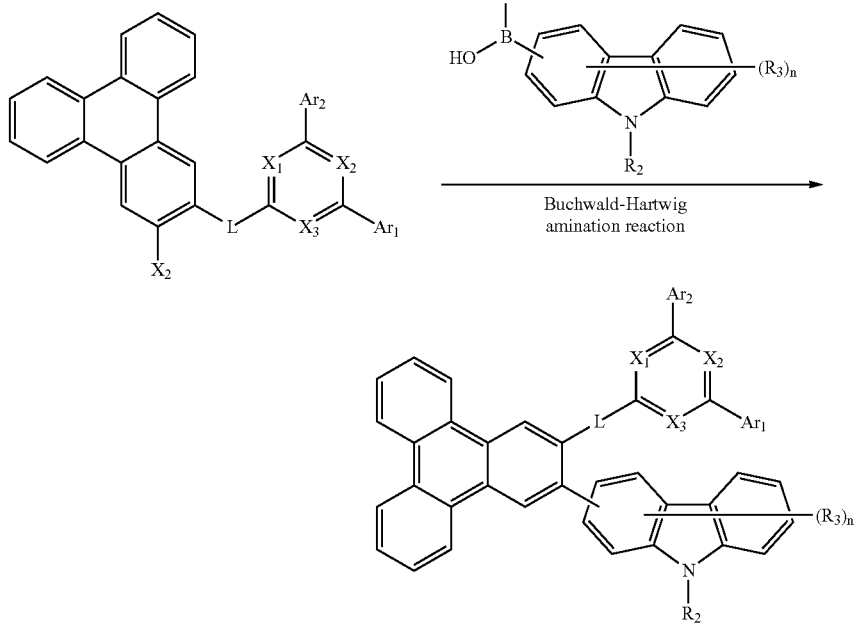

In Reaction Scheme A-1 and A-2, the remaining definitions excluding X are as defined above, and X1 is a halogen, for example bromo, chloro, or iodo.

Reaction Scheme A-1 and A-2 are a Suzuki coupling reaction and an amine substitution reaction. These reactions are preferably carried out in the presence of a palladium catalyst and a base. The type of the reactive group and the catalyst used in the above reaction scheme can be appropriately changed. The above preparation method can be further specified in preparation examples described hereinafter.

Organic Light Emitting Device

The present disclosure provides an organic light emitting device including the compound represented by Formula 1. In one example, the present disclosure provides an organic light emitting device including: a first electrode; a second electrode provided to face the first electrode; and at least one layer of organic material layers provided between the first electrode and the second electrode, wherein the at least one layer of the organic material layers includes a compound represented by Formula 1.

The organic material layer of the organic light emitting device of the present disclosure may have a single layer structure, or it may have a multilayered structure in which two or more organic material layers are stacked. For example, the organic light emitting device of the present disclosure may have a structure including a hole injection layer, a hole transport layer, an electron inhibition layer, a light emitting layer, an electron transport layer, an electron injection layer, and the like as the organic material layer. However, the structure of the organic light emitting device is not limited thereto, and it may include a smaller number of organic layers.

Further, the organic material layer may include a hole injection layer, a hole transport layer, or a layer simultaneously performing hole injection and transport, wherein the hole injection layer, the hole transport layer, and the layer simultaneously performing hole injection and transport include a compound represented by Formula 1.

Further, The organic material layer may include an electron inhibition layer, wherein the electron inhibition layer includes a compound represented by Formula 1.

Further, the organic material layer may include a light emitting layer, wherein the light emitting layer includes a compound represented by Formula 1.

Further, the organic material layer may include an electron transport layer or an electron injection layer, or a layer simultaneously performing electron transport and injection, wherein the electron transport layer, the electron injection layer, and the layer simultaneously performing electron transport and injection include a compound represented by Formula 1.

Further, the organic material layer may include a hole injection layer, a hole transport layer, an electron inhibition layer, and a light emitting layer, wherein any one or more selected from the group consisting of the hole injection layer, the hole transport layer, and the electron inhibition layer may include the compound represented by Chemical Formula 1.

Further, the organic light emitting device according to the present disclosure may be a normal type of organic light emitting device in which an anode, one or more organic material layers, and a cathode are sequentially stacked on a substrate. Further, the organic light emitting device according to the present disclosure may be an inverted type of organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 depicts an example of an organic light emitting device including a substrate 1, an anode 2, a light emitting layer 3, and a cathode 4. In such a structure, the compound represented by Chemical Formula 1 may be included in the light emitting layer.

FIG. 2 depicts an example of an organic light emitting device including a substrate 1, an anode 2, a hole injection layer 5, a hole transport layer 6, an electron inhibition layer 7, a light emitting layer 3, an electron transport layer 8, an electron injection layer 9, and a cathode 4. In such a structure, the compound represented by Chemical Formula 1 may be included in one or more layers of the hole injection layer, the hole transport layer, the electron inhibition layer, the light emitting layer, the hole blocking layer, and the electron injection and transport layer.

The organic light emitting device according to the present disclosure may be manufactured by materials and methods known in the art, except that at least one layer of the organic material layers includes the compound represented by Chemical Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer, and a second electrode on a substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming an organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer, and an anode material on a substrate.

In addition, the compound represented by Chemical Formula 1 may be formed into an organic layer by a solution coating method as well as a vacuum deposition method at the time of manufacturing an organic light emitting device. Herein, the solution coating method means spin coating, dip coating, doctor blading, inkjet printing, screen printing, a spray method, roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene] (PEDOT), polypyrrole, polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; and a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole-injecting effect to the light emitting layer or the light emitting material, prevents excitons produced in the light emitting layer from moving to a hole injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrilehexaazatriphenylene-based organic material, a quinacridone-based organic material, a perylene-based organic material, anthraquinone, a polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron inhibition layer is a layer provided between the hole transport layer and the light emitting layer in order to prevent the electrons injected in the cathode from being transferred to the hole transport layer without being recombined in the light emitting layer, which may also be referred to as an electron blocking layer. The electron inhibition layer is preferably a material having a smaller electron affinity than the electron transport layer.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole, and benzimidazole-based compound; a poly(p-phenylenevinylene) (PPV)-based polymer; a spiro compound; polyfluorene; rubrene; and the like, but are not limited thereto.

The light emitting layer may include a host material and a dopant material. The host material may be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic compounds include carbazole derivatives, dibenzofuran derivatives, furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, and examples thereof include pyrene, anthracene, chrysene, and periflanthene having the arylamino group, and the like, and the styrylamine compound is a compound where at least one arylvinyl group is substituted in substituted or unsubstituted arylamine. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples thereof include: an Al complex of 8-hydroxyquinoline; a complex including Alq3; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-napholato)aluminum, bis(2-methyl-8-quinolinato)(2-napholato)gallium, and the like, but are not limited thereto.

The organic light emitting device according to the present disclosure may be a front side emission type, a back side emission type, or a double side emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device containing the same will be described in detail in the following examples. However, these examples are presented for illustrative purposes only, and are not intended to limit the scope of the present disclosure.

PREPARATION EXAMPLES

Preparation Example 1: Preparation of Compound 1

Step 1) Preparation of Compound 1-a

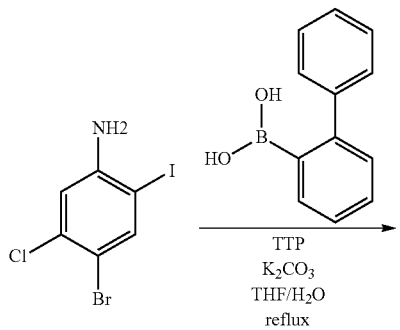

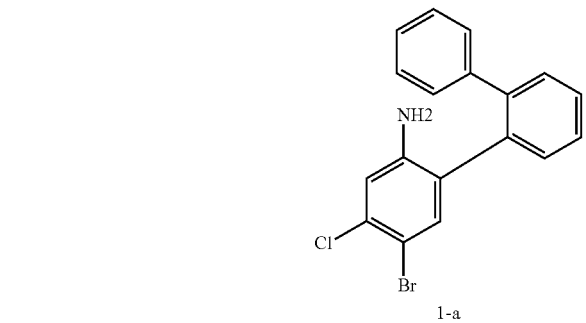

4-Bromo-5-chloro-2-iodoaniline (50 g, 150.4 mmol) and [1,1'-biphenyl]-2-yl-boronic acid (29.8 g, 150.4 mmol)) were added in 1000 mL of tetrahydrofuran, and then stirred and refluxed under a nitrogen atmosphere. Then, potassium carbonate (47.8 g, 451.3 mmol) was dissolved in 48 ml of water, and the aqueous solution was added thereto, and then sufficiently stirred. Then, tetrakis(triphenylphosphine)palladium (5.2 g, 4.5 mmol) was added thereto. After two hours of reaction, the reaction mixture was cooled to room temperature. The reaction mixture was separated into an organic layer and an aqueous layer, and then the organic layer was distilled. This was dissolved in 1079 ml of chloroform 20 times, and washed two times with water, then the organic layer was separated, removed, and dried over anhydrous magnesium sulfate, and distilled under reduced pressure. The concentrated material was recrystallized using a mixed solution of chloroform and hexane to produce a brown solid Compound 1-a (43.2 g, 80%, MS: $[M+H]^+$=359.7).

Step 2) Preparation of Compound 1-b

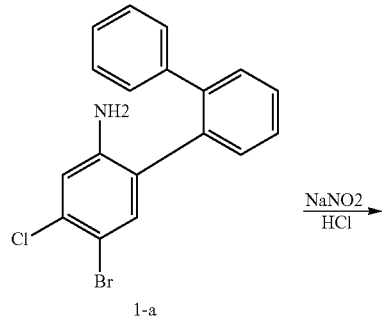

Compound 1-a (40 g, 111.5 mmol) was added in 700 mL of 2M hydrochloric acid, and then stirred for 15 minute at 0° C., and then sodium nitrite (8.5 g, 122.6 mmol) slowly added thereto. After one hour, the mixture was heated at 60° C. for 3 hours, and then the mixture was cooled to room temperature. The reaction mixture was separated into an organic layer and an aqueous layer, and then the organic layer was distilled. This was dissolved in 800 ml of chloroform 20 times, and washed two times with water, then the organic layer was separated, removed, and dried over anhydrous magnesium sulfate, and distilled under reduced pressure. The concentrated material was recrystallized using a mixed solution of chloroform and hexane to produce a brown solid Compound 1-b (27.4 g, 72%, MS: [M+H]$^+$=342.0).

Step 3) Preparation of Compound 1-c

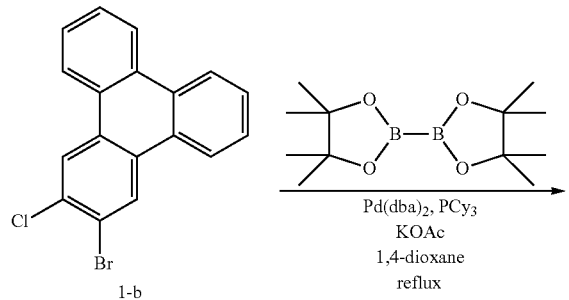

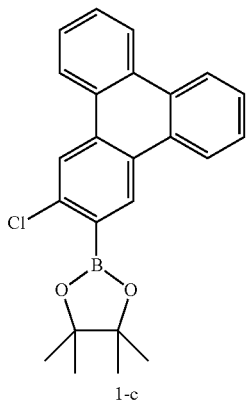

Compound 1-b (25 g, 73.3 mmol) and bis(pinacolato)diboron (18.6 g, 73.3 mmol) were added in 500 mL of 1,4-dioxane, and then stirred and refluxed under a nitrogen atmosphere. Then, potassium acetate (46.7 g, 219.9 mmol) was added thereto, and then sufficiently stirred. Then, dibenzylideneacetone palladium (1.3 g, 2.2 mmol) and tricyclohexylphosphine (1.2 g, 4.4 mmol) were added thereto. After three hours of reaction, the reaction mixture was cooled to room temperature and an organic layer was filtered to remove the base. The filtrated organic layer was distilled. This was dissolved in 285 ml of chloroform 10 times, and washed two times with water, then the organic layer was separated, removed, and dried over anhydrous magnesium sulfate, and distilled under reduced pressure. The concentrated material was recrystallized using a mixed solution of chloroform and hexane to produce a brown solid Compound 1-c (22.8 g, 80%, MS: [M+H]$^+$=389.7).

Step 4) Preparation of Compound 1-4

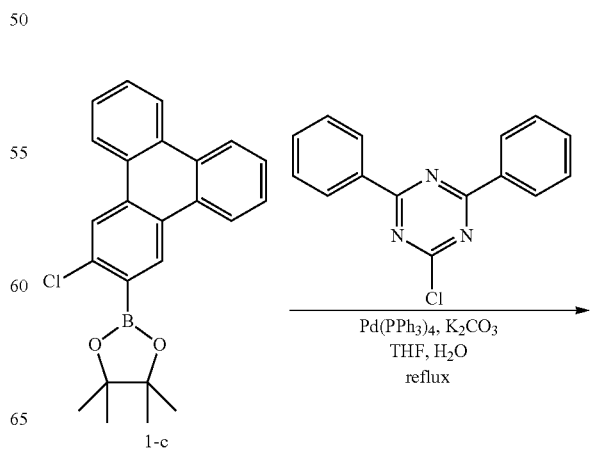

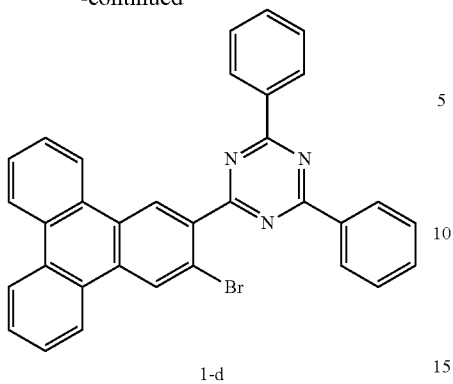

1-d

Compound 1-c (20 g, 51.5 mmol) and 2-chloro-4,6-diphenyl-1,3,5-triazine (13.8 g, 51.5 mmol) were added to 400 mL of tetrahydrofuran, and then stirred and refluxed under a nitrogen atmosphere. Then, potassium carbonate (16.4 g, 154.4 mmol) was dissolved in 16 ml of water, and the aqueous solution was added thereto, and then sufficiently stirred. Then, tetrakis(triphenylphosphine) palladium (1.8 g, 1.5 mmol) was added thereto. After one hour of reaction, the reaction mixture was cooled to room temperature. The reaction mixture was separated into an organic layer and an aqueous layer, and then the organic layer was distilled. This was dissolved in 554 ml of chloroform 20 times, and washed two times with water, then the organic layer was separated, removed, and dried over anhydrous magnesium sulfate, and distilled under reduced pressure. The concentrated material was recrystallized using a mixed solution of chloroform and ethyl acetate to produce a yellow solid Compound 1-d (19.1 g, 69%, MS: [M+H]$^+$=539.5).

Step 5) Preparation of Compound 1

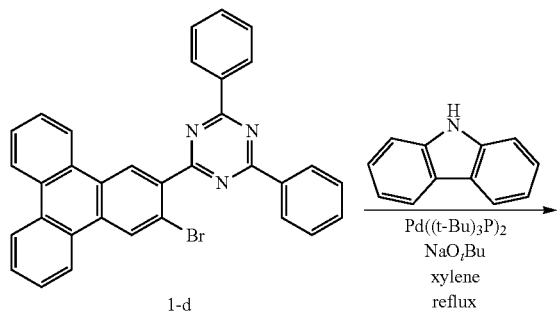

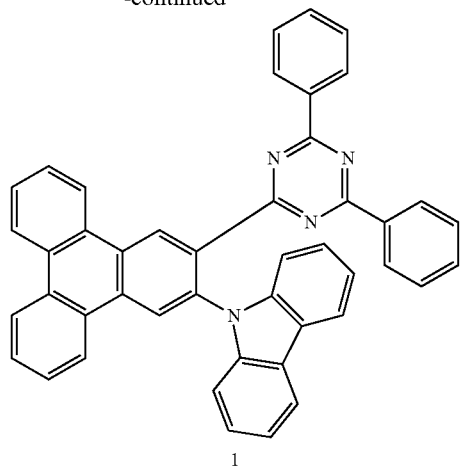

1

Compound 1-d (18 g, 33.4 mmol) and 9H-carbazol (5.6 g, 33.4 mmol) were added to 360 mL of xylene, and then stirred and refluxed under a nitrogen atmosphere. Then, sodium tert-butoxide (9.6 g, 100.3 mmol) was added thereto, and then sufficiently stirred. Then, bis(tri-tert-butylphosphine)palladium (0.5 g, 1 mmol) was added thereto. After one hour of reaction, the reaction mixture was cooled to room temperature and an organic layer was filtered to remove the base. The filtrated organic layer was distilled. This was dissolved in 209 ml of chloroform 10 times, and washed two times with water, then the organic layer was separated, removed, and dried over anhydrous magnesium sulfate, and distilled under reduced pressure. The concentrated material was recrystallized using a mixed solution of chloroform and ethyl acetate through a silica column to produce a yellow solid Compound 1 (13.2 g, 63%, MS: [M+H]$^+$=625.8).

Preparation Example 2: Preparation of Compound 2

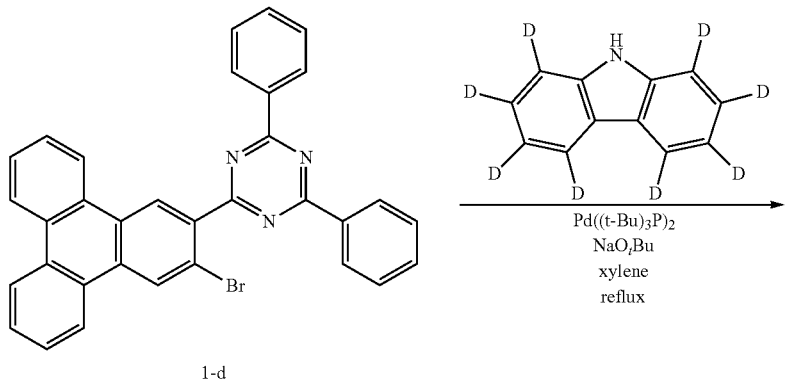

1-d

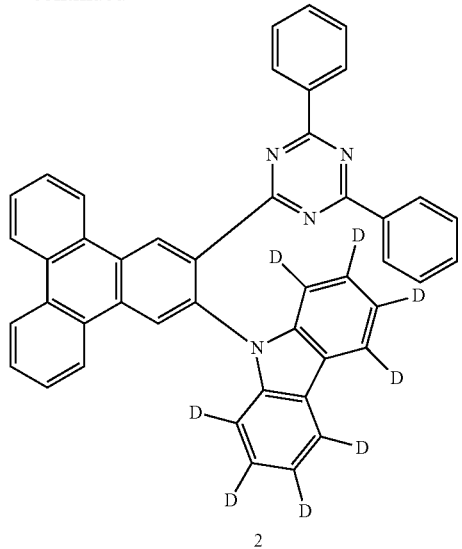

2

Compound 2 (MS: [M+H]$^+$=633.8) was prepared in the same manner as in the preparation of Compound 1, except that 9H-carbazole-1,2,3,4,5,6,7,8-d8 was used instead of 9H-carbazole.

Preparation Example 3: Preparation of Compound 3

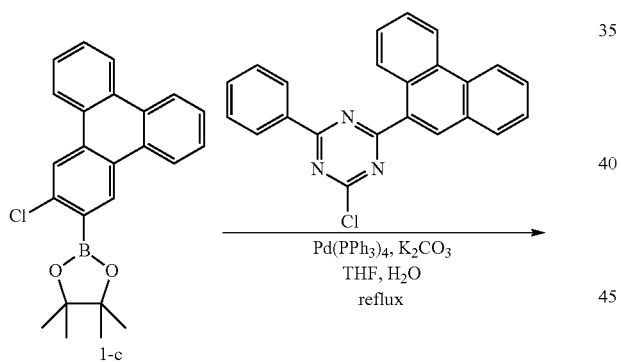

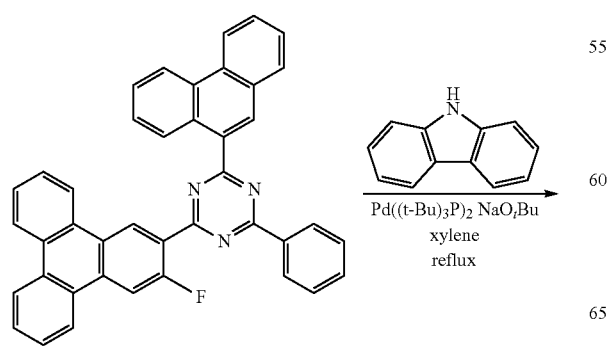

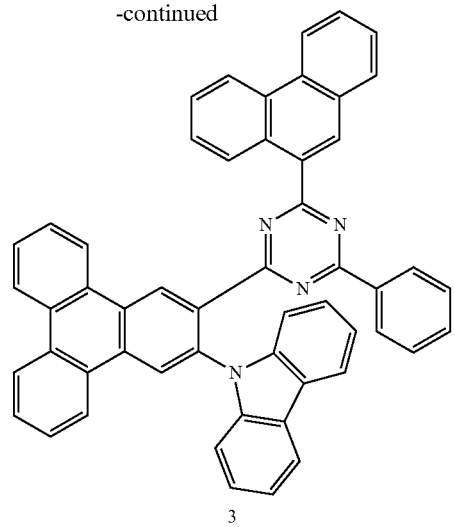

3

Compound 3 (MS: [M+H]$^+$=725) was prepared in the same manner as in the preparation 1, except that 2-chloro-4-(phenanthrene-9-yl)-6-phenyl-1,3,5-triazine was used instead of 2-chloro-4,6-diphenyl-1,3,5-triazine.

Preparation Example 4: Preparation of Compound 4

Preparation Example 5: Preparation of Compound 5

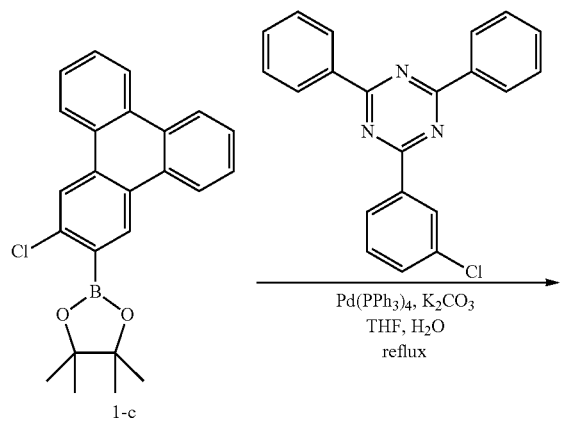

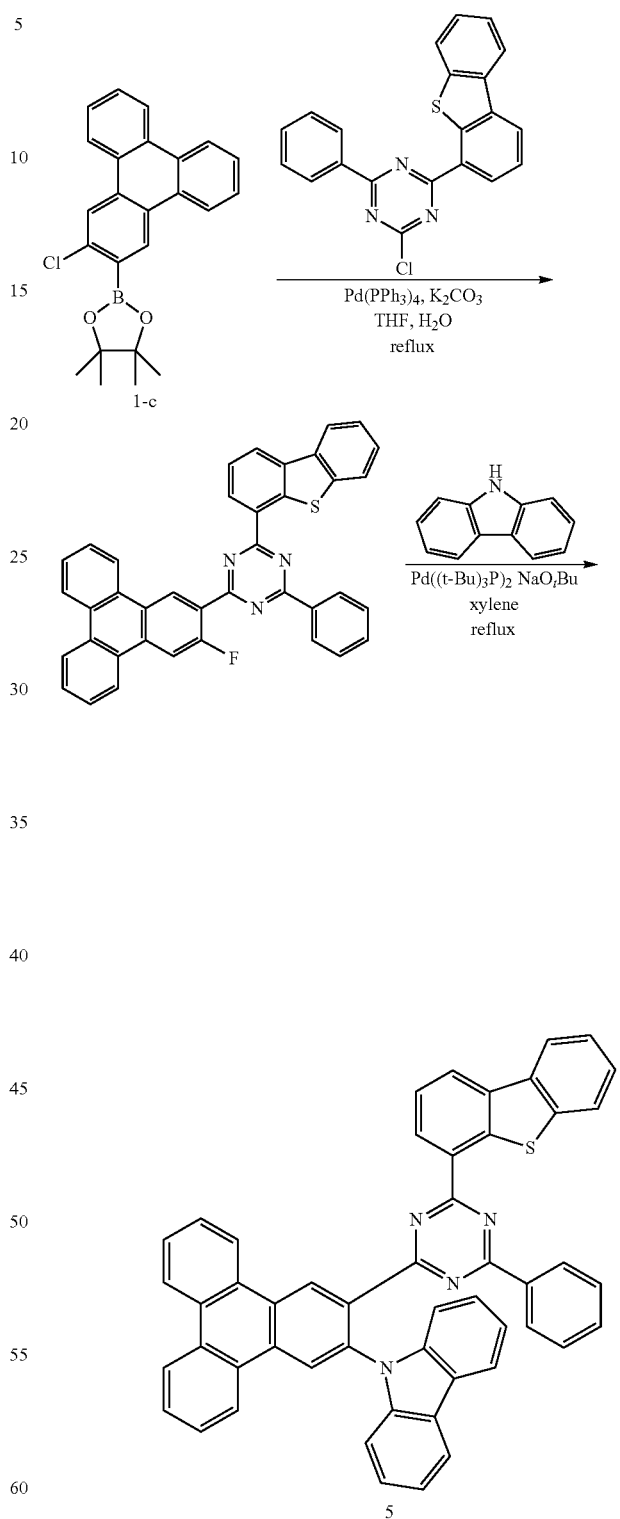

Compound 4 (MS: [M+H]⁺=701) was prepared in the same manner as in the preparation 1, except that 2-(3-chlorophenyl)-4,6-diphenyl-1,3,5-triazine was used instead of 2-chloro-4,6-diphenyl-1,3,5-triazine.

Compound 5 (MS: [M+H]⁺=731) was prepared in the same manner as in the preparation 1, except that 2-chloro-4-(dibenzo[b,d]thiophene-4-yl)-6-phenyl-1,3,5-trizine was used instead of 2-chloro-4,6-diphenyl-1,3,5-triazine.

Preparation Example 6: Preparation of Compound 6

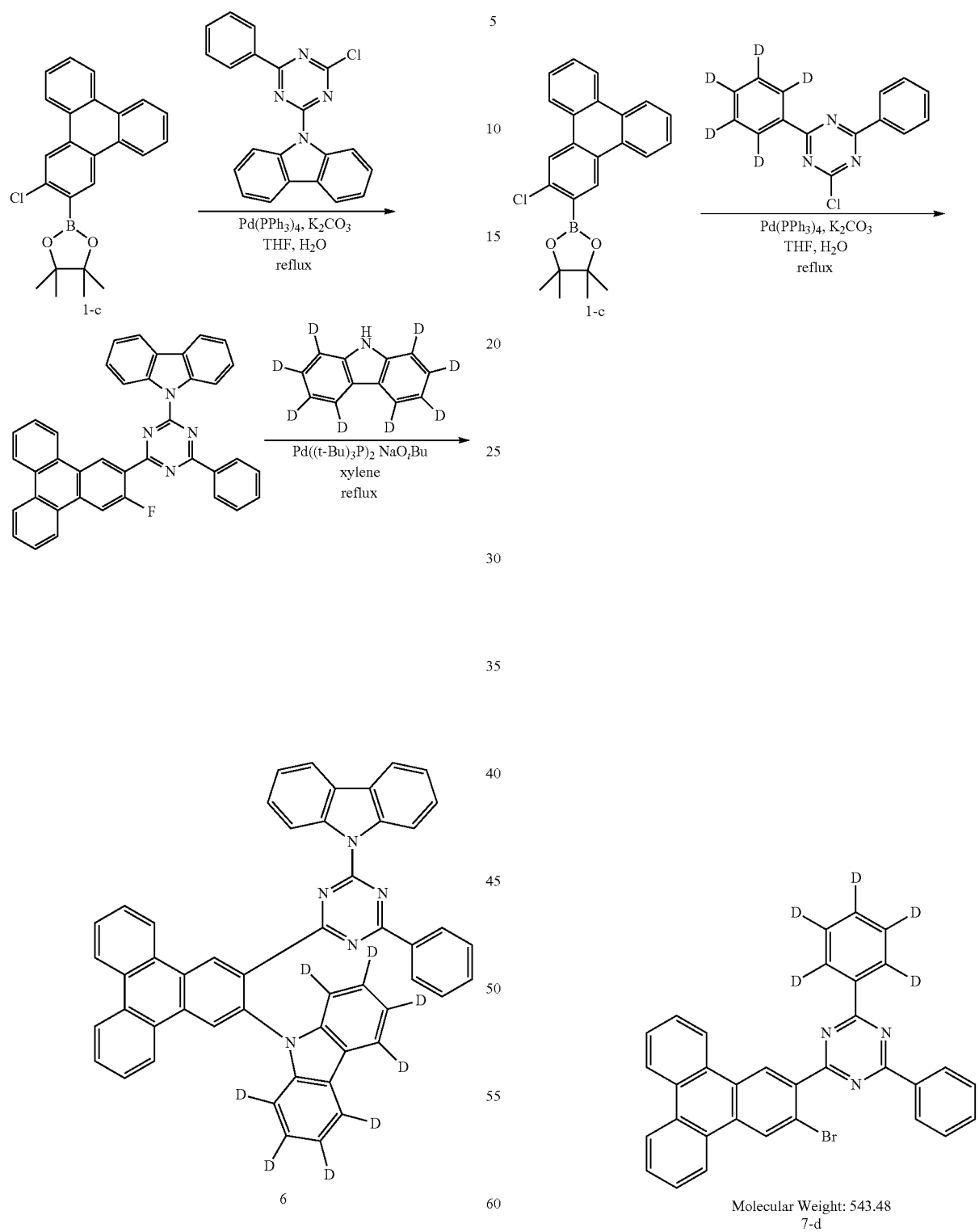

Compound 6 (MS: [M+H]⁺=722) was prepared in the same manner as in the preparation 1, except that 9H-carbazole-1,2,3,4,5,6,7,8-d8 was used instead of 9H-carbazole and 9-(4-chloro-6-phenyl-1,3,5-triazin-2-yl)-9H-carbazole was used instead of 2-chloro-4,6-diphenyl-1,3,5-triazine.

Preparation Example 7: Preparation of Compound 7

Step 1) Preparation of Compound 7-d

Compound 7-d (MS: [M+H]⁺=543) was prepared in the same manner as in the preparation 1, except that 2-chloro-4-phenyl-6-(phenyl-d5)-1,3,5-triazine was used instead of 2-chloro-4,6-diphenyl-1,3,5-triazine.

Step 2) Preparation of Compound 7

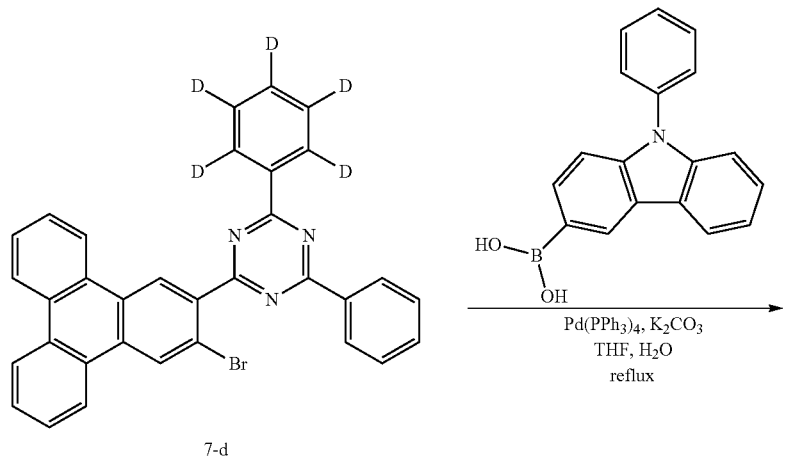

Compound 7-d (15 g, 27.6 mmol) and (9-phenyl-9H-carbazol-3-yl)boronic acid (7.9 g, 27.6 mmol) were added to 300 mL of tetrahydrofuran, and then stirred and refluxed under a nitrogen atmosphere. Then, sodium carbonate (8.8 g, 82.8 mmol) was dissolved in 9 ml of water, and the aqueous solution was added thereto, and then sufficiently stirred. Then, tetrakis(triphenylphosphine)palladium (1 g, 0.8 mmol) was added thereto. After one hour of reaction, the reaction mixture was cooled to room temperature and an organic layer was filtered. This was dissolved in 390 ml of chloroform 20 times, and washed two times with water, then the organic layer was separated, removed, and dried over anhydrous magnesium sulfate, and distilled under reduced pressure. The concentrated material was recrystallized using a mixed solution of chloroform and ethyl acetate to produce a white solid Compound 7 (10.9 g, 56%, MS: [M+H]+= 706.9).

Preparation Example 8: Preparation of Compound 8

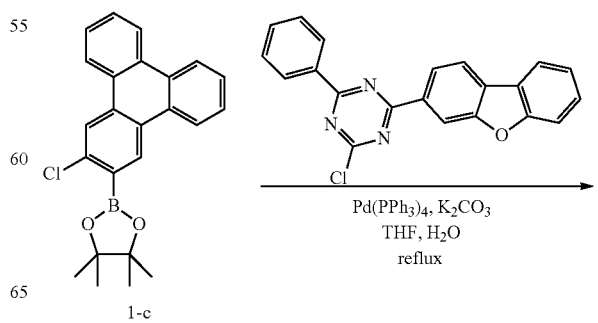

-continued

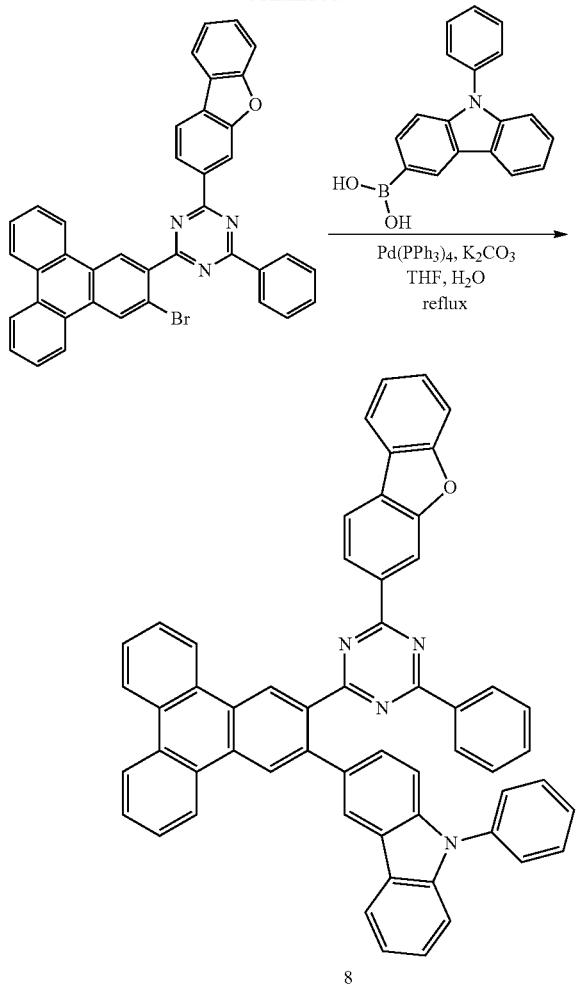

8

Compound 8 (MS: [M+H]$^+$=791) was prepared in the same manner as in the preparation 7, except that 2-chloro-4-(dibenzo[b,d]furane-3-yl)-6-phenyl-1,3,5-trizine was used instead of 2-chloro-4-phenyl-6-(phenyl-d5)-1,3,5-triazine.

EXAMPLES

Example 1

A glass substrate with a thin film of ITO (indium tin oxide) coated at a thickness of 1400 Å was put into distilled water containing a detergent dissolved therein and washed by ultrasonic waves. In this case, the detergent used was a product commercially available from Fisher Co., and the distilled water was one which had been filtered twice by using a filter that is commercially available from Millipore Co. The ITO was washed for 30 minutes, and ultrasonic washing was then repeated twice for 10 minutes by using distilled water. After the washing with distilled water was completed, the substrate was ultrasonically washed with a solvent of isopropyl alcohol, acetone, and methanol, and dried, after which it was transported to a plasma cleaner. Then, the substrate was cleaned with oxygen plasma for 5 minutes, and then transferred to a vacuum evaporator.

On the ITO transparent electrode thus prepared, the following compound HT-A and the following compound PD were thermally vacuum deposited at a ratio of 95:5 (molar ratio) to have a thickness of 100 Å, and then only the following compound HT-A was thermally vacuum deposited to have a thickness of 1150 Å, thereby forming a hole transport layer. The following compound HT-B was thermally vacuum-deposited on the hole transport layer to a thickness of 450 Å to form an electron inhibition (blocking) layer. Then, Compound 1 prepared above and the following compound GD were thermally vacuum deposited at a ratio of 85:15 (molar ratio) on the electron inhibition layer, to have a thickness of 400 Å, thereby forming a light-emitting layer. On the light-emitting layer, the following compound ET-A was thermally vacuum deposited to have a thickness of 50 Å, thereby forming a hole blocking layer. Then, on the hole blocking layer, the following compound ET-B and the following compound Liq were thermally vacuum deposited at a ratio of 2:1 (weight ratio) to have a thickness of 250 Å, and then LiF and magnesium were thermally vacuum deposited at a ratio of 1:1 (weight ratio) to have a thickness of 30 Å, thereby forming an electron transport and injection layer. On the electron injection layer, magnesium and silver were thermally vacuum deposited at a ratio of 1:4 (weight ratio) to have a thickness of 160 Å, thereby forming a cathode. The organic light emitting device was manufactured by following the above process.

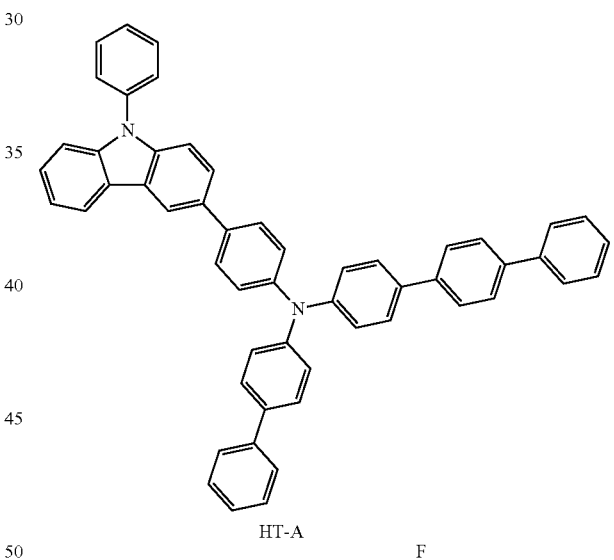

HT-A

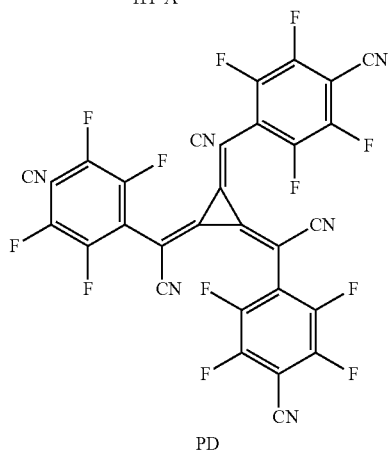

PD

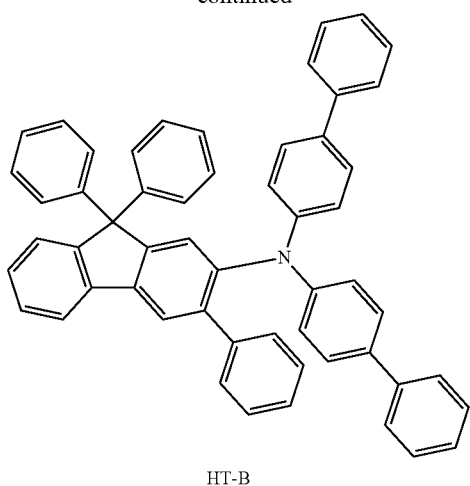

HT-B

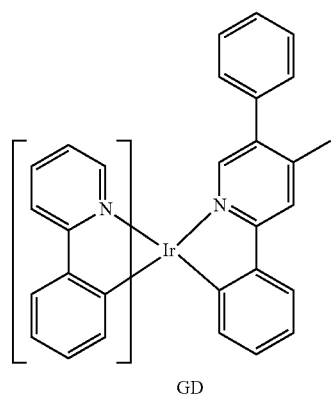

GD

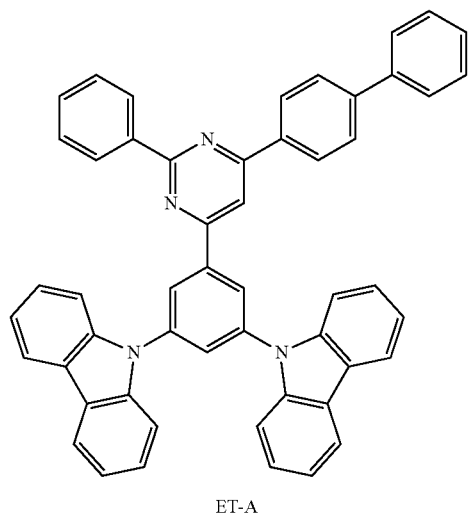

ET-A

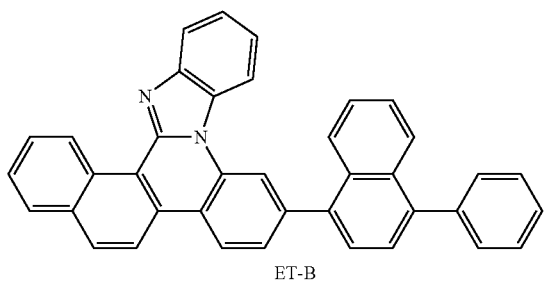

ET-B

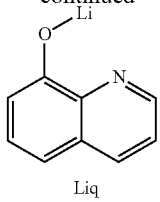

Liq

In the above process, the vapor deposition rate of the organic material was maintained at 0.4 to 0.7 Å/s, the lithium fluoride was deposited at 0.3 Å/s, the silver and magnesium were deposited at 0.2 Å/s, and the degree of vacuum during vapor deposition was maintained at $2 \times 10^{-7} \sim 5 \times 10^{-6}$ torr. The organic light emitting device was manufactured.

Examples 2 to 10 and Comparative Examples 1 to 4

The organic light emitting device was manufactured in the same manner as in Example 1, except that the compounds shown in Table 1 below was used instead of the compound 1.

For reference, in Examples 9 and 10 and Comparative Examples 3 and 4, an organic light emitting device was manufactured by using the compound shown in Table 1 below in a weight ratio of 1:1 instead of Compound 1. Taking Example 9 as an example, instead of Compound 1 in Example 1, Compound 1 and Compound H-2 were used in a weight ratio of 1:1. In Table 1, compounds H-2, C1, and C2 are as follows.

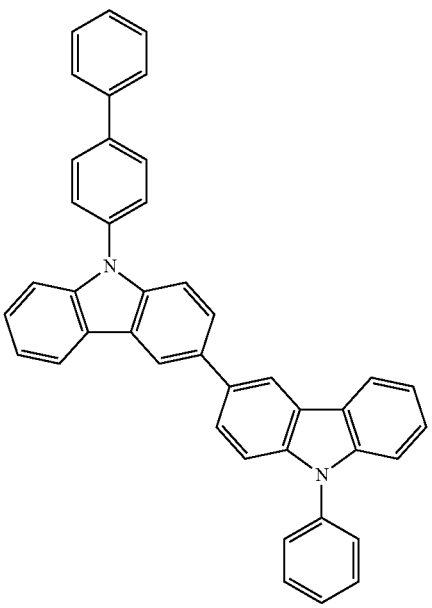

H-2

-continued

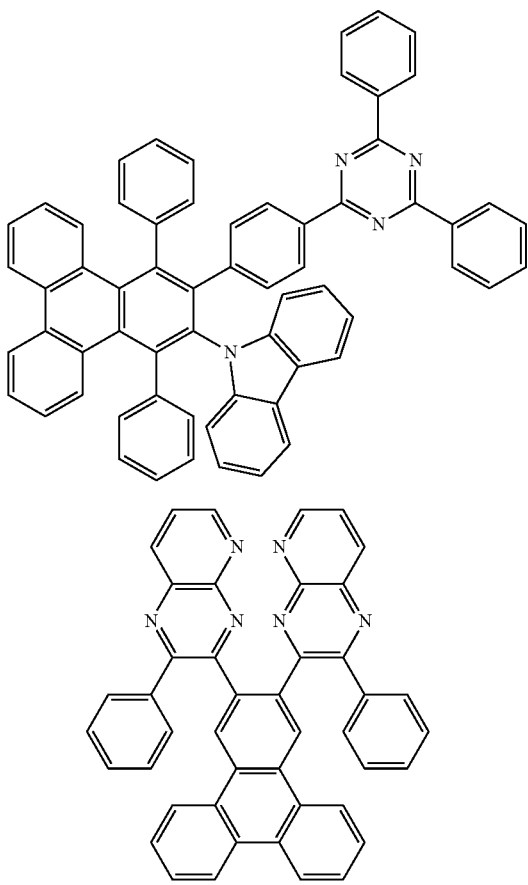

EXPERIMENTAL EXAMPLE

The driving voltage, efficiency, and lifetime were measured for the organic light emitting devices manufactured in the examples and comparative examples above, and the results are shown in Table 1 below. The driving voltage and efficiency were measured at a current density of 10 mA/cm². Further, in Table 1 below, T95 means the time required for the luminance to be reduced to 95% of the initial luminance at a current density of 20 mA/cm².

Examples 1 to 8 and Comparative Examples 1 and 2 were device examples using a single host in the light emitting layer. Since the carbazole-based group having hole transfer characteristics and the triazine-based group (pyridine, pyrimidine, and triazine) having electron transport characteristics are adjacent to each other in an ortho position in the compound of Chemical Formula 1, intra charge transfer can be easily performed. Therefore, the stability of the molecule is high, and the compound is advantageous for both hole and electron transport. In addition, various aryl groups and heterocycles are additionally substituted on Ar1 and Ar2 of Chemical Formula 1, such that electron transport properties can be variously controlled, and thus the compound is advantageous for balancing charges according to changes in the common layer.

Examples 9 and 10 are device examples using two types of hosts in the light emitting layer. Even when two types of hosts are used in the light emitting layer, it can be seen that the devices of Examples 9 and 10 using the compounds of the present disclosure have higher efficiencies than the devices of Comparative Examples 3 and 4, and in particular, have significantly improved life characteristics.

Therefore, as shown in Table 1, when the compound of Formula 1 is used as a host for an organic light emitting device, it can be confirmed that characteristics of low voltage, high efficiency, and long life time are exhibited.

DESCRIPTION OF REFERENCE NUMERALS

| 1: substrate | 2: anode |
|---|---|
| 3: light emitting layer | 4: cathode |
| 5: hole injection layer | 6: hole transport layer |
| 7: electron inhibition layer | 8: electron transport layer |
| 9: electron injection layer | |

TABLE 1

| Category | Light emitting layer compound | Voltage (V) (@10 mA/cm²) | Efficiency(cd/A) (@10 mA/cm²) | Emission color | T95 (@20 mA/cm²) |
|---|---|---|---|---|---|
| Example 1 | Compound 1 | 3.01 | 65.9 | green | 77 |
| Example 2 | Compound 2 | 3.00 | 65.8 | green | 87 |
| Example 3 | Compound 3 | 3.06 | 66.6 | green | 75 |
| Example 4 | Compound 4 | 2.97 | 67.2 | green | 72 |
| Example 5 | Compound 5 | 3.00 | 66.3 | green | 76 |
| Example 6 | Compound 6 | 3.06 | 66.1 | green | 99 |
| Example 7 | Compound 7 | 3.02 | 65.0 | green | 70 |
| Example 8 | Compound 8 | 2.98 | 65.9 | green | 75 |
| Example 9 | Compound 1, Compound H-2 | 3.11 | 70.0 | green | 85 |
| Example 10 | Compound 8, Compound H-2 | 3.17 | 72.5 | green | 80 |
| Comparative Example 1 | Compound C1 | 3.05 | 67.1 | green | 60 |
| Comparative Example 2 | Compound C2 | 3.06 | 66.0 | green | 57 |
| Comparative Example 3 | Compound C1, Compound H-2 | 3.12 | 78.5 | green | 76 |
| Comparative Example 4 | Compound C2, Compound H-2 | 3.20 | 79.2 | green | 70 |

The invention claimed is:
1. A compound represented by Chemical Formula 1:

[Chemical Formula 1]

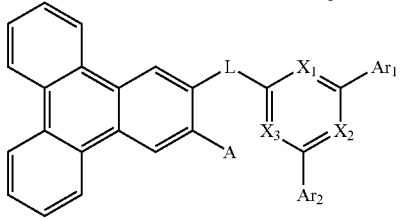

wherein, in Chemical Formula 1,
L is a direct bond, or a substituted or unsubstituted $C_{6-60}$ arylene,
A is a substituted or unsubstituted carbazolyl,
$X_1$, $X_2$, and $X_3$ are each independently N or CH, and at least one of $X_1$, $X_2$, and $X_3$ is N, and
$Ar_1$ and $Ar_2$ are each independently a substituted or unsubstituted $C_{6-60}$ aryl, or a substituted or unsubstituted $C_{5-60}$ heteroaryl containing one to three heteroatoms selected from the group consisting of N, O and S.

2. The compound of claim 1,
wherein the compound is represented by Formulas 2 or 3:

[Chemical Formula 2]

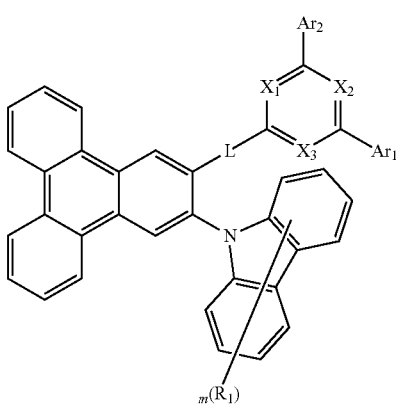

[Chemical Formula 3]

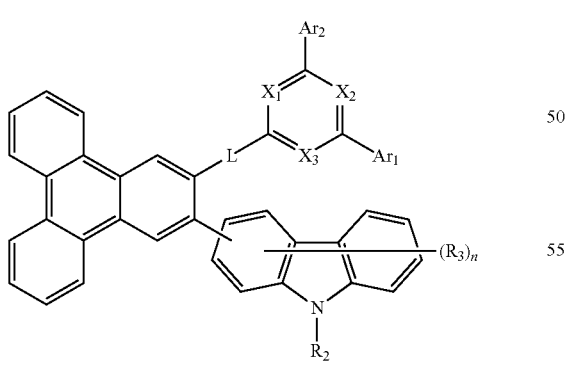

L, $X_1$, $X_2$, $X_3$, $Ar_1$, and $Ar_2$ are the same as defined in claim 1,
$R_1$ are each independently hydrogen, deuterium, a substituted or unsubstituted $C_{1-60}$ alkyl, a substituted or unsubstituted $C_{6-60}$ aryl, or a substituted or unsubstituted $C_{5-60}$ heteroaryl containing at least one heteroatom selected from the group consisting of N, O, and S,
$R_2$ is a substituted or unsubstituted $C_{1-60}$ alkyl, or a substituted or unsubstituted $C_{6-60}$ aryl,
$R_3$ are each independently hydrogen, deuterium, a substituted or unsubstituted $C_{1-60}$ alkyl, a substituted or unsubstituted $C_{6-60}$ aryl, or a substituted or unsubstituted $C_{5-60}$ heteroaryl containing at least one heteroatom selected from the group consisting of N, O, and S,
m is an integer of 0 to 8, and
n is an integer of 0 to 7.

3. The compound of claim 1,
wherein all of $X_1$, $X_2$, and $X_3$ are N.

4. The compound of claim 1,
wherein L is a direct bond, phenylene unsubstituted or substituted by at least one deuterium, or biphenylylene unsubstituted or substituted by at least one deuterium.

5. The compound of claim 1,
wherein $Ar_1$ and $Ar_2$ are each independently phenyl, biphenylyl, terphenylyl, dimethylfluorenyl, naphthyl, phenanthrenyl, triphenylenyl, dibenzofuranyl, dibenzothiophenyl, carbazol-9-yl, 9-phenyl-9H-carbazolyl, benzoxazolyl, benzothiazolyl, 2-phenylbenzoxazolyl, or 2-phenyl benzothiazolyl,
which are each independently unsubstituted or substituted by deuterium .

6. The compound of claim 2,
wherein $R_1$ are each independently hydrogen, deuterium, phenyl unsubstituted or substituted by at least one deuterium, dibenzofuranyl unsubstituted or substituted by at least one deuterium, dibenzothiophenyl unsubstituted or substituted by at least one deuterium, or carbazolyl unsubstituted or substituted by at least one deuterium.

7. The compound of claim 2,
wherein $R_2$ are each independently phenyl unsubstituted or substituted by at least one deuterium.

8. The compound of claim 2,
wherein $R_3$ are each independently hydrogen, deuterium, phenyl unsubstituted or substituted by deuterium, dibenzofuranyl unsubstituted or substituted by deuterium, dibenzothiophenyl unsubstituted or substituted by deuterium, or carbazolyl unsubstituted or substituted by deuterium.

9. The compound of claim 1,
wherein the compound represented by Formula 1 is any one selected from the group consisting of the following:

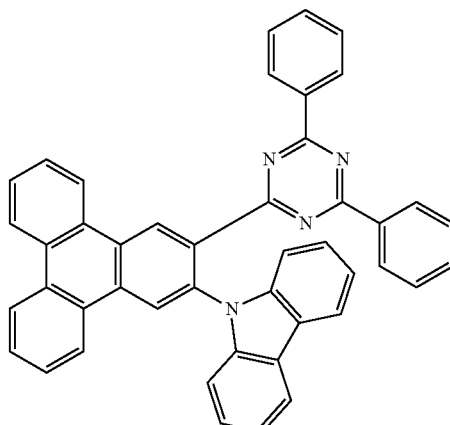

71
-continued
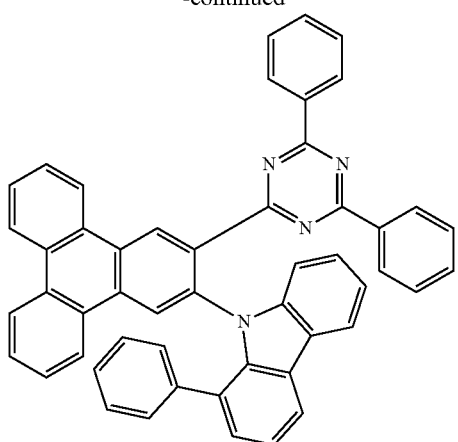
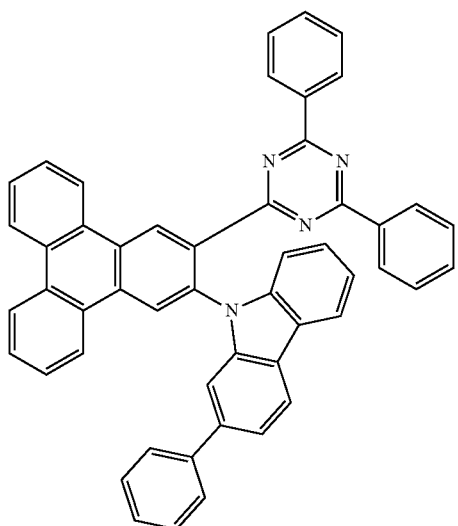
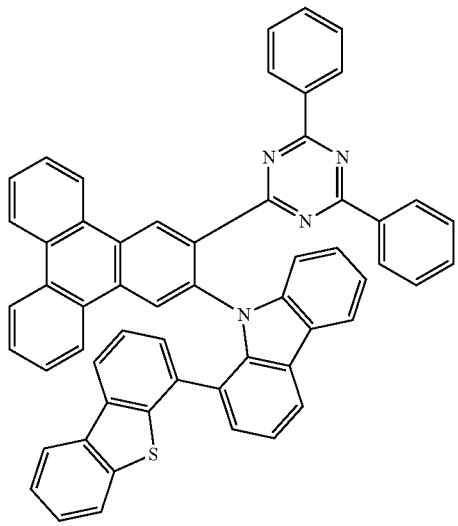
72
-continued
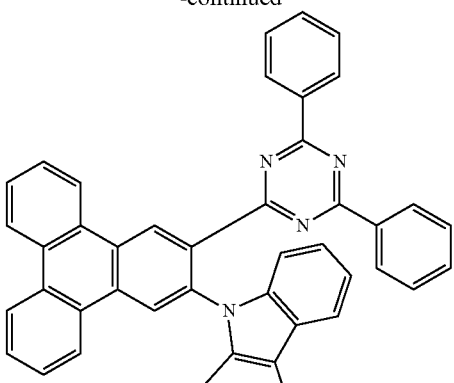
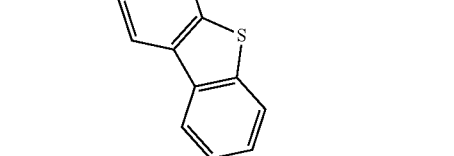
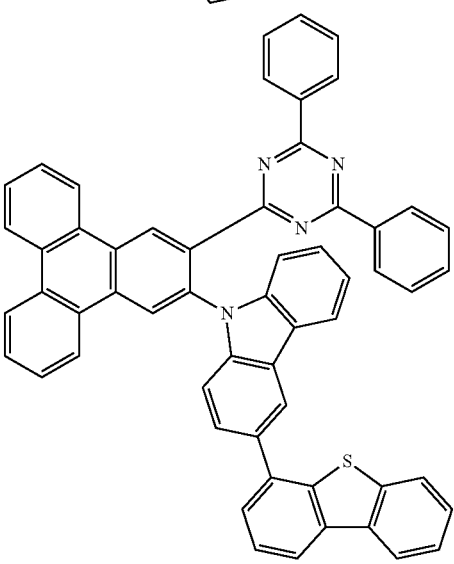
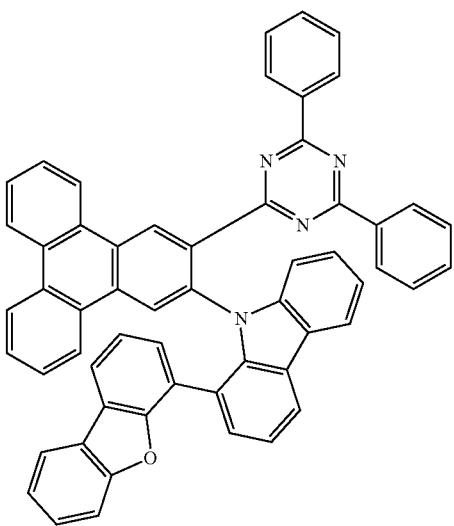

73
-continued
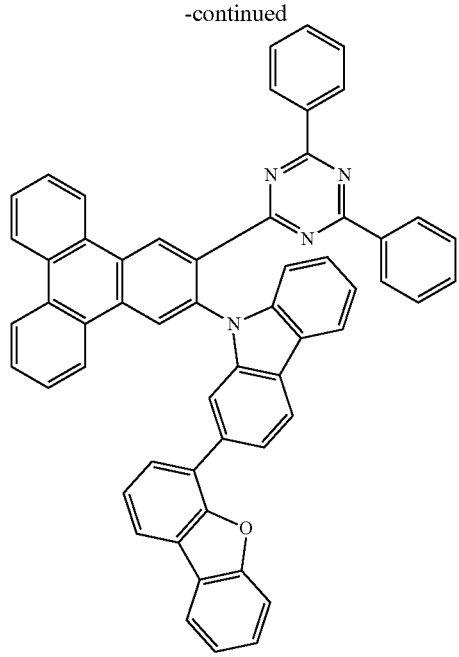
74
-continued
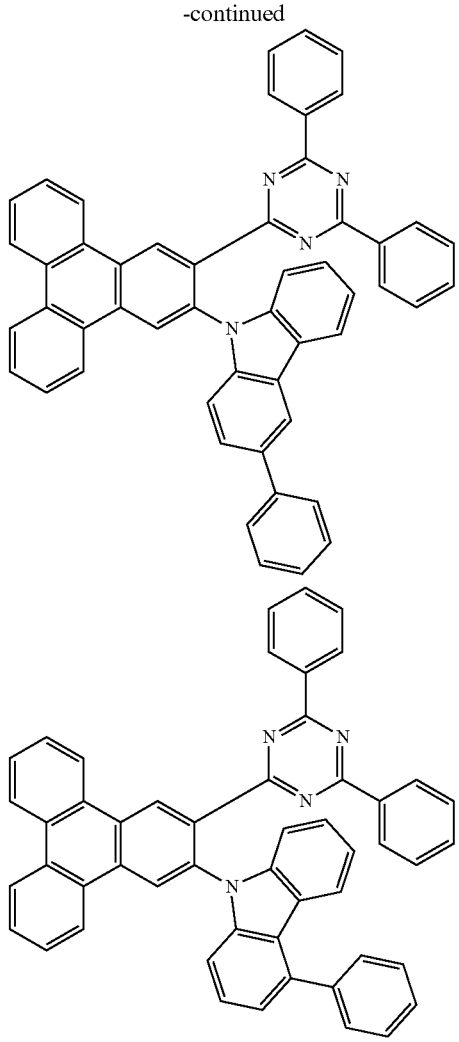
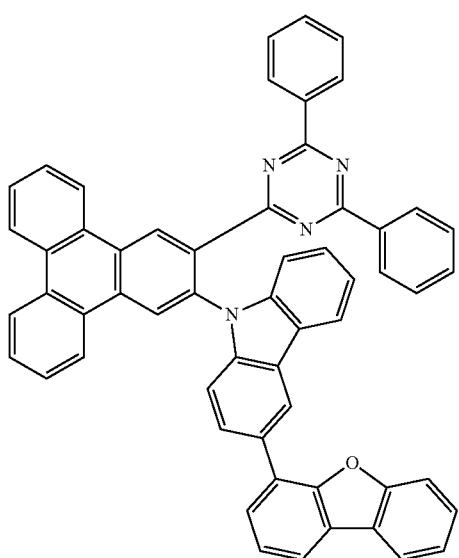

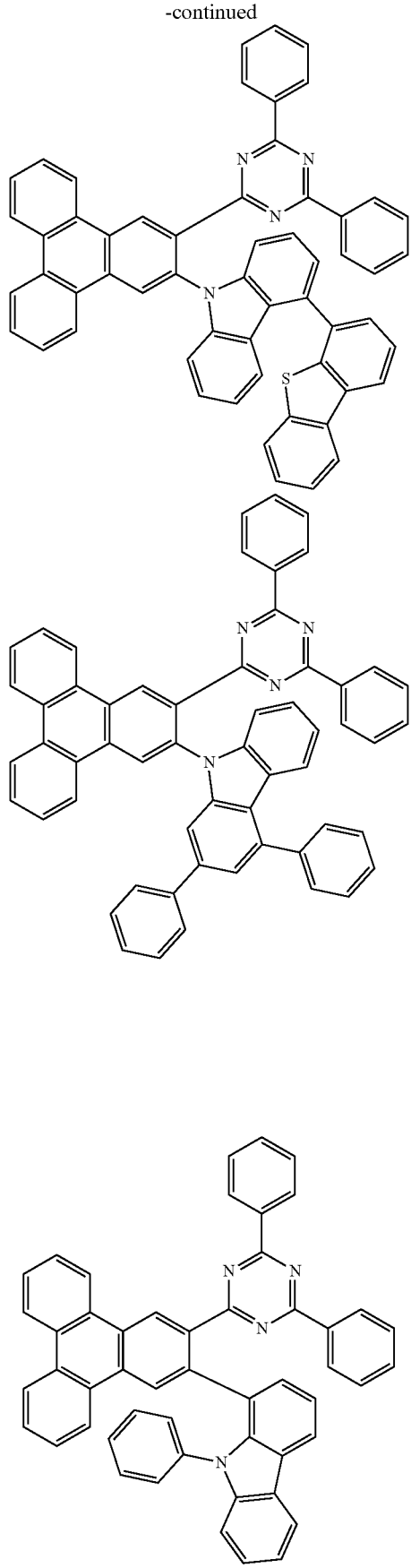
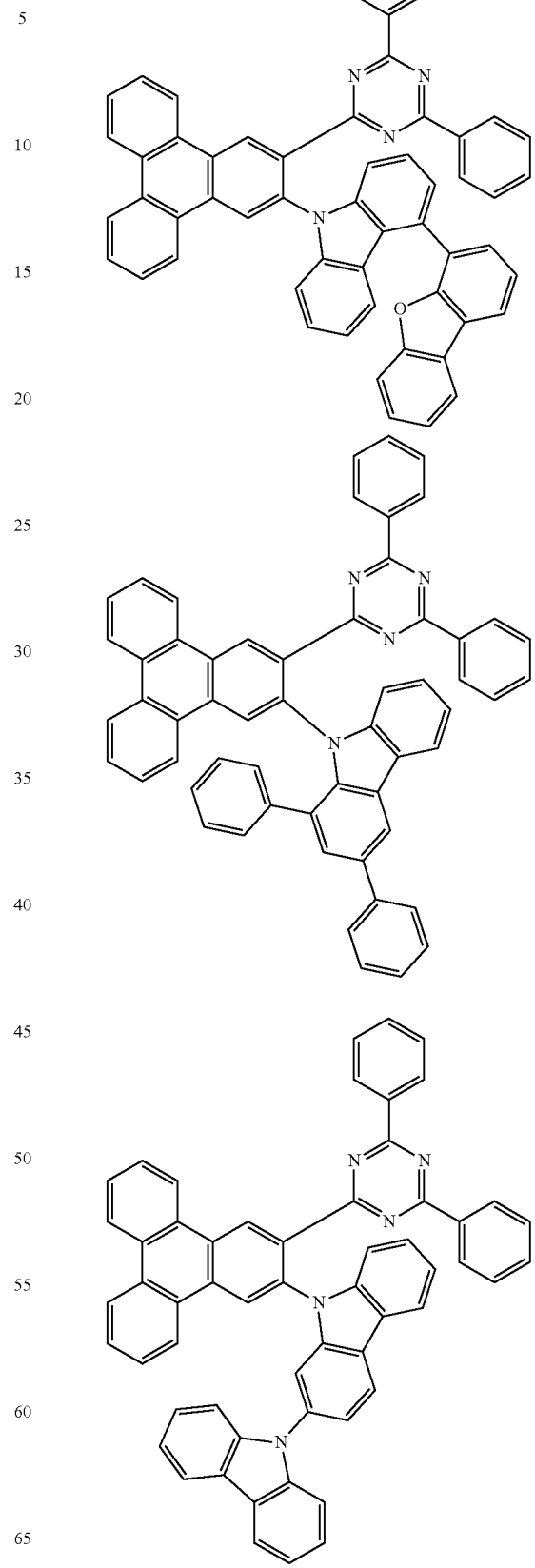

77
-continued
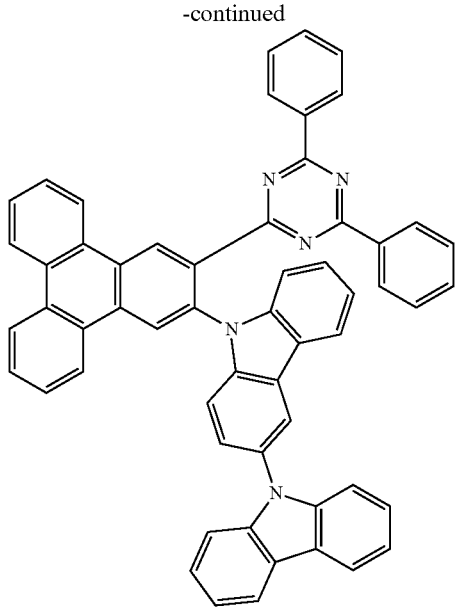
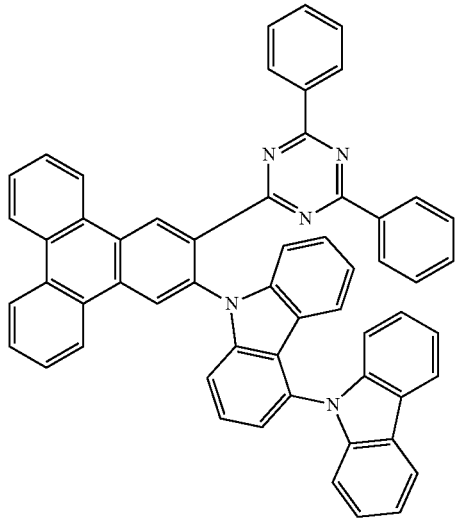
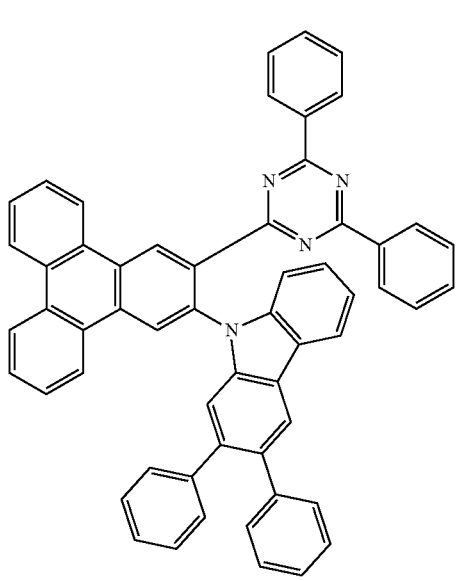
78
-continued
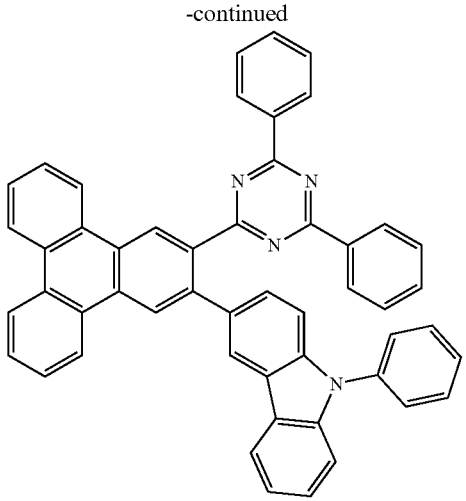
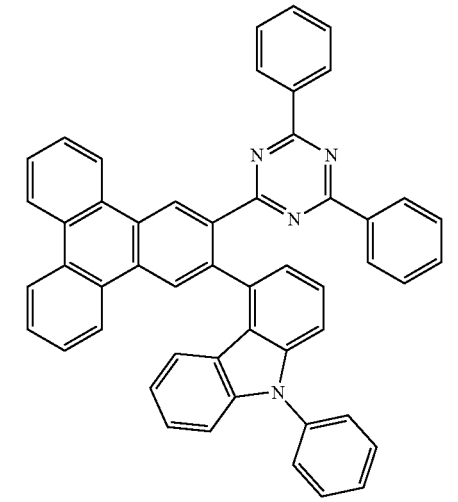
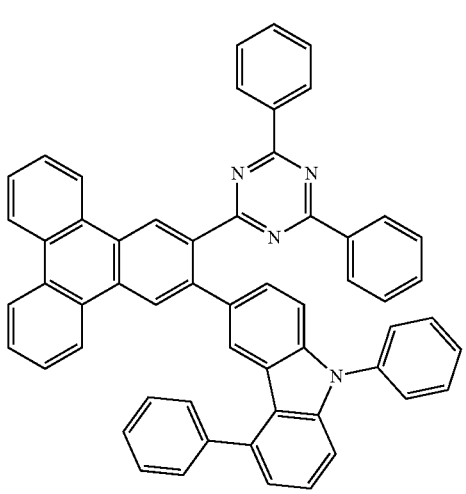

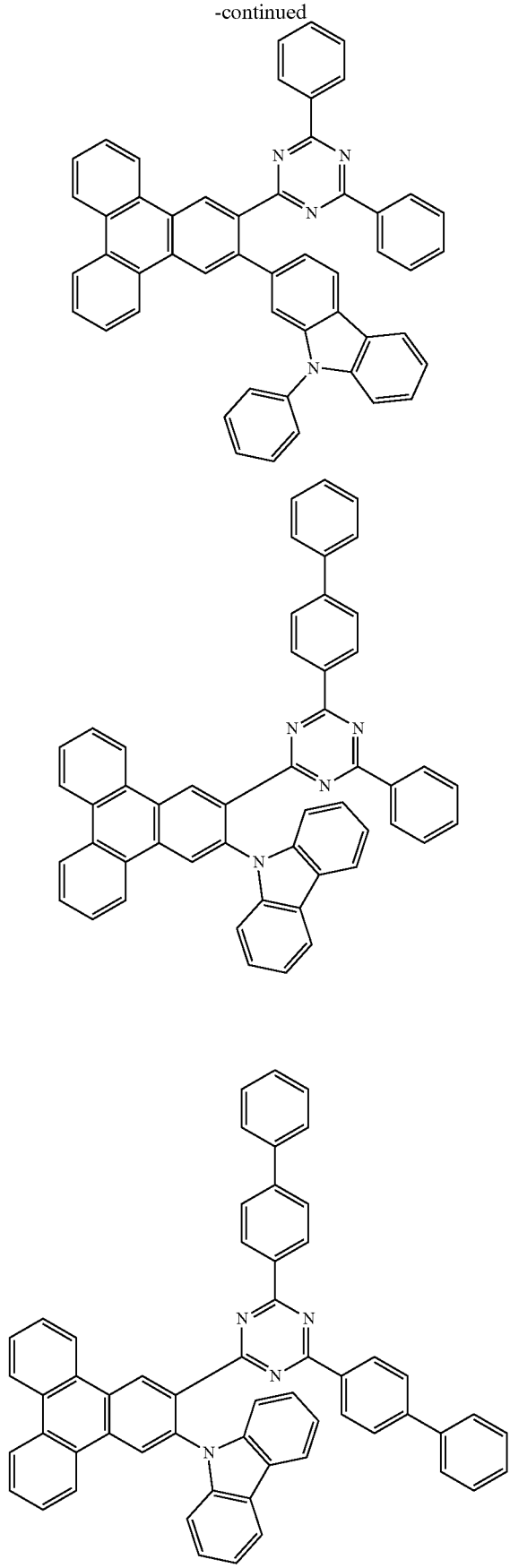

81
-continued
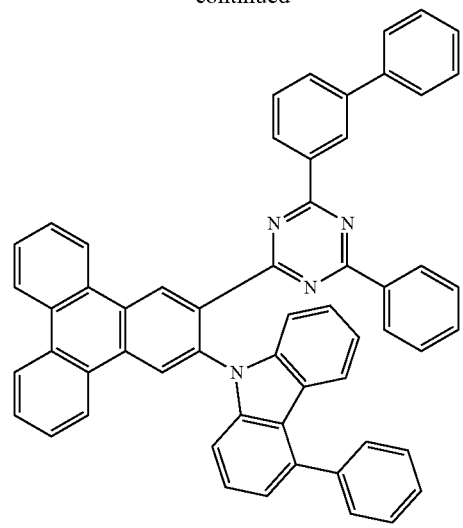
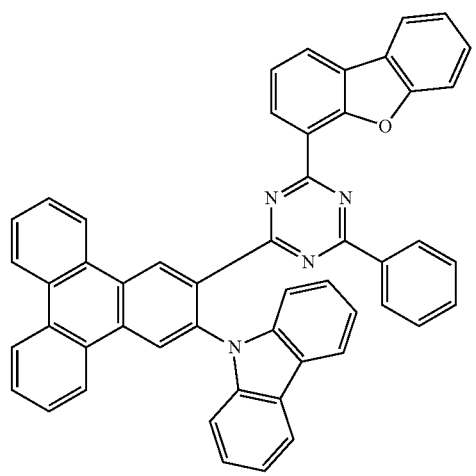
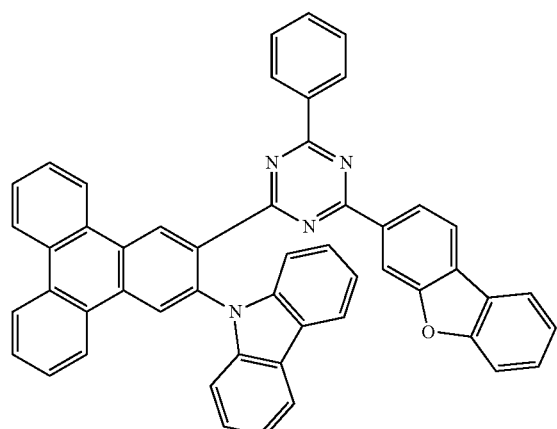
82
-continued
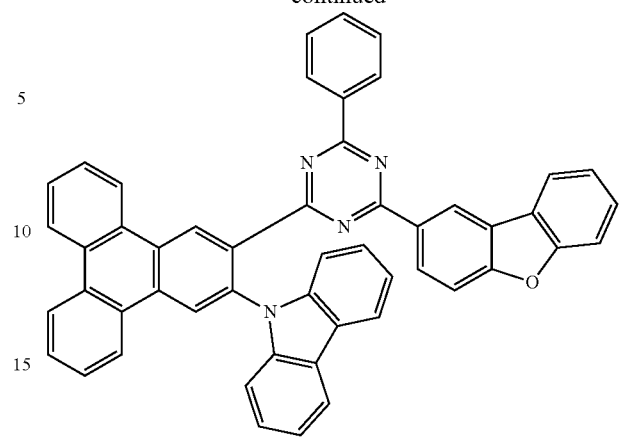
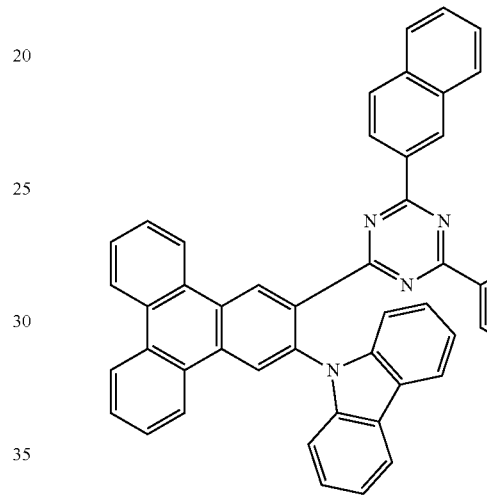
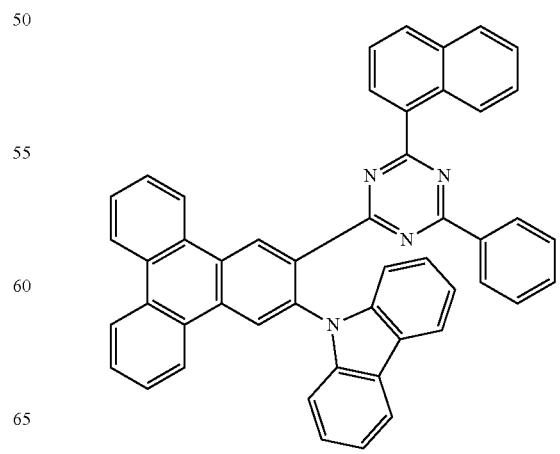

83
-continued
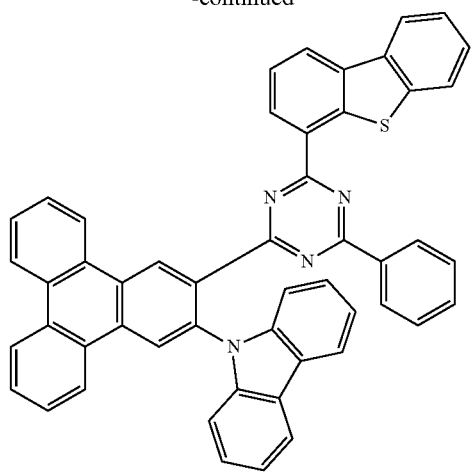
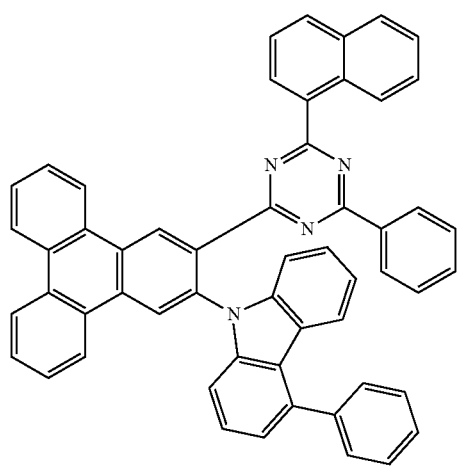
84
-continued
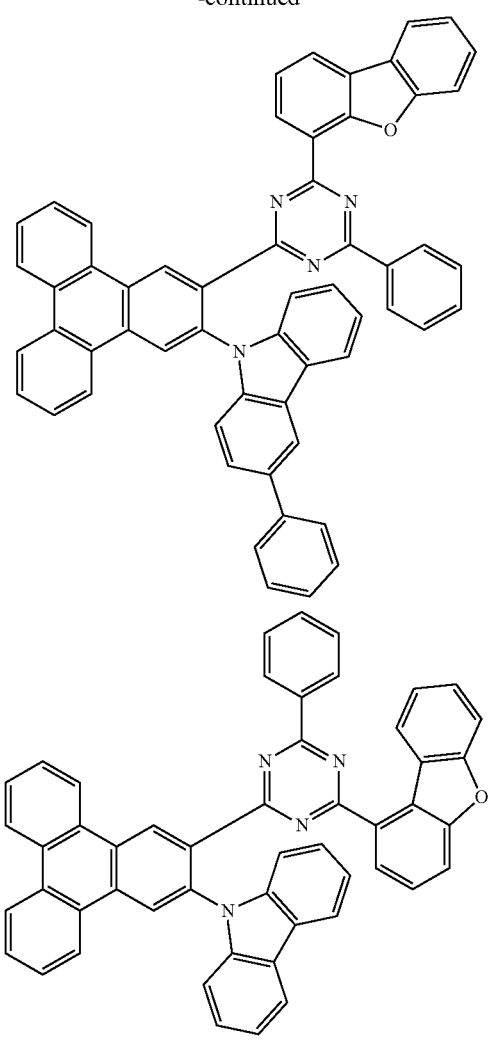

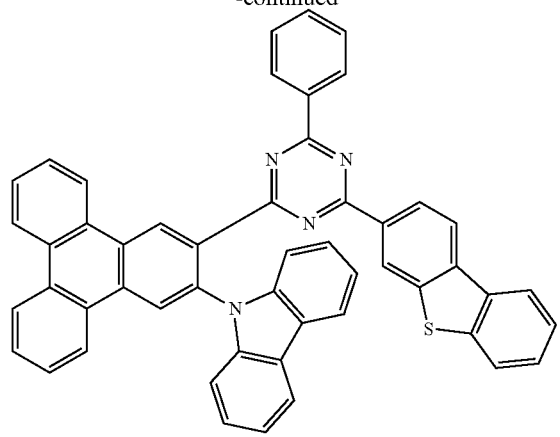
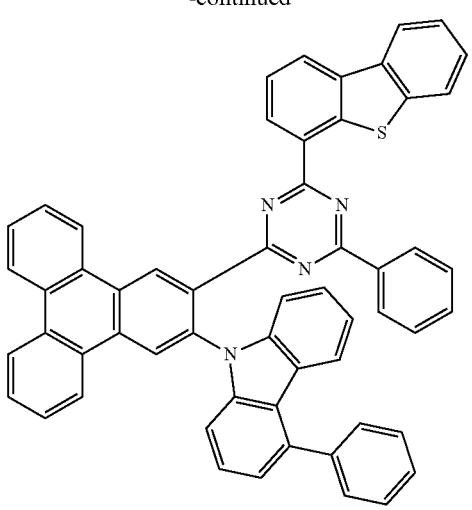
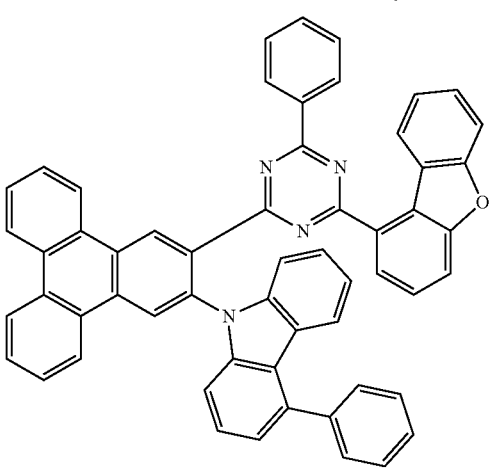
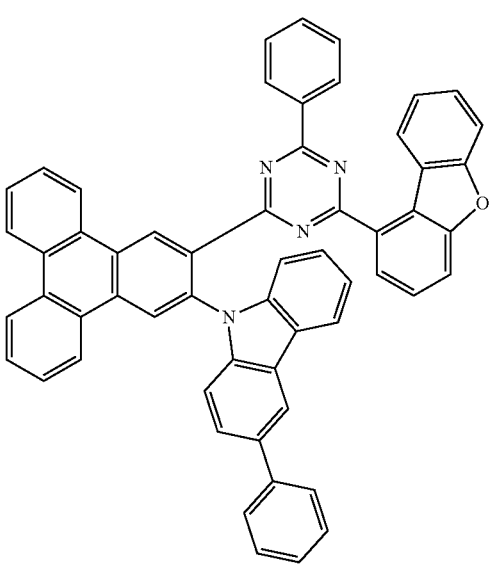

87
-continued
88
-continued
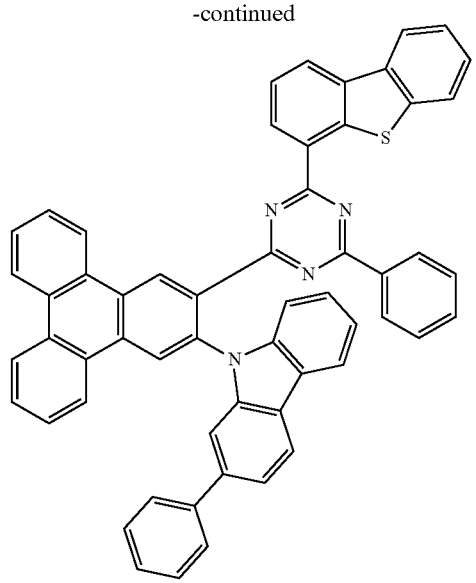
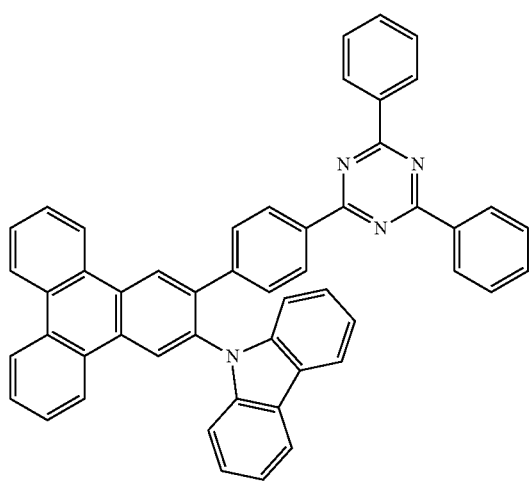
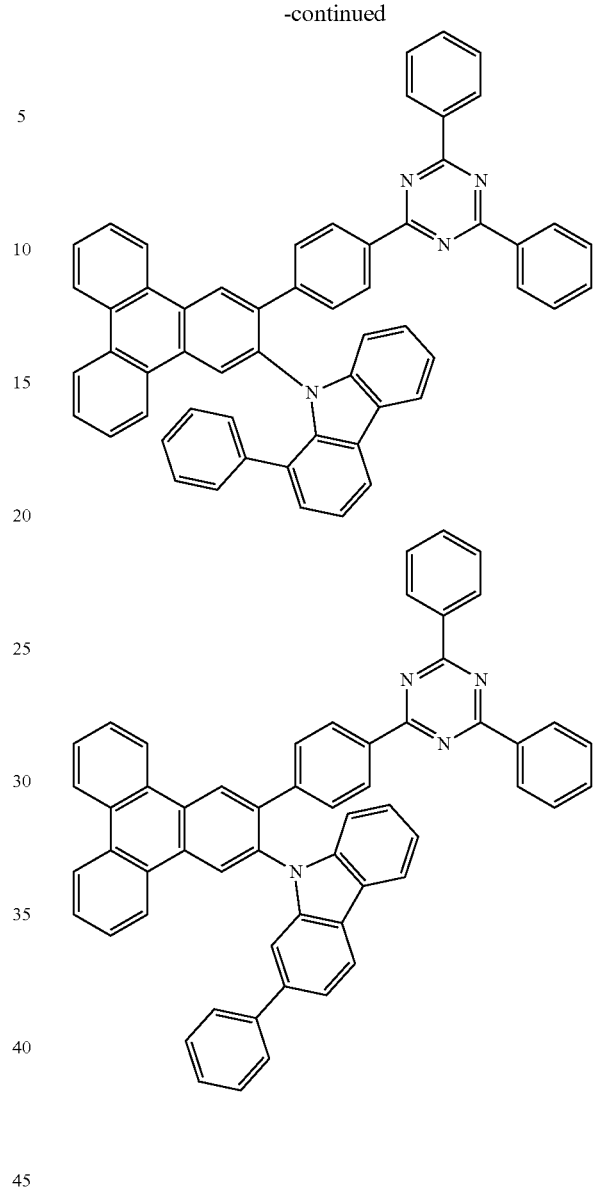

-continued
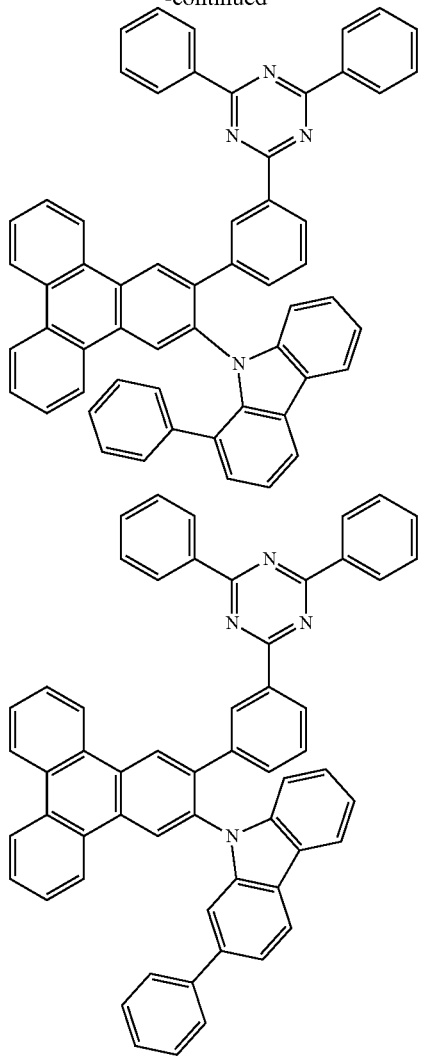
-continued
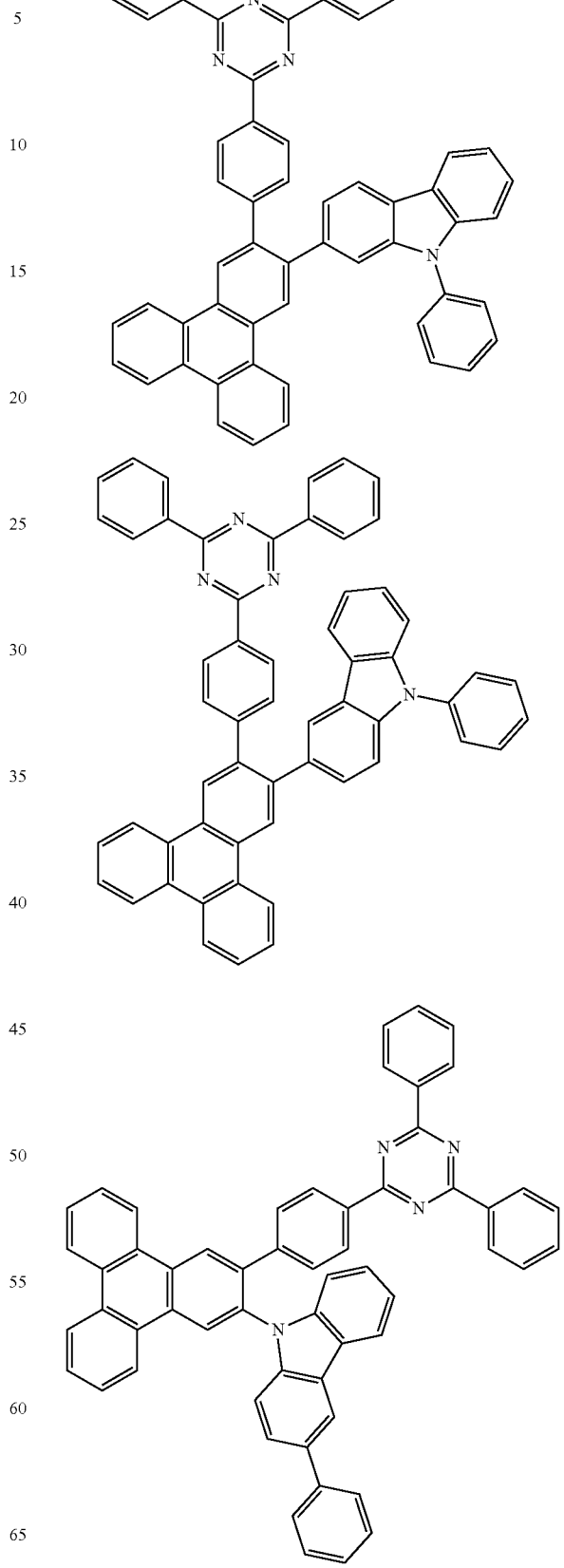

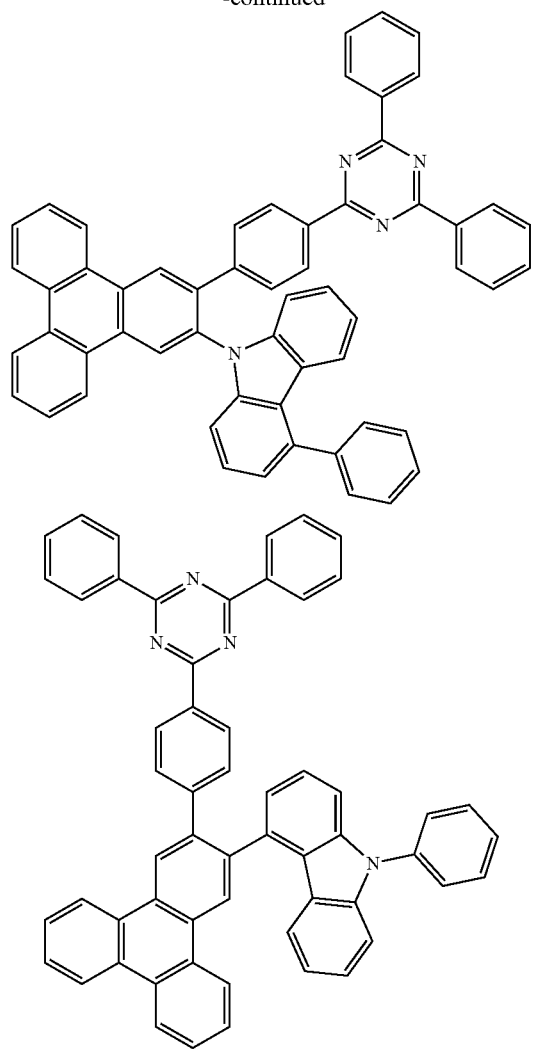
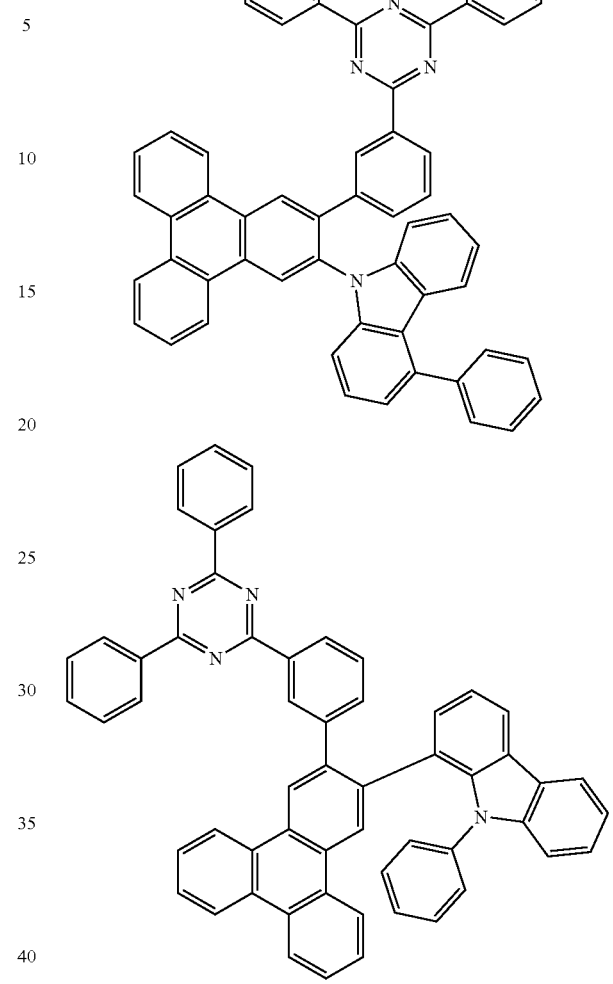
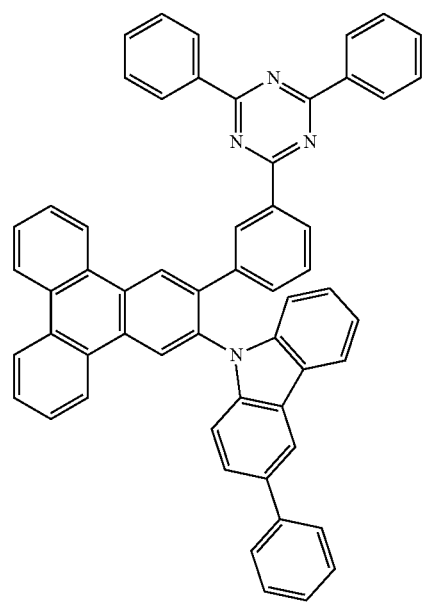
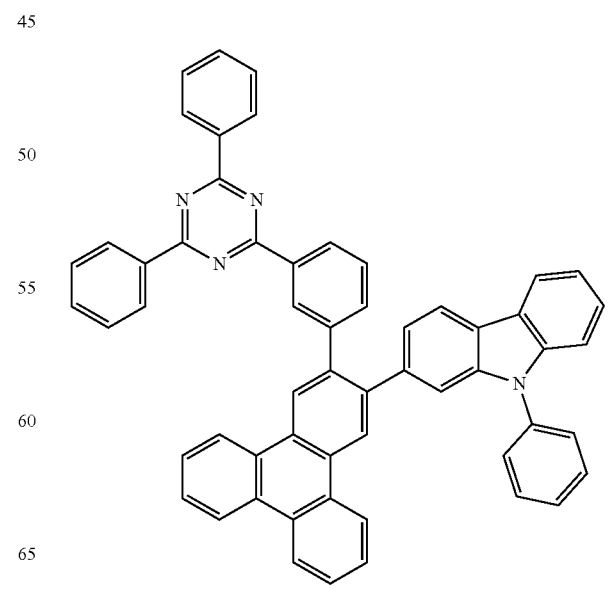

93
-continued
94
-continued
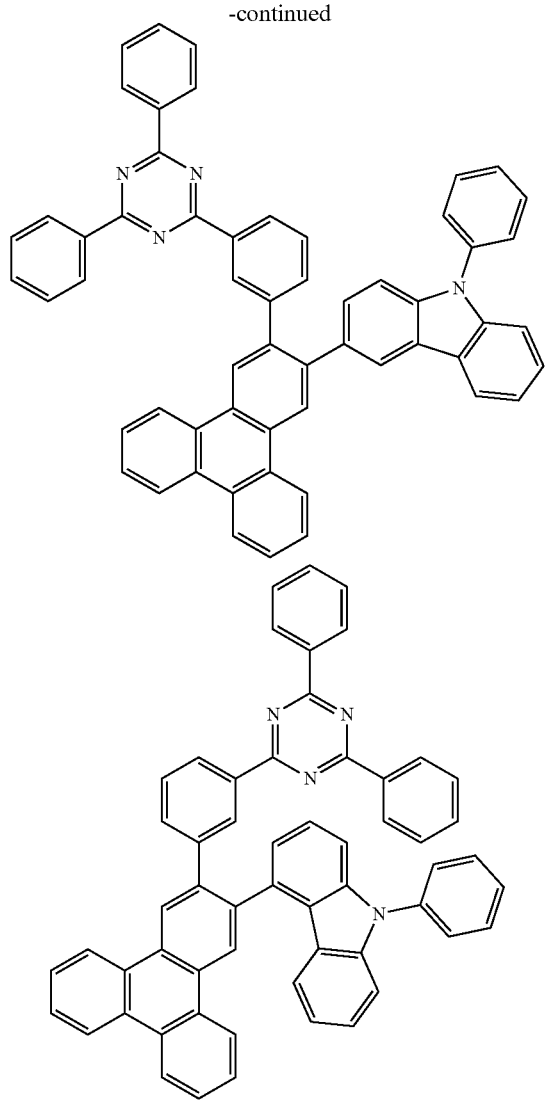
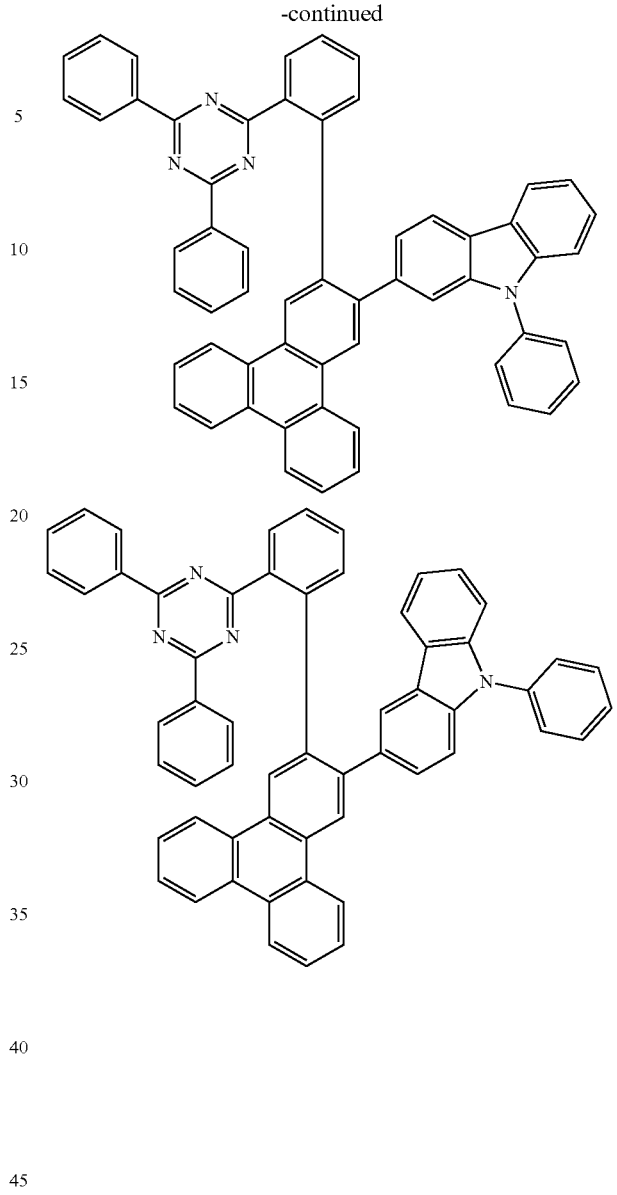
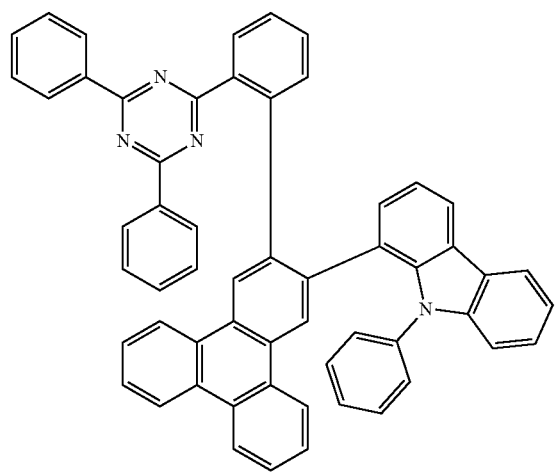

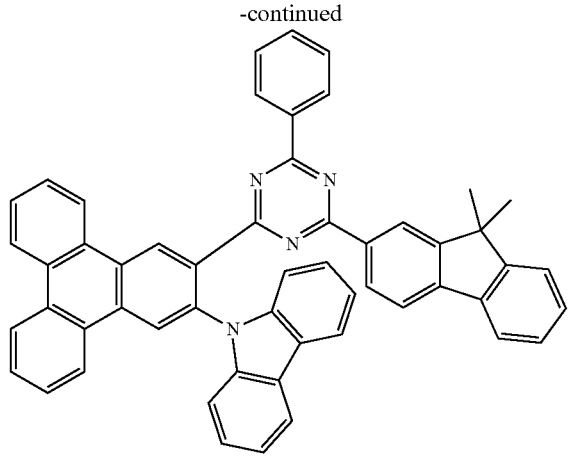
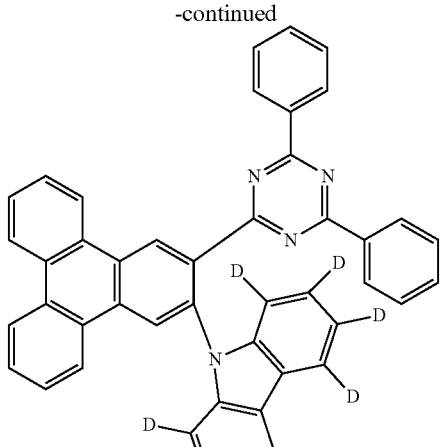
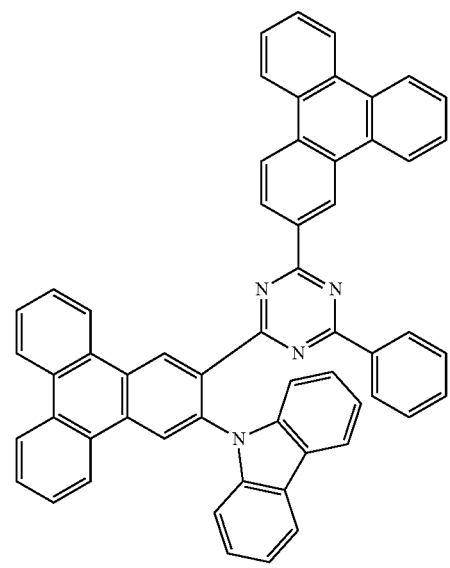
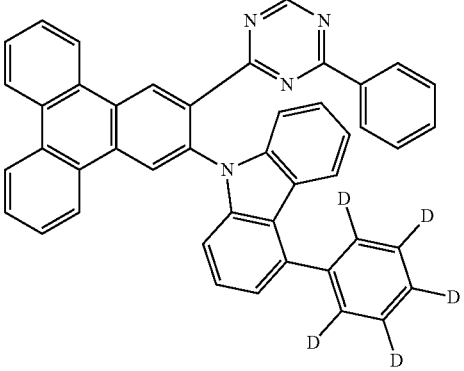
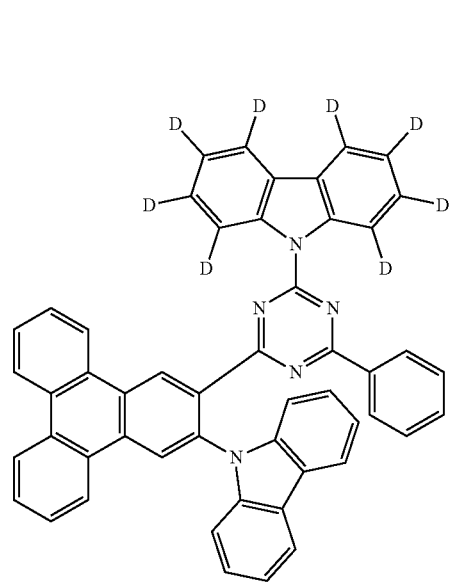
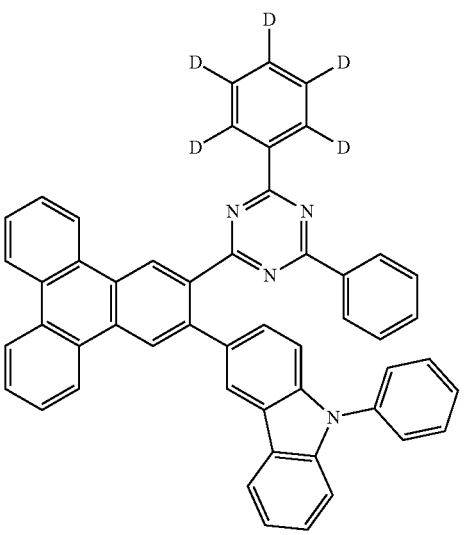

97
-continued
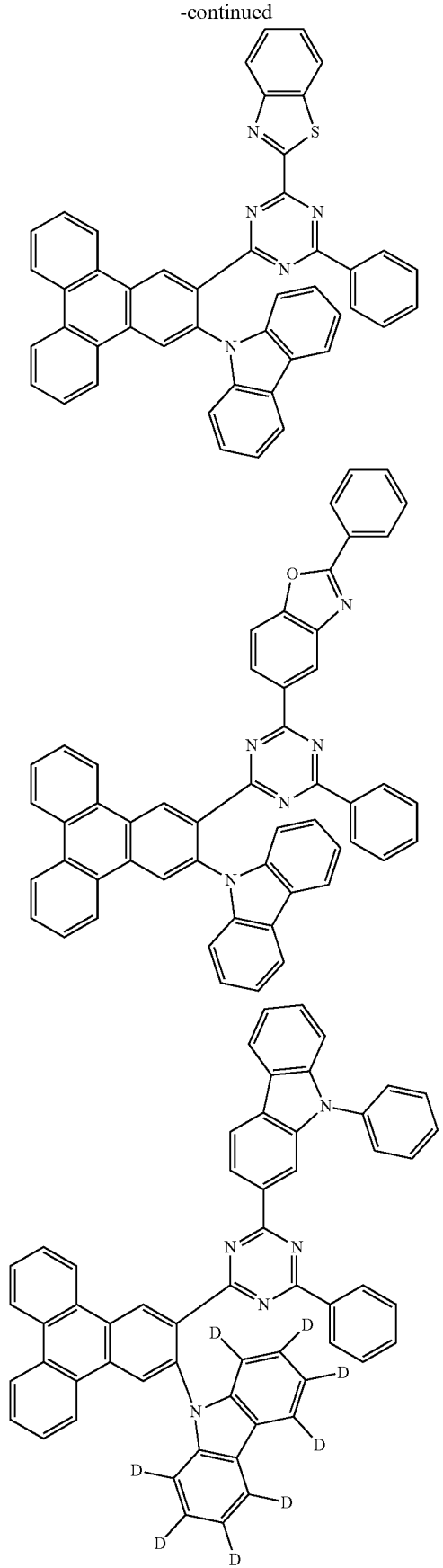
98
-continued
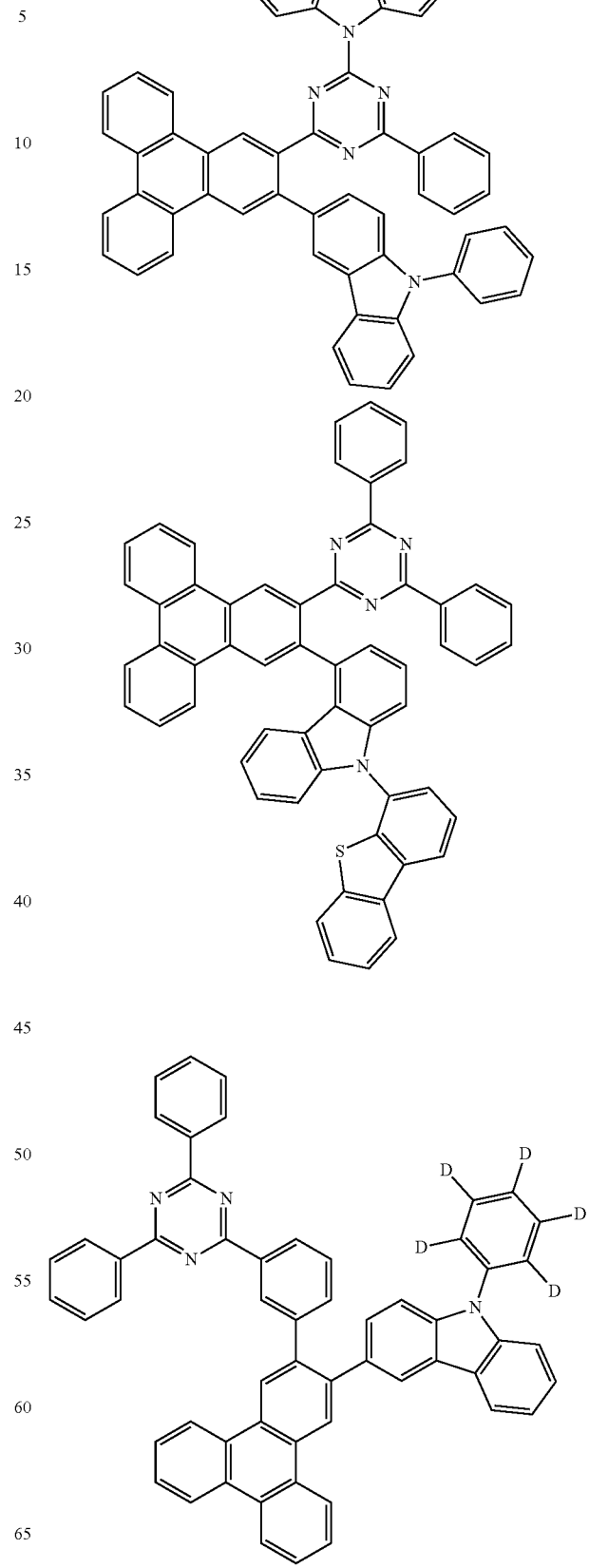

99
-continued
100
-continued
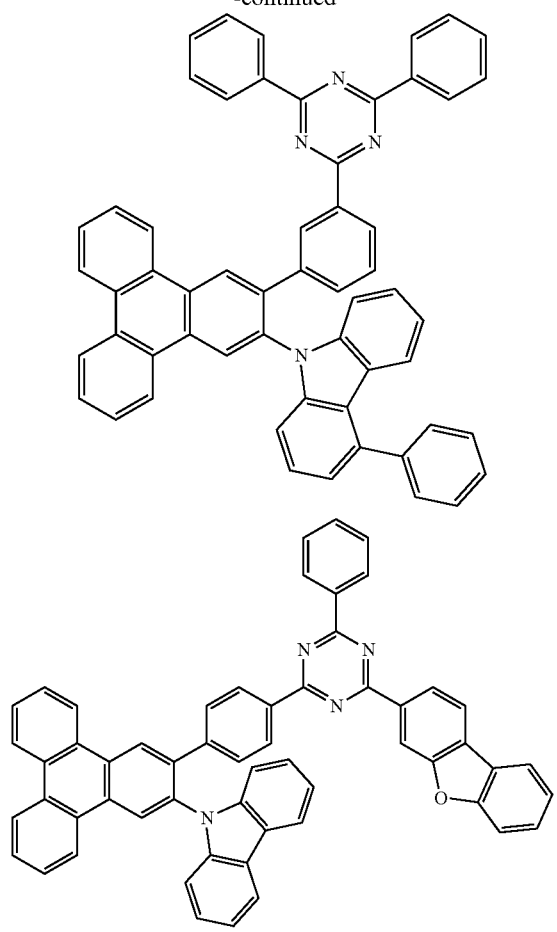
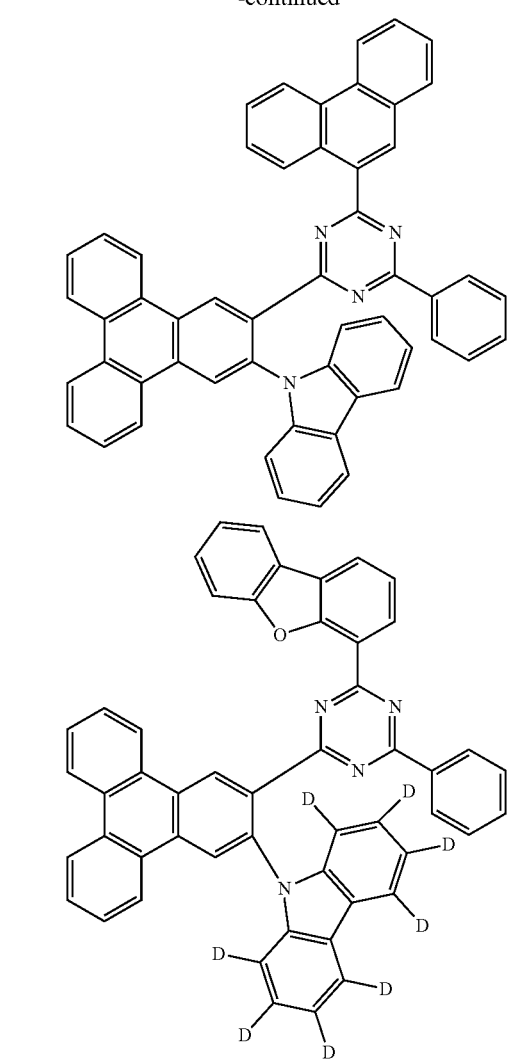
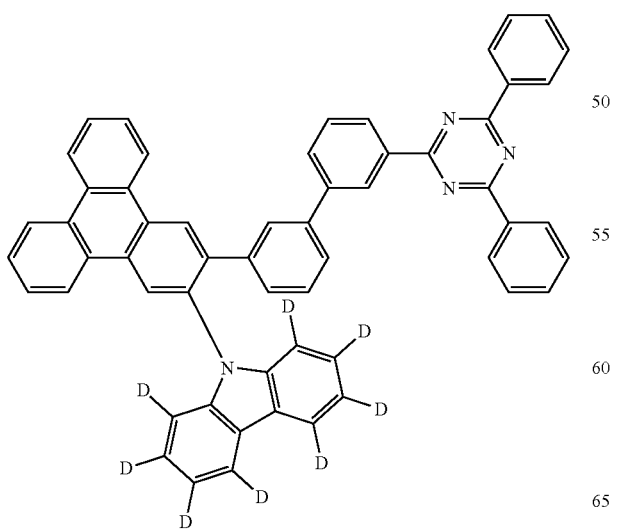
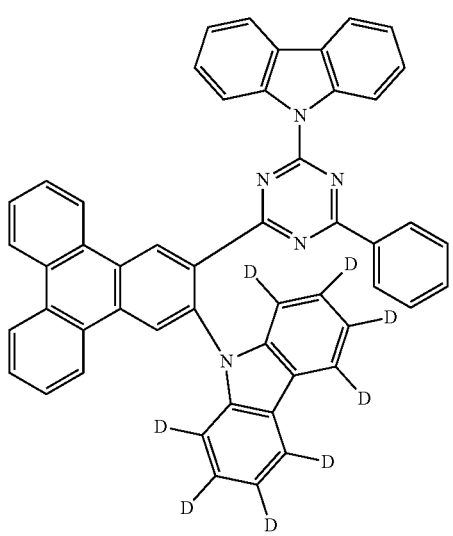

101
-continued
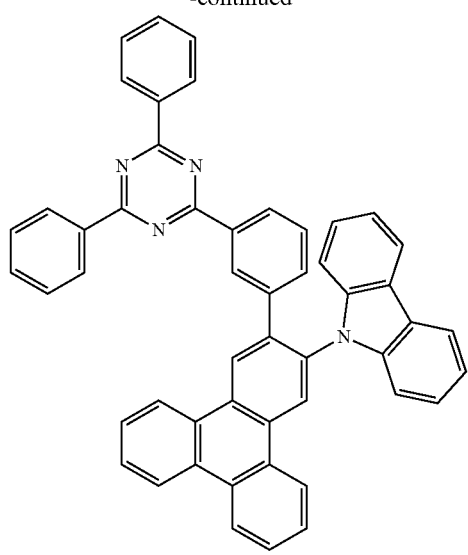
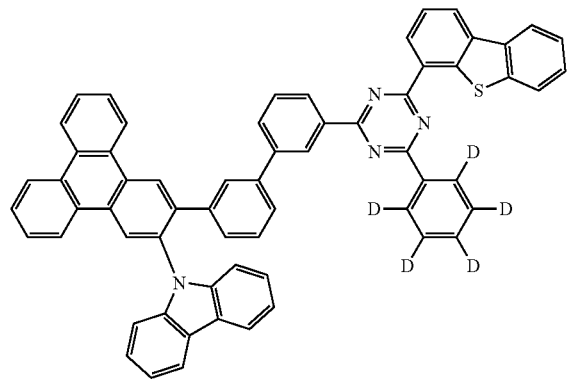
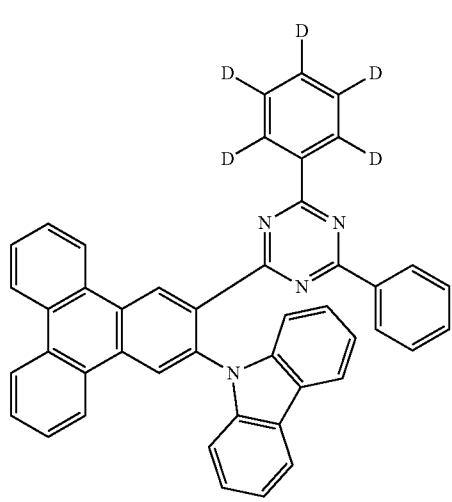
102
-continued
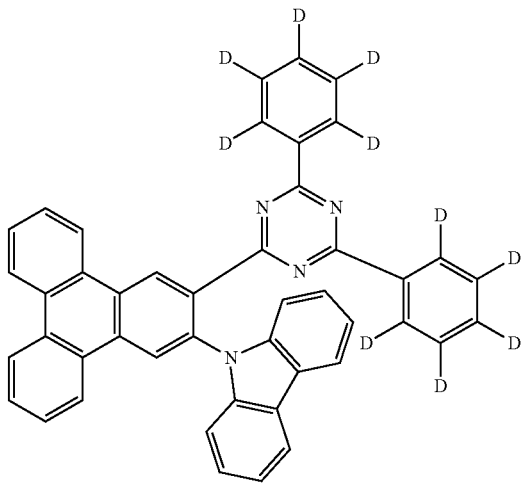
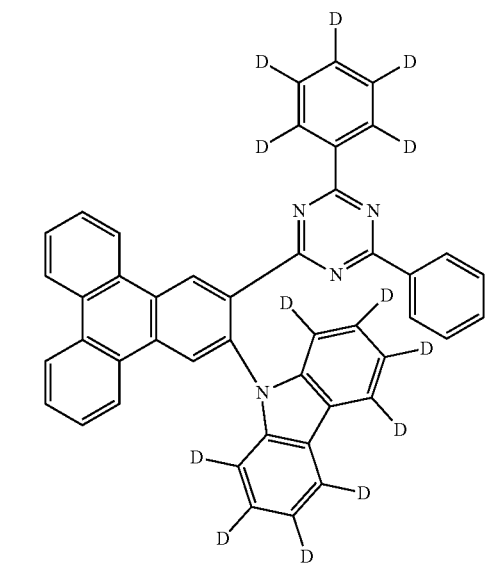

103
-continued
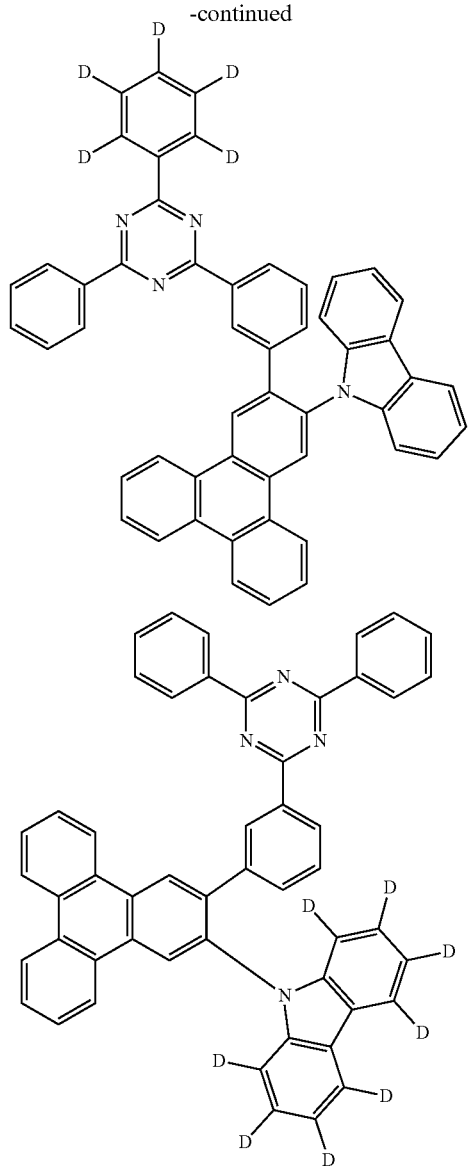
104
-continued
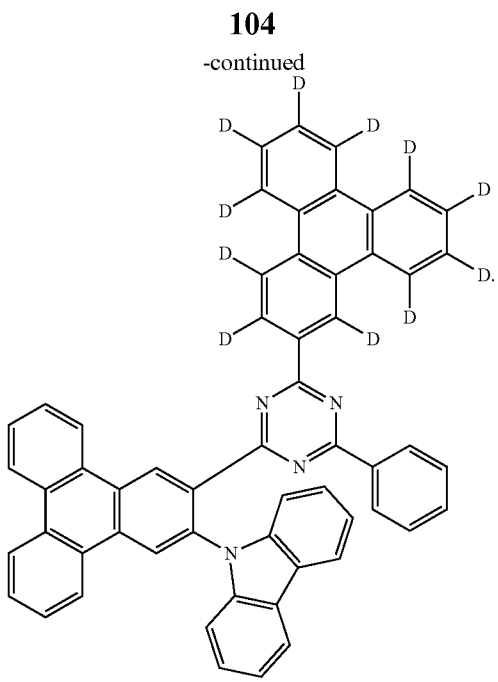
10. An organic light emitting device comprising: a first electrode; a second electrode provided to face the first electrode; and one or more organic material layers provided between the first electrode and the second electrode, wherein one or more layers of the organic material layers include the compound according to claim 1.
* * * * *